US006180112B1

(12) United States Patent
Highlander et al.

(10) Patent No.: US 6,180,112 B1
(45) Date of Patent: Jan. 30, 2001

(54) *PASTEURELLA HAEMOLYTICA* VACCINE

(75) Inventors: Sarah K. Highlander; Natalie D. Fedorova, both of Houston, TX (US)

(73) Assignee: Balyor College of Medicine, Houston, TX (US)

( * ) Notice: Under 35 U.S.C. 154(b), the term of this patent shall be extended for 0 days.

(21) Appl. No.: 09/298,367

(22) Filed: Apr. 22, 1999

Related U.S. Application Data

(63) Continuation of application No. 08/834,455, filed on Apr. 15, 1997, now abandoned.

(51) Int. Cl.$^7$ ................................................. A61K 39/102
(52) U.S. Cl. .................................. 424/255.1; 424/234.1; 424/236.1; 424/235.1; 424/200.1; 435/69.1; 435/172.1; 435/252.3; 536/23.7; 536/24.1
(58) Field of Search .............................. 424/234.1, 255.1, 424/257.1, 236.1, 200.1, 235.1; 536/23.7, 24.1; 435/320.1, 69.1, 243, 252.3, 69.3, 71.1, 172.1, 172.3; 530/350

(56) References Cited

U.S. PATENT DOCUMENTS

| | | |
|---|---|---|
| 3,328,352 | 6/1967 | Kwolek . |
| 4,167,560 | 9/1979 | Wohler, Jr. .............................. 424/92 |
| 4,171,354 | 10/1979 | Smith .................................... 424/92 |
| 4,328,210 | 5/1982 | Kucera ................................... 424/92 |
| 4,336,074 | 6/1982 | Dinkelacker ............................. 134/8 |
| 4,683,195 | 7/1987 | Mullis et al. ............................ 435/6 |
| 4,683,202 | 7/1987 | Mullis .................................... 435/91 |
| 4,955,317 | 9/1990 | Kinoshita et al. .................... 118/689 |
| 4,957,739 | 9/1990 | Berget et al. .......................... 424/92 |
| 5,028,423 | 7/1991 | Prickett ............................... 424/85.8 |
| 5,055,400 | 10/1991 | Lo et al. ............................. 435/69.1 |
| 5,336,491 | 8/1994 | Berget et al. ...................... 424/190.1 |
| 5,476,657 | 12/1995 | Potter ................................ 424/184.1 |

FOREIGN PATENT DOCUMENTS

91/06653 * 5/1991 (WO) .

OTHER PUBLICATIONS

Cruz et al. Molec. Microbiol. 1990. 4(11): 1933–1939, 1990.*
Nicaud et al. Febs Letters. 1985. 187(2): 339–344, 1985.*
"United States Pharmacopeia," vol. XXII (1990, *United States Pharmacopeial Convention*, Rockville, MD, p. 151.
Anderson and Young, "Quantitative Filter Hybridisation," in *Nucleic Acid Hybridisation* (1985).
Azad et al., "Construction of conjugative shuttle and suicide vectors for *Pasteurella haemolytica* and *P. multocida,"* Gene 145:81–85 (1994).
Azad et al., "Distinct plasmid profiles of *Pasteurella haemolytica* serotypes and the characterization and amplification in *Escherichia coli* ampicillin–resistance plasmids encoding ROB–1 β–lactamase," *J. Gen. Microbiol.* 138:1185–1196 (1994).

Blood, *Pocket Companion to Veterinary Medicine,* Baillière Tindall, London, pp. 309–310 (1994) .
Briggs et al., "Characterization of a Restriction Endonuclease, PhaI, from *Pasturella haemolytica* Serotype A1 and Protection of Heterologous DNA by a Cloned PhaI methyltransferase Gene," *App. Environ. Microbiol.* 60:2006–2010 (1994).
Chang et al., "Characterization of plasmids with antimicrobial resistant genes in *Pasturella haemolytica* A1," *J. DNA Seq. Map.* 3:89–97 (1992).
Chang et al., "Identification and Characterization of the *Pasturella haemolytica* Leukotoxin," *Infect. Immun.* 55:2348–2354 (1987).
Clewell et al., "Unconstrained bacterial promiscuity: the Tn916–Tn1545 family of conjugative transposons," *Trends Microbiol.* 3:229–236 (1995).
Clinkenbeard et al., "Transmembrane Pore Size and Role of Cell Swelling in Cytotoxicity Caused by *Pasturella haemolytica* Leukotoxin," *Infect. Immun.* 57:420–425 (1989).
Confer et al., "Bovine pneumonic pasteurellosis: Immunity to *Pasturella haemolytica,*" *J. Amer. Vet. Med. Assoc.* 193:1308–1316 (1988).
Confer et al., "Molecular Aspects of Virulence of *Pasturella haemolytica,*" *Can. J. Vet. Res.* 54:S48–S52 (1990).
Coombs, *Dictionary of Biotechnology,* Stockton Press, New York NY (1994).
Craig et al., "A Plasmid Which Can Be Transferred Between *Escherichia coli* and *Pasturella haemolytica* by electroporation and Conjugation," *J. Gen. Microbiol.* 135:2885–2890 (1989).
Dieffenbach and Dveksler, *PCR Primer, a Laboratory Manual,* Cold Spring Harbor Press, Plainview NY (1995).
Diker et al., "Antimicrobial susceptibility of *Pasturella haemolytica* and *Pasturella multocida* isolated from pneumonic ovine lungs," *Vet. Rec.* 134:597–598 (1994).
Dixon et al., "An Analysis of the Complete Nucleotide Sequence of the *Haemophilus ducreyi* Broad–Host–Range Plasmid pLS88," *Plasmid* 32:228–232 (1994).
Donachie et al., "Comparison of Cell Surface Antigen Extracts from Two Serotypes of *Pasturella haemolytica,"* J. Gen. Microbiol. 130:1209–1216 (1984).
Dower et al., "High Efficiency Transformation of *E. coli* by high voltage electroporation," *Nucl. Acids Res.* 16:6127–6145 (1988).

(List continued on next page.)

*Primary Examiner*—Jennifer Graser
(74) *Attorney, Agent, or Firm*—Medlen & Carroll, LLP

(57) ABSTRACT

The present invention is directed to compositions and methods for the production for the prevention of disease due to *P. haemolytica*. In particular, the present invention provides *P. haemolytica* strains that produce inactive leukotoxin for vaccine and other uses. The present invention also provides compositions and methods for genetic manipulations in *P. haemolytica*.

16 Claims, 19 Drawing Sheets

OTHER PUBLICATIONS

Figure 1:
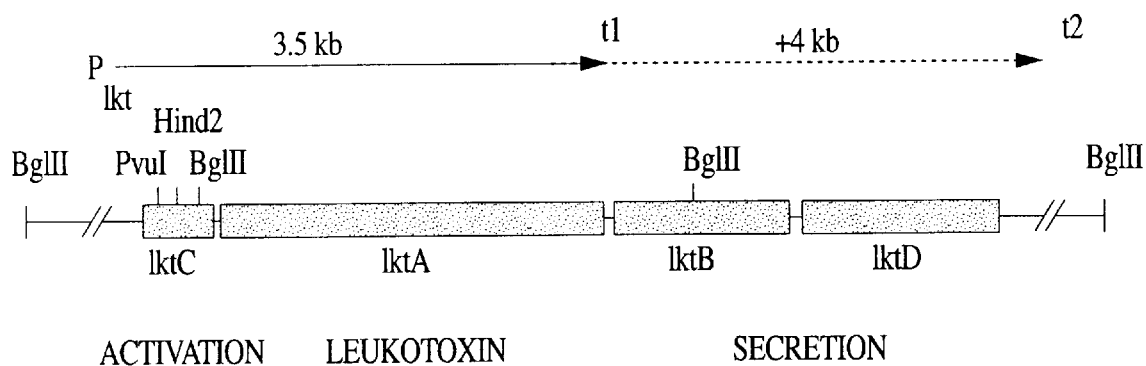

*FDA Guidelines for Parenteral Drugs* (Dec. 1987).

Fleischmann et al., "Whole–Genome Random Sequencing and Assembly of *Haemophilus influenzae* Rd," *Science* 269:496–512 (1995).

Forestier and Welch, "Nonreciprocal Complementation of the hlyC and lktC Genes of the *Escherichia coli* Hemolysin and *Pasturella haemolytica* Leukotoxin Determinants," *Infect. Immun.* 58:828–832 (1990).

Frank, "Pasteurellosis of Cattle," Pasteurella and Pasteurellosis, C. Adlam and J. Rutters (eds.), Academic Press, San Diego, CA, pp. 197–222 (1989).

Frey, "Construction of a broad host range shuttle vector for gene cloning and expression in *Actinobacillus pleuropneumoniae* and other Pasteurellaceae," *Res. Microbiol.* 143:263–269 (1992).

Frey et al., "Identification of a Second Hemolysin (HlyII) in *Actinobacillus pleuropneumonia* Serotype 1 and Expression of the Gene in *Escherichia coli,*" *Infect Immun.* 60:1671–1676 (1992).

Gay et al., "Positive Selection Procedure for Entrapment of Insertion Sequence Elements in Gram–Negative Bacteria," *J. Bacteriol.* 164:918–921 (1985).

Gentry et al., "Serum Neutralization of Cytotoxin from *Pasturella Haemolytica* Serotype 1 and Resistance to Experimental Bovine Pneumonic Pasteurellosis," *Vet. Immunol., Immunophathol.* 9:239–250 (1985).

Gentry and Srikumaran, "Neutralizing monoclonal antibodies to *Pasturella haemolytica* leukotoxin affinity–purify the toxin from crude culture supernatants," *Microbial Pathogen.* 10:411–417 (1991).

Gu et al., "Independent Control of Immunoglobulin Switch Recombination at Individual Switch Regions Evidenced through Cre–loxP–Mediated Gene Targeting," *Cell* 73:1155–1164 (1993).

Gutterson and Koshland, "Replacement and amplification of bacterial genes with sequences altered in vitro," *Proc. Natl. Acad. Sci. USA* 80:4894–4988 (1983).

Haynes, *Keeping Livestock healthy,* Garden Way Publishing, Charlotte, VA, pp. 145–148, (1978).

Highlander and Garza, "The restriction–modification system of *Pasturella haemolytica* is a member of a new family of type I enzymes," *Gene* 178:89–96 (1996).

Highlander and Weinstock, "Static DNA Bending and Protein Interactions Within the *Pasturella haemolytica* Leukotoxin Promoter Region: Development of an Activation Model for Leukotoxin Trancriptional Control," *DNA Cell Biol.* 13:171–181 (1994).

Highlander et al., "DNA Sequence of the *Pasturella haemolytica* Leukotoxin Gene Cluster," *DNA Cell Biol.,* 8:15–28 (1989).

Highlander et al., "Expression of the *Pasturella haemolytica* Leukotoxin Is Inhibited by a Locus That Encodes an ATP–Binding Cassette Homolog," *Infect. Immun.* 61:3942–3951 (1993).

Highlander et al., "Secretion and Expression of the *Pasturella haemolytica* Leukotoxin," *J. Bacteriol.* 172:2343–2350 (1990).

Homchampa et al., "Construction and vaccine potential of an aroA mutant of *Pasturella haemolytica,*" *Vet. Microbiol.* 42:35–44 (1994).

Issartel et al., "Activation of *Escherichia coli* prohaemolysin to the mature toxin by acyl carrier protein–dependent fatty acylation," *Nature* 351:759–761 (1991).

Keilty and Rosenberg, "Constitutive Function of a Positively Regulated Promoter Reveals New Sequences Essential for Activity," *J. Biol. Chem.* 262:6389–6395 (1987).

Kumar et al., "The Minus 35–Recognition Region of *Escherichia coli* Sigma 70 is Inessential for Initiatio of Transcription at an Extended Minus 10 Promoter," *J. Mol. Biol.* 232:406–418 (1993).

Laemmli, "Cleavage of Structural Proteins during the Assembly of the Head of Bacteriophage T4," *Nature* 227:680–685 (1970).

Lessley et al., "Saline–Extracted Antigens of *Pasteurella Haemolytica:* Separation by Chromatofocusing, Preliminary Characterization, and Evaluation of Immunogenicity," *Vet. Immunol. Immunopathol.* 10:279–296 (1985).

Levinson and Gutman, "Slipped–Strand Mispairing: A Major Mechanism for DNA Sequence Evolution," *Mol. Biol. Evol.* 4:203–221 (1987).

Livrelli et al., "Sequence and Molecular Characterization of the ROB–1 β–Lactamase Gene from *Pasteurella haemolytica,*" *Antimicrob. Agents Chemother.* 35:242–251 (1991).

Lo, "An analysis of the codon usage of *Pasteurella haemolytica* A1," *FEMS Microbiol. Lett.* 100:125–132 (1992).

Lo et al., "Nucleotide Sequence of the Leukotoxin Genes of *Pasteurella haemolytica* A1," *Infect. Immun.* 55:1987–1996 (1989).

Lukomski et al., "Identification of the O Antigen Polymerase (rfc) Gene in *escherichia coli* O4 by Insertional Mutagenesis Using a Nonpolar Chloramphenicol Resistance Cassette," *J. Bacteriol.* 178:240–247 (1996).

Maniatis et al., *Molecular Cloning: A Laboratory Manual,* Cold Spring Harbor Press, Cold Spring Harbor, New York (1982).

Martin et al., "Factors Associated with Mortality in Feedlot Cattle: The Bruce County Beef Cattle Project," *Can. J. Comp. Med.* 44:1–10 (1980).

McMillan, "Working Together, Sharing Knowledge," *Bovine Respiratory Disease: A Symposium,* R.W. Loan (ed.), p. 64 (1984).

Miller, *Experiments in Molecular Genetics,* Cold Spring Harbor Laboratory, Cold Spring Harbor, NY (1972).

Mullis et al., "Specific Enzymatic Amplification of DNA In Vitro: The Polymerase Chain Reaction," *Cold Spring Harbor Symposia,* vol. LI, pp. 263–273 (1986).

Murphy et al., "Hemolytic Activity of the *Pasteurella haemolytica* Leukotoxin," *Infect. Immun.* 63:3209–3212 (1995).

Neumann et al., "A Novel Rapid Assay for Chloramphenicol Acetyltransferase Gene Expression," *BioTechn.* 5:444–447 (1987).

Nielsen et al., "Peptide nucleic acids (PNAs): Potential antisense and anti–gene agents," *Anticancer Drug Des.* 8:53–63 (1993).

Oka et al., "Nucleotide Sequence of the Kanamycin Resistance Transposon Tn903," *J. Mol. Biol.* 147:217–226 (1981).

Pearson, *Pyrogens: Endotoxins, LAL Testing and Depyrogenation,* Marcel Dekker, New York, pp. 150–158 (1985).

Petras et al., "Antigenic and Virulence Properties of *Pasteurella haemolytica* Leukotoxin Mutants," *Infect. Immun.* 63:1033–1039 (1995).

Poyart–Salmeron, "The integration–excision system of the conjugative transposon Tn 1545 is structurally and functionally related to those of lambdoid phages," *Mol. Microbiol.* 4:1513–1521 (1990).

Sansonetti et al., "Involvement of a Plasmid in the Invasive Ability of *Shigella flexneri,*" *Infect. Immun.* 35:852–860 (1982).

Sharma and Schimke, "Preparations of Electro–Competent *E. coli* Using Salt–Free Growth Medium," *BioTechn.* 20:42–44 (1996).

Shaw, "Chloramphenicol acetyltransferase from chloramphenicol–resistant bacteria," in *Methods in Enzymology*, J.H. Hushs (ed.), Academic Press, New York, pp. 737–775 (1982).

Shewen and Wilkie, "Cytotoxin of *Pasteurella haemolytica* Acting on Bovine Leukocytes," *Infect. Immun.* 35:91–94 (1982).

Shewen and Wilkie, "Vaccination of Calves with Leukotoxic Culture Supernatant from *Pasteurella haemolytica,*" *Can. J. Vet. Res.* 52:30–36 (1988).

Shewen and Wilkie, "Evidence for the *Pasteurella haemolytica* cytotoxin as a product of actively growing bacteria," *Amer. J. Vet. Res.* 46:1212–1214 (1985).

Strathdee and Lo, "Cloning, Nucleotide Sequence, and Characterization of Genes Encoding the Secretion Function of the *Pasteurella haemolytica* Leukotoxin Determinant," *J. Bacteriol.* 171(2):916–928 (1989).

Strathdee et al., "Extensive Homology between the Leukotoxin of *Pasteurella haemolytica* A1 and the Alpha–Hemolysin of *Escherichia coli,*" *Infect. Immun.* 55:3233–3236 (1987).

Tatum et al., "Molecular Gene Cloning and Nucleotide Sequencing and Construction of an aroA Mutant of *Pasteurella haemolytica* Serotype A1," *Appl Environ. Microbiol.* 60:2011–2016 (1994).

Thomas, "Hybridization of denatured RNA and small DNA fragments transferred to nitrocellulose," *Proc. Natl. Acad. Sci.* 77:5201–5205 (1980).

Trieu–Cuot et al., "An integrative vector expoliting the transposition properties of the Tn1545 for insertional mutagenesis and cloning of genes from Gram–positive bacteria," *Gene* 106:21–27 (1991).

Wagner et al., "Active and Inactive Forms of Hemolysin (HlyA) from *Escherichia coli,*" *Mol. Microbiol.* 369:39–46 (1988).

Waurzyniak et al., "Enhancement of *Pasteurella haemolytica* leukotoxic activity by bovine serum albumin," *Amer. J. Vet. Res.* 55:1267–1274 (1994).

Weisemann et al., "Measurement of In Vivo Expression of the recA Gene of *Escherichia coli* by Using lacZ Gene Fusions," *J. Bacteriol.* 160:112–121 (1984).

Welch, "Pore–forming cytolysins of Gram–negative bacteria," *Mol. Microbiol.* 5:521–528 (1991).

West et al., "Construction of an *Actinobacillus pleuropneumoniae*–*Escherichia coli* shuttle vectors: expression of antibiotic–resistance genes," *Gene* 160:81–86 (1995).

Wood and Lainson, "A native plasmid of *Pasteurella haemolytica* serotype A1:DNA sequence analysis and investigation of its potential as a vector," *Res. Vet. Sci.* 58:163–168 (1995).

Wright et al., "Characterization of a *Pasteurella haemolytica* Plasmid and Its Use to Express Recombinant Proteins in *P. Multocida,*" *Plasmid* 37:65–79 (1997).

Yates, "A Review of Infectious Bovine Rhinotracheitis, Shipping Fever Pneumonia and Viral–Bacterial Synergism in Respiratory Disease of Cattle," *Can. J. Comp. Med.* 46:225–263 (1982).

Berrier, *Animal Sanitation and Disease Prevention,* Second Edition, Kendall/Hunt Publishing Company, Dubuque, Iowa, pp. 192, 210 (1977).

Chang et al., "Pneumonic pasteurellosis: Examination of typable and untypable *Pasteurella haemolytica* strains for leukotoxin production, plasmid content, and antimicrobial susceptibility," *Am. J. Vet. Res.* 48(3):378–384 (1987).

Chidambaram et al., "Isolation of *Pasteurella haemolytica* Leukotoxin Mutants," *Infection and Immunity* 63(3):1027–1032 (1995).

Collins, "Pasteurella, Yersinia, and Francisella," *Medical Microbiology,* Fourth Edition, (ed. Baron), The University of Texas Medical Branch at Galveston, TX, pp. 381–386.

Hackett et al., *J. Biol. Chem.* 270(35):20250–20253 (1995).

Holmes et al., "Unusual Gram–Negative Bacteria, Including Capnocytophaga, Eikenella, Pasteurella, and Streptobacillus," *Manual of Clinical Microbiology,* Sixth Ed., (ed. Murray et al.), ASM Press, Washington, D.C., pp. 499–508 (1995).

*Microbiology,* Fourth Edition, (ed. Davis et al.), J.B. Lippincott Company, Philadelphia, pp. 609–610 (1990).

Murphy et al., "Restriction Endonuclease Analysis and Ribotyping Differentiate *Pasteurella haemolytica* Serotype A1 Isolates from Cattle within a Feedlot," *J. Clin. Microbiol.* 31(9):2303–2308 (1993).

"Pasteurella, Actinobacillus, Streptobacillus and Calymmatobacterium," *Zinsser Microbiology,* Eighteenth Edition, Chapter 42, (ed. Joklik et al.), Appleton–Century–Crofts, Norwalk, Connecticut, pp. 657–659 (1984).

Schwarz et al., "Detection and Interspecies–Transformation of a β–Lactamase–Encoding Plasmid from Pasteurella haemolytica," *Zbl. Bakt. Hyg. A* 270:462–469 (1989).

*The Merck Veterinary Manual,* Fifth Ed., (ed. Siegmund et al.), Merck & Co., Inc., Rahway, NJ, pp. 910–913 (1979).

Fedorova and Highlander, "Plasmids for heterologous expression in *Pasteurella haemolytica,*" *Gene* 186:207–211 (1997).

* cited by examiner

FIG. 12

| FIG. 12A |
| FIG. 12B |
| FIG. 12C |

FIG. 12A

```
      XmnI
  1   GAAAGCCTTCTCCATTCCTCCATCATCAAAATGTTTGCTTTGCCATCACTTCATCATAATCAAAATAGAGACTATACTCCCGCCC
        F  G  E  E  M  E  E  D  D  F  A  A  D  L  N  N  A  K  A  M  V  E  D  Y  D  F  Y  L  S  Y  E  R  G

101   TTCAAACACACATTCATAATGATTCGGAAATGCGGCTCGACACTTCTCTATTTCAGGCGAAATAGGGGCTAACTGGCTAGGATTTTCCGTTATTCGGCA
        E  F  V  C  E  Y  H  N  P  F  A  A  R  C  K  E  I  E  A  F  I  P  A  L  Q  S  P  N  E  T  I  E  A
                                                                                                        -35
201   TTCAACCAACGAGCAAACGCCTCGTGATCCATCGAACATTTGCCACCCCCGTGAATACTATGGGTAAATTGATATTCATACCGATTCCCTTGAA
        N  L  W  R  A  F  A  E  H  D  M  S  C  K  A  V  V  G  H  I  S  H  T  F  Q  Y  E  M  <orf1
                                         DraIII                                               SH130

301   TTGGTCTGTTGTTGGCTAGAATAATACAGGTTATTTTTAGTATTGATACATCAAAAGGAACTACTATGCCAAACGCTAATTTTAAATGTTATCAACTCCTGATTACCC
        --->                                                                 SH130                                -10

401   AGAAATCTGCTAGAATAATACAGGTTATTTTTAGTATTGATACATCAAAAGGAACTACTATGCCAAACGCACAGCACAGCACAGCACAGCACAGCACA                    (14)
                                                          a1xA-hsdM> M  P  N  S  T  A  Q  H  S  T  A  Q  H  S 501   GCACAGCACAGCACAGCACAGCACAGCACAGCACAGCACAGCACAGCACAGCACAGCACAGCACAGCACAGCACAGCACAGCACAGCACAGCACA                       (47)
         T  A  Q  H  S  T  A  Q  H  S  T  A  Q  H  S  T  A  Q  H  S  T  A  Q  H  S  T  A  Q
                                                                                                DraIII 601   GCACAGCACAGCACAGCACAGCACAGCACAGCACAGCACAGCACAGCACAGCACAGCACAGCGTGATCTCAAGCTCTGACACAAGTCAAGCCTTT                       (80)
         H  S  T  A  Q  H  S  T  A  Q  H  S  T  A  Q  H  S  T  A  Q  H  S  V  I  S  T  S  D  T  S  Q  A  F
              SH131
```

FIG. 12B

```
701  TTAAACGAACTGACCAAACCCTCTGGACTGCCGCGACAAACTGCGTAAAAACCTGGATGCCGCCAACTACAAACATCGTTCTTGGCTTTATCTTCC  (114)
      L  N  E  L  D  Q  T  L  W  T  A  A  D  K  L  R  K  N  L  D  A  A  N  Y  K  H  I  V  L  G  F  I  F  L

801  TAAAATACATCTCCGACAGCTTTACCGATTTCCAAGCCAAGCTAAAAACCAGCTTACCACCCCCGAAAGCGAACTCTATCTTGACCCTGCACTATTGA  (147)
      K  Y  I  S  D  S  F  T  D  F  Q  A  K  L  K  T  Q  L  T  T  P  E  S  E  L  Y  L  D  P  A  L  F  D

901  CGAACAAGAATTTAGCCAAATCTTGCCGAAGAGTTGGAACAGAGAATTACTACGCCGCTGAAAACATCTTTGGGTGCCGGAGCAAGCCCGCTGGGAC  (180)
      E  Q  E  F  S  Q  I  L  A  E  E  L  E  Q  R  D  Y  Y  A  A  E  N  I  F  W  V  P  E  Q  A  R  W  D

1001 AACATCAAATCATTAAGCAAACTCAATCTTGGCGATGAATTGCCTTGGGGAGACAAATTTAAAGGTGTCAGCCGCTTGATTGATGCCTTTGAAGCCA  (214)
      N  I  K  S  L  S  K  L  N  L  G  D  E  L  P  W  G  D  K  F  K  G  V  S  R  L  I  D  D  A  F  E  A  I

1101 TCGAACGGGAAAACCCCAAACTCAAAGGGCGTACTCCAAGGCGCTCAATGGCACGTCTGCATCTCGCAAGCCAAAGACATTTTAGGGCGTTGACGTCTGTTCTCACG  (247)
      E  R  E  N  P  K  L  K  G  V  L  Q  R  I  A  G  F  G  V  P  D  E  M  L  T  G  L  I  D  L  F  S  R
                                                                                                    XmnI

1201 CACCCAATTTCACCCAGCCAGATGCACAATGGGCGTCAATACTTCACGCTCGAACATCATCGTTGATTGTTGAAATGCTGGAACCCTATTCAGGGCGGATTACGACC  (280)
      T  N  F  T  Q  P  M  H  N  G  E  P  V  H  L  Q  A  K  D  I  L  G  H  V  Y  E  Y  F  L  G  Q  F  A

1301 CTTGCCGAAGGCAAAAAGGCGGTCAATACTTCACGCTCGAACATCATCGTTGATTGTTGAAATGCTGGAACCCTATTCAGGGCGGATTACGACC  (314)
      L  A  E  G  K  K  G  G  Q  Y  F  T  P  K  S  I  V  T  L  I  V  E  M  L  E  P  Y  S  G  R  I  Y  D  P

1401 CAGCTATGGGCAGCGGCGGCGCTTTTTGTGCAAGCTGACGCGATTCGTGTATTCCCTTTGACTTTGGCGACAAGCCCGAAGATACCCTACTAAACCCTTTGCAC  (347)
      A  M  G  S  G  G  F  F  V  Q  A  D  R  F  I  Q  A  H  A  G  N  R  N  A  I  S  V  Y  G  Q  E  S  N

1501 CTCCACCACTCGCAAACTGGCGGTGATGAATATGGCGATTCGTGTATTCCCTTTGACTTTGGCGACAAGCCCGAAGATACCCTACTAAACCCTTTGCAC  (380)
      S  T  T  R  K  L  A  V  M  N  M  A  I  R  G  I  P  F  D  F  G  D  K  P  E  D  T  L  N  P  L  H

1601 ATCGACAAAAAAATGGATGTTGTGATGGCAAATCCGCCCTTTAACCAAAAAGAGTGTGAATGAAAGAGTGTGAATGAAAGAACTAGCAAAGCTAGCAAGAATCCGCATCCACGCTGGGCATACGGCA  (414)
      I  D  K  K  M  D  V  V  M  A  N  P  P  F  N  Q  K  E  W  W  N  E  S  L  A  N  D  P  R  W  A  Y  G  T
```

```
1701 CACCGCCGCAAGGCAACGCCAACTTTGCGTTGCAACATATGATTTACCACCTCTCCCCCAAAGGCAAAATGGCACTCCTGCCTCGCAACGGCTCAAT  (447)
      P  P  Q  G  N  A  N  F  A  W  L  Q  H  M  I  Y  H  L  S  P  K  G  K  M  A  L  L  P  R  N  G  S  M

1801 GAGCAGCCAAACTTCAGGCGAAGGCGACATTCGAAAAAATCGTGCAAGCTGACCTTGTCGAAGCGATGATTGCCCTGCCTAATCAGTATTCACCAAC  (480)
      S  S  Q  T  S  G  E  G  D  I  R  K  N  I  V  Q  A  D  L  V  E  A  M  I  A  L  P  N  Q  L  F  T  N

1901 ACCCAAATCCCTGCCTGCATTTGGATTATCAATAAAGCCAAAAGCCAGAAAAGTGAAGTGCTGTTTATCAACGCCACCCAAATAGGCTACCTGAAGGACC  (514)
      T  Q  I  P  A  C  I  W  I  I  N  K  A  K  A  R  K  G  E  V  L  F  I  N  A  T  Q  I  G  Y  L  K  D  R

2001 GCGTCTTGCGTGATTTTACCGCTGATGACATCGCCAAAATCAGCGACACTTACCACAACAGAACGGCTACGAAAATATCCCTGCGTTTG  (547)
      V  L  R  D  F  T  A  D  D  I  A  K  I  S  D  T  Y  H  N  W  Q  K  Q  N  G  Y  E  N  I  P  A  F  C

2101 TTATTGTGCCACGCTGGACGAAATCGCCAAAAAACGATTTTGTGCTGACAAGATATGTCGGTGCGTACAAGAAGAAATGACGGCTGCGGTTT  (580)
      Y  C  A  T  L  D  E  I  A  K  N  D  F  V  L  T  A  G  R  Y  V  G  A  V  Q  E  E  N  D  G  V  R  F

2201 GCAGAAAAAATGCAGGAATTGACGGCTTATTGAATGAACAATTAAACAAGGGCGGGAATTAAACAAGGGGGTTGGGAT  (614)
      A  E  K  M  Q  E  L  T  A  L  L  N  E  Q  F  K  Q  G  R  E  L  E  Q  Q  I  A  E  N  L  K  G  L  G  Y

2301 GCAGAAAAAATGCAGGAATTGACGGCTTATTGAATGAACAATTAAACAAGGGCGGGAGAATTAAACAAGACTAAAAAAGAAAACTATATTTCGACAGATA  (616)
hsdS> ATGGCATTTAATCAGTATGTATTTCAGATATGTTGAATTAATATCCGAAAAAAATCAAAGACTAAAAAAGAAAACTATATTTCGACAGATA
      G  I  *
      M  A  F  N  Q  Y  V  F  S  D  I  V  E  L  I  S  E  K  I  K  D  L  K  K  E  N  Y  I  S  T  D  N
                                                                      XmnI
2401 ATATGCTGCCTAATTTGGTGGAATAACACTTGCTGAAACCTTC  2311
      M  L  P  N  F  G  G  I  T  L  A  E  N  L
```

FIG. 12C

PASTEURELLA HAEMOLYTICA VACCINE

This is a continuation of application(s) Ser. No. 08/834,455 filed on Apr. 15, 1997, now abandoned.

FIELD OF THE INVENTION

The present invention is directed to compositions and methods for the prevention of disease due to *P. haemolytica*. In particular, the present invention provides *P. haemolytica* strains that produce inactive leukotoxin.

BACKGROUND OF THE INVENTION

Bovine respiratory disease (BRD) encompasses a variety of syndromes that cause serious economic losses. Included within this group of syndromes are diseases associated with Pasteurella species, most commonly *P. haemolytica*, the major etiologic agent bovine pneumonic pasteurellosis ("shipping fever")(See e.g., Yates Can. J. Comp. Med., 46:225–263 [1982]; Confer et al., J. Amer. Vet. Med. Assoc., 193:1308–1316 [1988]; and Martin et al., Can. J. Comp. Med., 44:1–10 [1980], for reviews of BRD and pneumonic pasteurellosis). Shipping fever is the greatest source of economic loss in feedlot cattle due to the significant mortality rate, as well as the unthriftiness and decreased rate of gain of animals that survive the disease (See e.g., Haynes, *Keeping Livestock Healthy*, Garden Way Publishing, Charlotte, Va. [1978], pp.145–148).

Shipping fever is common in North America, the United Kingdom, and continental Europe. Although cattle of all ages and breeds are susceptible, those most commonly affected are young beef cattle that have been recently (i.e., within 3 weeks) introduced into feedlots. However, it can be equally disastrous in dairy herds. Risk factors for disease include mixing of calves from different origins or ages (clustering of cases often occurs among particular truckloads and/or pens of cattle), stresses associated with transportation, feed shortages, water deprivation, and vaccination upon arrival at feedlots. Other risk factors include communal summer grazing, drafty, humid indoor housing, and close housing of cattle in communal sales and rail yards. The major cause of loss is by death, with the case fatality rate of 5–10%, and a herd morbidity rate of up to 35% (See, Blood, *Pocket Companion to Veterinary Medicine*, Baillière Tindall, London [1994], pp. 309–310). Peak losses occur in cattle 6 months to 2 years of age. Other losses include the lengthened stay in fattening units required by affected cattle that survive the disease. Pasteurellosis represents losses to the American cattle industry of more than 500 million dollars annually (McMillan, in *Bovine Respiratory Disease: A Symposium*, R. W. Loan (ed.), [1984],. p. 64).

Transmission of pasteurellosis is usually accomplished via contact with or aerosolization of nasal and ocular discharges from clinical cases, although carrier animals may also contribute to spread of disease, as healthy animals often carry the organisms in their upper respiratory tracts. In addition, the organisms appear to increase in virulence as the disease becomes active in animals under stress, and increases to the point where animals not under stress also succumb to the disease.

Clinical findings include rapid onset, depression, rapid, shallow breathing, increased loudness of breath sounds that increase in area over time, progression to crackles and wheezing, dyspnea, fever, cough, anorexia, gaunt abdomen, mucopurulent nasal discharge, crusty nose, and ocular discharge. In addition, pleuritic friction sounds are present early in disease, grunting with each expiration of breath is observed later in disease. As the disease progresses, fluid, cellular debris, and pus accumulate in the small air passages. Consolidation of lung tissue may become sufficiently severe that cyanosis results. Sequelae include chronic bronchopneumonia, pleural adhesions, lung abscess, chronic pleurisy, pericarditis, and congestive heart failure. At necropsy, marked consolidation of anteroventral parts of the lung with serofibrinous exudate accumulation in the interlobular spaces is observed, as well as catarrhal bronchitis, bronchiolitis, serofibrinous pleurisy with accumulation of large quantities of pleural fluid, and fibrinous pericarditis.

Shipping fever is associated with various organisms, including *P. haemolytica, P. multocida*, bovine herpes virus 1, parainfluenza-3, bovine respiratory syncytial virus, and Mycoplasma. Exposure to stress, in combination with infection by various viruses appears to facilitate the development of pneumonic pasteurellosis, with *P. haemolytica* infection resulting in the development of fibrinous pneumonia. Although it appears to have a multi-factorial etiology, methods for prevention and treatment of shipping fever has focused on *P. haemolytica. P. multocida* is also sometimes associated with shipping fever, although it is associated with bronchopneumonia with little fibrinous exudate. *P. haemolytica* and *P. multocida* are responsible for numerous diseases of veterinary and medical importance. For example, in addition to shipping fever, *P. haemolytica* is also associated with other economically important diseases, including ovine and caprine pasteurellosis, horse, donkey and mule meningoencephalitis. *P. multocida* is associated with calf and yearling meningoencephalitis, lamb lymphadenitis, horse and donkey septicemia, bovine septicemic pasteurellosis (hemorrhagic septicemia, barbone), swine pasteurellosis, porcine septicemic pasteurellosis, and fowl cholera. Human disease with these organisms usually occurs in infected bite wounds, as many animals carry Pasteurella as normal flora in their oral cavities. Thus, these organisms are of importance in the feedlot, as well as other settings.

Treatment of shipping fever involves administration of oxytetracycline, trimethoprim-sulfadoxine, penicillin or tilmicosin, although the response in animals with complicated etiologies or late disease is poor. Complete failure to respond sometimes occurs in animals with lung abscesses, bronchiectasis, pleurisy, and other, non-bacterial causes. Chemoprophylaxis is sometimes practiced by mass medication of all animals on arrival at the feedlot. However, mass medication (e.g., in the feed), while potentially reducing mortality, has little effect on morbidity, and the number of cases may actually increase due to relaxed disease surveillance. Routine prophylactic feeding of broad-spectrum antimicrobials to all cattle housed in feedlots has resulted in the development of resistance to many antimicrobials, making the disease difficult to treat. Furthermore, this use of broad-spectrum antimicrobials may result in the development of resistance in organisms of veterinary and/or medical importance, other than *P. haemolytica*.

Vaccination is commonly used in an attempt to prevent disease. However, the results have been marginal. Indeed, vaccination on arrival of animals to the feedlot with modified live vaccine often increases the mortality rate (See e.g., Blood, supra; and Martin et al., Can. J. Comp. Med., 44:1–10 [1980]). These observations have led to numerous investigations into development of vaccines to prevent disease due to *P. haemolytica*. Previous vaccines utilized live or heat-killed whole cell preparations of mixed serotypes (See e.g., U.S. Pat. Nos. 4,328,210, 4,171,354, 3,328,352, 4,167,560, and 4,346,074). Other vaccine preparations have included crude supernatant extracts from *P. haemolytica* cultures, as well as capsular extracts, and saline extracted antigens (See e.g., Shewen and Wilkie, Can. J. Vet Res., 52:30–36 [1988]; Donachie et al., J. Gen. Microbiol., 130:1209–1216 [1984]; Lessley et al., Vet. Immunol, Immunopathol., 10:279–296 [1985]; and U.S. Pat. No. 4,346,074). However, the results obtained with these preparations have been variable.

While other potential factors are involved in the pathogenesis of shipping fever (e.g., lipopolysaccharide, polysaccharide capsule, fimbriae, glycoprotease, neuraminidase, a serotype-specific antigen, and outer membrane proteins), leukotoxin is considered to be the primary virulence factor of *P. haemolytica* (See, Petras et al., Infect. Immun., 63:1033–1039 [1995]; Shewen and Wilkie, Infect. Immun., 35:91–94 [1982]; and Confer et al., Can. J. Vet. Res., 54:S48–S52 [1990]). Thus, other vaccines have been developed, including the use of purified leukotoxin harvested from actively growing *P. haemolytica* cultures (See e.g., Gentry et al., Vet. Immunol., Immunopathol., 9:239–250 [1985]; and Shewen and Wilkie, Infect. Immun., 55:3233–3236 [1987]). Nonetheless, there remains a need in the art for a vaccine preparation that provides immunity, without the pathology associated with the administration of previous vaccines, and avoiding the problems associated with the use of organisms carrying antimicrobial resistance genes. Indeed, protection against pasteurellosis is of great economic importance to the beef industry, as well as agriculture in general.

SUMMARY OF THE INVENTION

The present invention is directed to compositions and methods for the prevention of disease due to *P. haemolytica*. In particular, the present invention provides *P. haemolytica* strains that produce inactive leukotoxin. The present invention further provides methods and compositions for the over-expression of inactive leukotoxin. It is contemplated that this inactive leukotoxin will find widespread use as a component in a vaccine preparation, as well as in the development of improved methods to prevent and treat pasteurellosis. The present invention further provides methods and compositions for expression of inactive or active leukotoxin that do not incorporate antimicrobial resistance genes.

In one embodiment, the present invention provides a host cell containing a recombinant expression vector, said vector encoding a protein comprising at least a portion of *Pasteurella haemolytica* leukotoxin, and a non-polar promoterless cassette. In one preferred embodiment, the recombinant expression vector contains a non-polar promoterless cassette that comprises the chloramphenicol acetyl transferase operon. In a particularly preferred embodiment, the non-polar promoterless cassette is inserted within the lktC gene. The present invention also provides a host cell containing a recombinant expression vector such that the lktC gene is inactivated. In one preferred embodiment, the vector is pNF2237. It is contemplated that various host cells will be utilized with the present invention. In one preferred embodiment, the host cells comprise Gram-negative organisms. In one particularly preferred embodiment, the cells are of the genus Pasteurella. In an alternate preferred embodiment, the host cell is *Pasteurella haemolytica*. In another preferred embodiment, the host cell is *Escherichia coli*.

The present invention also provides host cells containing multiple expression vectors. In one embodiment, the host cell contains a first expression vector and a second expression vector, wherein said first expression vector comprises a native plasmid of *P. haemolytica*, and said first and second expression vectors are incompatible. In one preferred embodiment, the first expression vector is pYFC1. In an alternative preferred embodiment, the second expression vector is pNF2176. In a particularly preferred embodiment, the host cell contains pYFC1 and pNF2176. It is contemplated that various host cells will be used in the present invention. In one preferred embodiment, the host cells comprise Gram-negative organisms. In one particularly preferred embodiment, the cells are of the genus Pasteurella. In an alternate preferred embodiment, the host cell is *Pasteurella haemolytica*. In another preferred embodiment, the host cell is *Escherichia coli*.

The present invention also provides an expression vector comprising a leukotoxin promoter and at least a portion of lktC. In a preferred embodiment, the expression vector further comprises an activator of leukotoxin expression. In embodiment, the activator comprises AlxA. In another embodiment, the activator further comprises hsdM. In an further alternative embodiment, the activator has the sequence of FIG. 12.

The present invention also provides an expression vector capable of replication in *Pasteurella haemolytica* and *Escherichia coli*, wherein said expression vector comprises an antimicrobial resistance gene and a multiple cloning site module. In a preferred embodiment, the multiple cloning site module comprises a chloramphenicol resistance gene. In one particularly preferred embodiment, the vector is pNF2200. In an alternative preferred embodiment, the vector is pNF2211. In yet a further embodiment, the multiple cloning site module comprises the recognition sequences for the following restriction enzymes EcoRI, MluI, SnaI, ApaI, KpnI, SmaI, XmaI, AvaI, BamHI, XhoII, XbaI, SalI, PstI, SphI. In one embodiment, the multiple cloning site module is from pTZ1RJL1. In one preferred embodiment, the antimicrobial resistance gene comprises *Pasteurella haemolytica* ROB-1 β-lactamase gene. In yet another embodiment, the expression vector comprises SEQ ID NO:1. In a further embodiment, the antimicrobial resistance gene comprises the Tn903 kanamycin resistance element. In an alternative embodiment, the expression vector comprises SEQ ID NO:2. The present invention also provides an expression vector comprising the nucleic acid sequence as set forth in SEQ ID NO:3.

The present invention also provides vaccines for the prevention of *Pasteurella haemolytica* disease, including but not limited to shipping fever. In one embodiment, the present invention provides a vaccine composition comprising a therapeutically effective amount of recombinant *Pasteurella haemolytica* organism, wherein said recombinant *Pasteurella haemolytica* organism expresses inactive leukotoxin. In an alternative embodiment, the vaccine further comprises diluent. In another embodiment, the vaccine further comprises at least one compound selected from the group consisting of excipients and adjuvants.

In a preferred embodiment, the vaccine composition of comprises recombinant *Pasteurella haemolytica* with an inactivated lktC gene. In yet another embodiment, the recombinant *Pasteurella haemolytica* comprises an lktC::cat operon fusion. In a particularly preferred embodiment, the expression of inactive leukotoxin is stably maintained.

In yet another embodiment of the vaccine, the recombinant *Pasteurella haemolytica* contains an activator for expression of said inactive leukotoxin. In one embodiment, the activator is AlxA. In yet another embodiment, the recombinant *Pasteurella haemolytica* further comprises a strong leukotoxin promoter. In a particularly preferred embodiment, the vaccine composition compr Development of electroporation and conjugation techniques for *P. haemolytica* (Craig et al., J. Gen. Microbiol., 135: 2885–2890 [1989]) made it possible to perform allelic exchange by the commonly used methodology of Gutterson and Koshland (Gutterson, and Koshland, Proc. Natl. Acad. Sci. U.S.A 80: 4894–4988 [1983]). This method was based on strong positive selection for mutations and involved use of a suicide plasmid that carried the gene of interest insertionally inactivated with a selective marker. However, only three different chromosomal loci of *P. haemolytica* have been inactivated to date (Homchampa et al., Vet. Microbiol., 42: 35–44 [1994]; Murphy and Whitworth, Gene 148: 101–105 [1994]; Murphy et al., Infect. Immun., 63: 3209–3212 [1995]; and Tatum et al., Appl. Environ. Microbiol. 60: 2011–2016 [1994]), and all were inactivated at very low frequency. The presence of stringent restriction systems (Briggs et al., Appl. Environ. Microbiol., 60: 2006–2010 [1994]; and Highlander and Garza, Gene 178: 89–96 [1996]) and a low frequency of homologous recombination with respect to illegitimate recombination (Murphy and Whitworth, Gene 148: 101–105 [1994]) have made the positive selection method cumbersome and inefficient in *P. haemolytica*, especially in the absence of a simple phenotypic screen. These problems necessitated the development of more effective methods for gene replacement in *P. haemolytica*.

Thus, despite advances in allelic exchange technology in other organisms, working cloning vectors were not available for *P. haemolytica* until the development of the present invention. The difficulties in creating a genetic system have been largely due to a lack of expressed selective markers and broad-host-range plasmids that can be used in this organism. For example, a small $Ap^R$ plasmid of *P. haemolytica* was examined as a potential shuttle vector (Azad et al., Gene 145: 81–85 [1994]; and Wood et al., Res. Vet. Sci., 58: 163–168 [1995]), but the plasmid was difficult to manipulate. Expression of type I and II $Cm^R$ genes (i.e., cat) also has been reported in *P. haemolytica* (See, Frey, [1992] supra; Azad et al. [1994] supra; Briggs et al. [1994]; and West et al. [1995], supra). However, resistance levels were low (i.e., 2 μg/ml), and plasmid DNA could not be recovered from the transformants.

In contrast, one embodiment of the present invention provides a set of *P. haemolytica-Escherichia coli* shuttle cloning vectors derived from another native plasmid, pYFC1 (Chang et al., J. DNA Seq. Map., 3: 89–97 [1992]). The vectors of the present invention utilize a variety of antibiotic resistance markers and were used successfully for gene cloning and expression in *P. haemolytica*. In one embodiment, the mutagenic plasmid, carrying the gene of interest insertionally inactivated with a selective marker, was propagated in *P. haemolytica* to allow the recombination to occur. A second incompatible plasmid was then introduced to displace the mutagenic plasmid. This approach employed three different antibiotic resistance genes: a vector marker, a mutagenic marker, and a marker for the second incompatible plasmid. The mutagenic marker used was a promoterless chloramphenicol acetyl transferase gene (cat) carried on a nonpolar cassette that confers $Cm^R$ only when transcribed from an upstream promoter. This cassette was chosen for this embodiment as the cat gene was found to be expressed in *P. haemolytica* when transcribed by *P. haemolytical* promoters; insertion of the cassette within an operon did not affect expression of downstream genes; chloramphenicol acetyl transferase (CAT) is a convenient reporter enzyme for measuring gene expression in operon and protein fusions; and most *P. haemolytica* strains are $Cm^S$ and do not exhibit detectable spontaneous resistance (See e.g., Diker et al., Vet Rec., 134:597–598 [1994]).

Thus, in one embodiment of the present invention, a promoterless cat (Tn9) cassette from pSLI was used as a reporter gene to enhance cat expression and demonstrate the utility of plasmids pNF2176 and pNF2214 (See, SEQ ID NOS:1 and 2, respectively for the DNA sequences of these vectors) as expression vectors. Plasmid pNF2176 carries the *P. haemolytica* ROB-1 β-lactamase gene (blaP, $Ap^R$) and pNF2214 carries the Tn903 aph3 kanamycin resistance ($Km^R$) element. The cat cassette was cloned into the MCS of both pNF2176 and pNF2214 to create pNF2200 and pNF2211, respectively (See, FIG. 1). In *P. haemolytica*, pNF2200 conferred $Cm^R$ at 10 μg/ml, a level of resistance that is five times higher than that previously reported. Of particular use is the fact that both pNF2214 ($Km^R$) and pNF2176 ($Ap^R$) carry MCSs, and will replicate in both *P. haemolytica* and *E. coli*. In addition, transcription of cloned genes on pNF2176 may be driven by the sulfonamide gene promoter ($P_{sulII}$).

In an alternative embodiment, the present invention provides a promoter-probe vector for *P. haemolytica*, pNF2283 (See, SEQ ID NO:5 for the DNA sequence of this vector), which carries an MCS and uses cat as a reporter gene. This plasmid can be transferred from *E. coli* to *P. haemolytica* at an efficiency of approximately 100 cfu/μg. A less preferred alternative promoter-probe vector, pNF2211, may also be used, although its transfer efficiency is only approximately 10 cfu/μg DNA.

Allelic Exchange in *P. haemolytica*

Development of the shuttle vectors described above allowed the development of another embodiment of the present invention, namely positive-negative selection approaches for allelic exchange in *P. haemolytica* using two incompatible, non-suicide plasmids. This method is in contrast to the strategy for allelic exchange commonly used that is based on strong positive selection and employs mutagenic suicide plasmids that cannot replicate in the targeted recipient. However, the technique using suicide plasmids has proven to be inefficient in *P. haemolytica* because of stringent restriction-modification systems, low frequency of transformation, and potentially rare homologous recombination. In addition, without phenotypic selection, this method is especially cumbersome and involves screening thousands of colonies by colony hybridization and Southern hybridization to recover rare double recombinants (See, Murphy and Whitworth, Gene 148: 101–105 [1994]; and Murphy et al., Infect. Immun., 63: 3209–3212 [1995]).

Since *P. haemolytica* lacks the sophisticated and flexible genetic systems available for other organisms, non-suicide plasmids were chosen for the development of the present invention. In particular, methods were developed to specifically inactivate the lktC gene of *P. haemolytica*. A plasmid carrying the gene insertionally inactivated with cat, was co-established with an incompatible replicon. Plasmid segregation was then used to detect clones where cat was rescued by homologous recombination at the leukotoxin locus.

Insertional inactivation of the lktC gene was found to abrogate cytotoxicity. The mutant strain was neither leukotoxic nor hemolytic, but produced and secreted proLktA that was still antigenic. Expression of the lktC gene in trans restored the wild-type phenotype, providing direct evidence that LktC is required for activation of *P. haemolytica* proleukotoxin and that leukotoxin is responsible for the hemolytic and leukotoxic effects of the organism. This was consistent with previous results reported for *E. coli* hemolysin and *P. haemolytica* leukotoxin in *E. coli* (Forestier and Welch, Infect. Immun., 58: 828–832 [1990]; and Highlander et al., J. Bacteriol., 172: 2343–2350 [1990]). Nonetheless, the present invention provides the first methods for successful genetic complementation in *P. haemolytica*. Furthermore, expression and secretion of the active leukotoxin by a complemented mutant strain also indicated that the cat cassette had indeed created a nonpolar insertion. In addition, insertion of the cat gene at the leukotoxin locus created an operon fusion that is useful for quantitation of leukotoxin transcription in *P. haemolytica*.

A previously reported LktC⁻, LktA⁻ strain constructed earlier by marker exchange at the leukotoxin locus of *P. haemolytica*, was also not cytotoxic, because it did not produce nor secrete LktA (Murphy et al., Infect. Immun., 63:3209–3212 [1995]). However, the lktC mutant produced according to the present invention is significantly different, in that it still produces the inactive leukotoxin plus other wild-type antigens, but lacks cytotoxicity. The inactive leukotoxin of one embodiment of the present invention reacted efficiently with leukotoxin-neutralizing antibodies. Thus, it is contemplated that inactive leukotoxin produced using the methods of the present invention will elicit neutralizing immune responses in cattle (i.e., the $LktC^-$ strain, producing genetically toxoided leukotoxin, will find use for vaccine preparations and development).

*P. haemolytica* Leukotoxin Promoter Activity

Generation of the chromosomal fusion to cat allowed assessment of leukotoxin promoter activity in *P. haemolytica*. Since the *P. haemolytica* leukotoxin genes are poorly expressed in *E. coli*, it was suggested that Pasteurella-specific transcriptional factors are required for effective expression. Several putative regulators of *P. haemolytica* leukotoxin expression have been identified using an *E. coli* trans-complementation system based on lktC::lacZ gene fusions (See, Highlander et al., Infect. Immun., 61: 3942–3951 [1993]). However, until the development of present invention, methods have not be available to assess their functions and activities in *P. haemolytica*. This was accomplished by using the lktC::cat gene fusion to monitor leukotoxin expression in *P. haemolytica* by measuring the level of acetyl-chloramphenicol produced in cell extracts. Leukotoxin expression reached a maximum in early logarithmic phase and declined later as the cells entered late logarithmic and stationary phase. The early to late-logarithmic expression ratio for the chromosomal fusion was about 2.5-fold while the plasmid-borne fusion ratio was 6.5-fold. Although increased leukotoxin expression in early logarithmic phase has been observed in Northern blots (Strathdee and Lo, J.Bacteriol., 171:5955–5962 [1989]), the results obtained using the present invention also revealed a decline in expression as the cells leave early logarithmic phase. Similar kinetics, with delayed appearance of the peak, were observed for secretion of *P. haemolytica* leukotoxin (Waurzyniak et al., Amer. J. Vet. Res., 55: 1267–127 [1994]) and *E. coli* hemolysin (Wagner et al., Mol. Microbiol., 369: 39–46 [1988]) into cell supernatants. However, this embodiment of the present invention provides the first chromosomal reporter gene fusion useful for monitoring gene expression in *P. haemolytica*.

The embodiments of the present invention directed to allelic exchange in *P. haemolytica* have numerous advantages, including: very high efficiency, because nonsuicide plasmids can be maintained in the target host long enough to ensure double recombination events; only minimal knowledge of the molecular biology of target host and a simple genetic system is required for their use; specific inactivation the gene of interest with the nonpolar selection cassette does not affect expression of downstream genes; and chromosomal fusion to cat provides a reporter to quantitate promoter activity. Thus, it is clear that the present invention provides methods and compositions useful for genetic analyses and vaccine development for *P. haemolytica*. It is further contemplated that the present invention will find use in other members of the Haemophilus-Actinobacillus-Pasteurella (HAP) family of bacteria, as plasmids similar to pYFC1 have been identified in *Actinobacillus pleuropneumonia* (West et al., Gene 160: 81–86 [1995]), *Pasteurella multocida* (Wright et al., Plasmid 37: 65–79 [1997]) and *Haemophilus ducreyi* (Dixon et al., Plasmid 32: 228–232 [1994]).

An Activator of *P. haemolytica* Leukotoxin Transcription

As indicated above, the *P. haemolytica* A1 leukotoxin promoter is poorly expressed in *E. coli*, suggesting that Pasteurella-specific transcriptional factors may be required for its maximal leukotoxin expression, and that leukotoxin expression may be regulated by a system that involves transcriptional activation. Transcriptional activation of leukotoxin is of particular importance due to the observation that virulence of *P. haemolytica* appears become activated when the organism descends into the lungs and results in disease. Thus, it was of interest to determine the mechanisms of transcriptional activation as a means to develop treatment and prevention procedures.

Although it has a near consensus $\sigma^{70}$ −10 region, the leukotoxin promoter, like most other *P. haemolytica* promoters, is very poorly expressed in *E. coli* (See, Highlander and Weinstock [1994], supra). Since plentiful leukotoxin message is observed in *P. haemolytica*, specific activator proteins required for expression are not present in the heterologous host. A similar observation was made when a *Bordetella pertussis* adenylate cyclase (cya) operon fusion was expressed in *E. coli*. In one embodiment, the present invention provides a complementation system in *E. coli* for identification of genes that encode activators of leukotoxin transcription.

Using a leukotoxin (lktC)-β-galactosidase (lacZ) operon fusion as a reporter, a *P. haemolytica* cosmid clone that activates leukotoxin transcription in *E. coli* was isolated The activator locus, called alxA, was mapped and sequenced, and its activity was quantitated by measuring lktC-lacZ expression in *E. coli* when alxA was expressed in trans. The activator gene was identified as part of a continuous open reading frame that includes the hsdM methylase gene of the *P. haemolytica* type I restriction-modification system. In addition to the alxA activator locus, two additional clones have been identified that activate leukotoxin genes expressed in *E. coli*. Crude extracts from cells expressing these clones bind to sequences in UAS sequences in promoter regions. Thus, it is contemplated that additional activator sequences will be identified using the methods of the present invention.

In vitro transcription and translation reactions produced 72, 38 and 31 kD peptides that corresponded to the predicted molecular weight of an AlxA-HsdM precursor and two processed products. Subcloning indicated that only the 5' half of the gene was required for activator function and that the 38 and 31 kD products corresponded to HsdM and AlxA, respectively. *E. coli* extracts containing the activator were capable of binding to a leukotoxin promoter fragment, though no DNA binding motifs were evident in the AlxA sequence. Nevertheless, AlxA possesses a putative leucine-zipper domain and acidic region characteristic of eukaryotic and some prokaryotic transcription factors. Thus, the present invention provides an activator that affects production of leukotoxin by P. haemolytica. It is contemplated that by modifying this activator, non-virulent strains of P. haemolytica will be developed for use as vaccine strains, etc. It is further contemplated that this activator will serve as a target for the development of antimicrobials effective against P. haemolytica. For example, it is contemplated that antimicrobial or antimetabolite (e.g., nucleic acid analogs) compounds will be developed that modify or ameliorate the function of the activator. It is also contemplated that antimicrobial compounds will be developed that impact the production of active leukotoxin downstream from the function of the activator.

Site-Specific Recombination for Vaccine Development

It is also contemplated that site-specific recombination be used in the development of live P. haemolytica vaccines that do not contain antimicrobial resistance genes. This is of particular importance in view of the development of widespread antimicrobial resistance in Pasteurella, as well as in other microorganisms.

It is therefore contemplated that recombinant vaccine strains that do not carry antimicrobial resistance factors will find use in numerous settings, including feedlots, dairies, cow-calf operations, as well as swine, goat, sheep, and horse facilities. Indeed, this represents a further improvement over currently available recombinant leukotoxin production means, as recombinant leukotoxin genes described to date include antimicrobial resistance genes (See e.g., U.S. Pat. Nos. 5,476,657, 5,055,400, 5,536,491, 4,957,739, all of which are herein incorporated by reference). By avoiding the use of antimicrobial resistance genes, organisms expressing the recombinant, inactive leukotoxin may be source strains for vaccines (i.e., modified live vaccines), providing the further advantage of including additional antigens (e.g., cellular antigens) that may stimulate an enhanced immune response in vaccinated animals.

In one embodiment, modules for site-specific recombination of phage λ and transposon Tn1545 (See e.g., Clewell et al., Trends Microbiol., 3:229–236 [1995]; Poyart-Salmeron, Mol. Microbiol., 4:1513–1521 [1990]; and Trieu-Cuot et al., Gene 106:21–27 [1991]) are used. However, it is not intended that the modules be limited to λ and Tn1545. For example, it is intended that the other members of the conjugative transposon family (e.g., Tn916, Tn918, and Tn920) will be used. In alternative embodiments, the lktC gene is inactivated using the phage P1 cre/lox recombination system (See e.g., Gu et al., Cell 73:1155–1164 [1993]; U.S. Pat. No. 4,9595,317; herein incorporated by reference).

The lktC gene was insertionally activated with a non-polar kanamycin resistance cassette (See, Sansonetti et al., Infect. Immun., 35:852–60 [1982], for a description of this kanamycin resistance cassette). This cassette allowed expression of DNA fragments inserted in the P. haemolytica chromosome. In the presence of the λXis and λInt proteins, the resistance gene is excised. This excision is accomplished by the introduction of a helper plasmid (e.g., pNF2176) carrying the λxis and λint genes into the recombinant P. haemolytica cells. Under the control of a P. haemolytica promoter, these genes provide production of λ excisase and integrase which results in the excision of the kanamycin gene from the chromosome, while leaving lktC inactivated by the insertion of λatt. Excision from the chromosome is accomplished by recombination between λattL and λattR, and is dependent upon the action of λXis and λInt proteins. It is also contemplated that site-specific recombination will be used to introduce strong promoters, in particular strong regulated (e.g., LapA, LapC, or LapT promoters) using the methods of the present invention.

Other methods for the development of live vaccine strains that do not contain antimicrobial resistance gene are contemplated, including the use of such markers as sacB, as well as others (e.g., other enzyme systems that allow for ready selection of recombinant organisms suitable for use as vaccine strains in vitro).

From the above, it is clear that the present invention provides methods and compositions for the development and use of vaccines and therapeutics for P. haemolytica disease and invention. In particular, some embodiments provide methods to develop P. haemolytica strains (as well as the strains themselves) that produce large amounts of functionally inactive, but antigenically protective, leukotoxin.

In alternative embodiments, site-directed deletion mutagenesis and gene replacement in P. haemolytica is used to inactivate the chromosomal copy of the post-translational activator of leukotoxin, thereby eliminating the need to treat toxin with formalin or other chemical denaturant that can degrade the antigen. In addition, vaccine strains resulting from these manipulations produce both the toxin and surface antigens required for maximum protection against bovine shipping fever in vivo. It is contemplated that these strains will also be used for the production of large amounts of inactive secreted leukotoxin in vitro. These preparations may then be used for the production of antisera for use in passive immunization regimens as well as in diagnostic immunoassays.

Definitions

To facilitate understanding the invention, a number of terms are defined below.

As used herein, the term "pasteurellosis" refers to any disease condition caused by any member of the genus Pasteurella. In preferred embodiments, the term encompasses diseases caused by P. haemolytica. However, it is intended that the term encompass diseases of veterinary importance including, but not limited to, bovine shipping fever (i.e., pneumonic pasteurellosis of cattle), as well as diseases of ovines and caprines (e.g., pneumonic pasteurellosis of goats and sheep, as well as systemic pasteurellosis, septicemic pasteurellosis, etc.), and equine meningoencephalitis. Also encompassed within this definition are diseases caused by P. multocida, such as lamb lymphadenitis, calf and yearling meningoencephalitis, swine pasteurellosis, snuffles, hemorrhagic septicemia, septic pleuropneumonia, porcine septicemic pasteurellosis, fowl cholera, and various focal infections. Further included within this definition are diseases of humans caused by Pasteurella, including but not limited to infected bites, scratches, and other local wounds, cellulitis, abscesses, lymphadenitis, pyoarthritis, necrotizing synovitis, and osteomyelitis, pneumonia, empyema, lung abscesses, upper respiratory tract infections, bacteremia, peritonitis, and meningitis, cerebellar abscesses, infectious endocarditis, and chorioamnionitis with premature delivery.

As used herein, the term "recombinant organism" refers to an organism that contains recombinant nucleic acid. For example, it is intended that the term encompass P. haemolytica strains (i.e., "recombinant strains") that carry an inactivated gene in the leukotoxin operon. It is also intended to encompass organisms other than P. haemolytica, including, but not limited to members of the HAP family, and E. coli.

As used herein, the term "stably maintained" refers to recombinant organisms that maintain at least one of their recombinant elements through multiple passages (i.e., the element that is desired). For example, it is intended that the term encompass recombinant P. haemolytica cells that are capable of maintaining the expression and/or transcription of inactive leukotoxin through multiple generations (i.e., passages of the strain). It is intended that the recombinant element may be present in the chromosome or maintained as an extrachromosomal element (e.g., as a plasmid). It is not intended that the term be limited to any particular organism or any specific recombinant element.

As used herein, the term "active leukotoxin" refers to the leukotoxin of P. haemolytica of approximately 105 kDa, as measured by SDS-PAGE, that is cytotoxic to ruminant leukocytes. The term "inactive leukotoxin" refers to P. haemolytica leukotoxin secreted from P. haemolytica (i.e., recombinant strains of the organism) that lacks cytotoxicity for ruminant leukocytes and is non-hemolytic, but is recognized by antibodies directed against the active leukotoxin. In preferred embodiments, the lktC gene of the leukotoxin operon is inactivated in strains of P. haemolytica (i.e., recombinant strains) that produce and secrete inactive leukotoxin. The term "proleukotoxin" ("proLktA") refers to the form of the leukotoxin that is present in the P. haemolytica cells prior to its post-translational activation by LktC, and subsequent secretion of the resulting full length leukotoxin mediated by proteins including, but not limited to LktB and LktD.

As used herein, the term "overproducing" is used in reference to the production of leukotoxin polypeptides in a host cell and indicates that the host cell is producing more of the leukotoxin by virtue of the introduction of nucleic acid sequences encoding the activator peptide or strong promoter for leukotoxin polypeptide than would be expressed by said host cell absent the introduction of the nucleic acid sequences. To allow ease of purification of toxin polypeptides produced in a host cell it is preferred that the host cell express or overproduce the leukotoxin polypeptide at a level greater than approximately 20–200 mg/liter of host cell culture. In particularly preferred embodiments, the expressed leukotoxin is inactive.

As used herein, the term "activator" refers to a protein that enhances the level of expression of another protein. For example, the term encompasses the activator associated with increased expression of leukotoxin.

As used herein, the term "fusion protein" refers to a chimeric protein containing the protein of interest (i e., P. haemolytica leukotoxin and/or fragments thereof) joined to an exogenous protein fragment (the fusion partner which consists of a non-toxin protein). The fusion partner may serve various functions, including, but not limited to enhancement of the solubility of the *P. haemolytica* protein as expressed in a host cell, as well as providing an "affinity tag" to allow purification of the recombinant fusion protein from the host cell or culture supernatant, or both. If desired, the exogenous protein fragment may be removed from the protein of interest (i.e., toxin protein or fragments thereof) prior to immunization by a variety of enzymatic or chemical means known to the art.

As used herein, the term "operon fusion" refers to an operon that has been modified by fusion with another nucleic acid sequence. For example, the term encompasses the insertion of the cat gene at the leukotoxin operon (or locus). Thus, the term encompasses recombinant sequences in which the operon is "insertionally inactivated" by the presence of a foreign gene, including but not limited to the cat gene. In preferred embodiments, this insertion occurs in the structural region of the lktC gene (i.e., the cat gene may be said to be "within" the lktC gene), although it may occur in other sites within the leukotoxin operon.

As used herein the term "non-toxin protein" or "non-toxin protein sequence" refers to that portion of a fusion protein which comprises a protein or protein sequence which is not derived from a bacterial toxin protein.

As used herein, the term "affinity tag" refers to such structures as a "poly-histidine tract" or "poly-histidine tag," or any other structure or compound which facilitates the purification of a recombinant fusion protein from a host cell, host cell culture supernatant, or both. As used herein, the term "flag tag" refers to short polypeptide marker sequence useful for recombinant protein identification and purification.

As used herein, the terms "poly-histidine tract" and "poly-histidine tag," when used in reference to a fusion protein refers to the presence of two to ten histidine residues at either the amino- or carboxy-terminus of a protein of interest. A poly-histidine tract of six to ten residues is preferred. The poly-histidine tract is also defined functionally as being a number of consecutive histidine residues added to the protein of interest which allows the affinity purification of the resulting fusion protein on a nickel-chelate or IDA column.

As used herein, the term "chimeric protein" refers to two or more coding sequences obtained from different genes, that have been cloned together and that, after translation, act as a single polypeptide sequence. Chimeric proteins are also referred to as "hybrid proteins." As used herein, the term "chimeric protein" refers to coding sequences that are obtained from different species of organisms, as well as coding sequences that are obtained from the same species of organisms.

The term "protein of interest" as used herein refers to the protein whose expression is desired within the fusion protein. In a fusion protein the protein of interest will be joined or fused with another protein or protein domain, the fusion partner, to allow for enhanced stability of the protein of interest and/or ease of purification of the fusion protein.

As used herein, the term "purified" or "to purify" refers to the removal of contaminants from a sample. For example, antitoxins are purified by removal of contaminating non-immunoglobulin proteins; they are also purified by the removal of immunoglobulin that does not bind toxin. The removal of non-immunoglobulin proteins and/or the removal of immunoglobulins that do not bind toxin results in an increase in the percent of toxin-reactive immunoglobulins in the sample. In another example, recombinant toxin polypeptides are expressed in bacterial host cells and the toxin polypeptides are purified by the removal of host cell proteins; the percent of recombinant toxin polypeptides is thereby increased in the sample. Additionally, the recombinant toxin polypeptides are purified by the removal of host cell components such as lipopolysaccharide (e.g., endotoxin).

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein refers to a protein which is isolated from a natural source as opposed to the production of a protein by recombinant means.

As used herein the term "portion" when in reference to a protein (as in "a portion of a given protein") refers to fragments of that protein. The fragments may range in size from four amino acid residues to the entire amino acid sequence minus one amino acid.

As used herein, the term "therapeutic amount" refers to that amount of antitoxin required to neutralize the pathologic effects of leukotoxin in a subject. It is intended that the term "subject" encompass non-human animals, including, but not limited to bovines, caprines, ovines, equines, porcines, felines, canines, fowl, etc., as well as humans. In preferred embodiments, the "subject" is a bovine, although it is not intended that the present invention be limited to this group of animals.

The term "pyrogen" as used herein refers to a fever-producing substance. Pyrogens may be endogenous to the host (e.g., prostaglandins) or may be exogenous compounds (e.g., bacterial endo- and exotoxins, nonbacterial compounds such as antigens and certain steroid compounds, etc.). The presence of pyrogen in a pharmaceutical solution may be detected using the U.S. Pharmacopeia (USP) rabbit fever test (United States Pharmacopeia, Vol. XXII [1990] United States Pharmacopeial Convention, Rockville, Md., p. 151).

The term "endotoxin" as used herein refers to the high molecular weight complexes associated with the outer membrane of gram-negative bacteria. Unpurified endotoxin contains lipids, proteins and carbohydrates. Highly purified endotoxin does not contain protein and is referred to as lipopolysaccharide (LPS). Because unpurified endotoxin is of concern in the production of pharmaceutical compounds (e.g., proteins produced in *E. coli* or *P. haemolytica* using recombinant DNA technology), the term endotoxin as used herein refers to unpurified endotoxin. Bacterial endotoxin is a well known pyrogen.

As used herein, the term "endotoxin-free" when used in reference to a composition to be administered parenterally (with the exception of intrathecal administration) to a host means that the dose to be delivered contains less than 5 EU/kg body weight (FDA Guidelines for Parenteral Drugs [December 1987]). Endotoxin levels are measured herein using the Limulus Amebocyte Lysate (LAL) test (Limulus Amebocyte Lysate Pyrochrome™, Associates of Cape Cod, Inc. Woods Hole, Mass.). To measure endotoxin levels in preparations of recombinant proteins, 0.5 ml of a solution comprising 0.5 mg of purified recombinant protein in 50 mM $NaPO_4$, pH 7.0, 0.3 M NaCl and 10% glycerol is used in the LAL assay according to the manufacturer's instructions for the endpoint chromogenic without diazo-coupling method. The specific components of the buffer containing recombinant protein to be analyzed in the LAL test are not important; any buffer having a neutral pH may be employed. Compositions containing less than or equal to than 250 endotoxin units (EU)/mg of purified recombinant protein are herein defined as "substantially endotoxin-free."

The LAL test is accepted by the U.S. FDA as a means of detecting bacterial endotoxins (21 C.F.R. §§ 660.100–105). Studies have shown that the LAL test is equivalent or superior to the USP rabbit pyrogen test for the detection of endotoxin and thus the LAL test can be used as a surrogate for pyrogenicity studies in animals (F. C. Pearson, *Pyrogens: Endotoxins, LAL Testing and Depyrogenation*, Marcel Dekker, New York (1985), pp. 150–155). The FDA Bureau of Biologics accepts the LAL assay in place of the USP rabbit pyrogen test so long as the LAL assay utilized is shown to be as sensitive as, or more sensitive as the rabbit test (Fed. Reg., 38, 26130 [1980]).

The term "monovalent" when used in reference to a vaccine refers to a vaccine which is capable of provoking an immune response in a host animal directed against a single type of toxin. For example, if immunization of a host with *P. haemolytica* type A1 leukotoxin vaccine induces antibodies in the immunized host which protect against a challenge with type A1 leukotoxin but not against challenge with other Pasteurella toxins, enzymes, or toxins from other organisms, then the type A1 vaccine is said to be monovalent. In contrast, a "multivalent" vaccine provokes an immune response in a host animal directed against several (i.e., more than one) toxins and/or enzymes associated with disease (e.g., glycoprotease and/or neuraminidase). For example, if immunization of a host with a vaccine comprising *P. haemolytica* type A1 leukotoxin induces the production of antibodies which protect the host against a challenge with both type A1 leukotoxin, as well as other toxins or deleterious enzymes, the vaccine is said to be multivalent. It is also intended that the term encompass vaccine preparations which include antigens/immunogens from sources other than *P. haemolytica*. For example, multivalent vaccines may be prepared that include recombinant *P. haemolytica* organisms or purified inactive leukotoxin, as well as antigens from viruses, fungi, and/or other bacteria. It is not intended that the vaccine be limited to any particular organism or immunogen.

The present invention further contemplates immunization with or without adjuvant. As used herein, the term "adjuvant" is defined as a substance known to increase the immune response to other antigens when administered with other antigens. If adjuvant is used, it is not intended that the present invention be limited to any particular type of adjuvant—or that the same adjuvant, once used, be used all the time. It is contemplated that adjuvants may be used either separately or in combination. The present invention contemplates all types of adjuvant, including but not limited to agar beads, aluminum hydroxide or phosphate (alum), Incomplete Freund's Adjuvant, as well as Quil A adjuvant commercially available from Accurate Chemical and Scientific Corporation, Gerbu adjuvant also commercially available (GmDP; C.C. Biotech Corp.), and bacterin (i.e., killed preparations of *P. haemolytica* cells). It is further contemplated that the vaccine comprise at least one "excipient" (i.e., a pharmaceutically acceptable carrier or substance) suitable for administration to a human or other animal subject. It is intended that the term "excipient" encompass liquids, as well as solids, and colloidal suspensions.

As used herein the term "immunogenically-effective amount" refers to that amount of an immunogen required to invoke the production of protective levels of antibodies in a host upon vaccination.

The term "protective level", when used in reference to the level of antibodies induced upon immunization of the host with an immunogen which comprises a bacterial toxin, means a level of circulating antibodies sufficient to protect the host from challenge with a lethal dose of the toxin.

As used herein the terms "protein" and "polypeptide" refer to compounds comprising amino acids joined via peptide bonds and are used interchangeably.

The terms "native gene" or "native gene sequences" are used to indicate DNA sequences encoding a particular gene which contain the same DNA sequences as found in the gene as isolated from nature. In contrast, "synthetic gene sequences" are DNA sequences which are used to replace the naturally occurring DNA sequences when the naturally occurring sequences cause expression problems in a given host cell. For example, naturally-occurring DNA sequences encoding codons which are rarely used in a host cell may be replaced (e.g., by site-directed mutagenesis) such that the synthetic DNA sequence represents a more frequently used codon. The native DNA sequence and the synthetic DNA sequence will preferably encode the same amino acid sequence.

The term "sample" as used herein is used in its broadest sense. For example, it refers to any type of material obtained from humans or other animals (e.g., any bodily fluid or tissue), cell or tissue cultures, cell lines, or a culture of microorganisms. "Sample" also encompasses food and feed (whether solid or liquid), media (whether solid or liquid) for the growth and maintenance of microorganisms and cell cultures, equipment and its components (e.g, dialysis, intravenous, and nasogastric tubing), disposable, as well as reusable patient care items (including catheters), environmental surfaces, soil, water and other fluids, and reagents (e.g., buffers).

As used herein, the term "eukaryote" refers to organisms distinguishable from "prokaryotes" (e.g., bacteria). It is intended that the term encompass all organisms with cells that exhibit the usual characteristics of eukaryotes such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the terms "antimicrobial" and "antibiotic" are used interchangeably in reference to any compound which inhibits the growth of, or kills microorganisms, including eukaryotes such as fungi (i.e., it includes antifungals). It is intended that the term be used in its broadest sense, and includes, but is not limited to compounds such as those which are produced naturally or synthetically. It is also intended that the term includes compounds and elements that are useful for inhibiting the growth of, or killing microorganisms.

As used herein, the term "antimetabolite" refers to any substance with a close structural resemblance to another, essential substance (i.e., metabolite) that is required for normal physiologic or genetic finction. Typically, antimetabolites exert their effects by interfering with the utilization of the essential metabolite.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, "amino acid sequence" as used herein refers to peptide or protein sequence. "Peptide nucleic acid" as used herein refers to an oligomeric molecule in which nucleosides are joined by peptide, rather than phosphodiester, linkages. These small molecules, also designated anti-gene agents, stop transcript elongation by binding to their complementary (template) strand of nucleic acid (Nielsen et al., Anticancer Drug Des., 8:53–63 [1993]).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, naturally occurring sequences.

As used herein, the term "non-polar" ("nonpolar") insertion refers to an insertion of a DNA fragment that does not negatively affect the expression of genes located downstream of the insertion.

As used herein, the term "insertional inactivation" refers to the abolition of the functional properties of a gene product by insertion of a foreign DNA sequence into the coding or regulatory portion of the gene. For example, the term encompasses the inactivation of lktC by the insertion of DNA such as the cat cassette.

A "substitution" results from the replacement of one or more nucleotides or amino acids by different nucleotides or amino acids, respectively.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

As used herein, the term "probe" refers to an oligonucleotide (i.e., a sequence of nucleotides), whether occurring naturally as in a purified restriction digest or produced synthetically, which is capable of hybridizing to another oligonucleotide or polynucleotide of interest. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is further contemplated that the oligonucleotide of interest (i.e., to be detected) will be labelled with a reporter molecule. It is also contemplated that both the probe and oligonucleotide of interest will be labelled. It is not intended that the present invention be limited to any particular detection system or label.

As used herein, the term "target" refers to the region of nucleic acid bounded by the primers used for polymerase chain reaction. Thus, the "target" is sought to be sorted out from other nucleic acid sequences. A "segment" is defined as a region of nucleic acid within the target sequence.

"Amplification" is defined as the production of additional copies of a nucleic acid sequence and is generally carried out using polymerase chain reaction (PCR) or other technologies well known in the art (e.g., Dieffenbach and Dveksler, *PCR Primer, a Laboratory Manual*, Cold Spring Harbor Press, Plainview N.Y. [1995]). As used herein, the term "polymerase chain reaction" ("PCR") refers to the method of K. B. Mullis (U.S. Pat. Nos. 4,683,195 and 4,683,202, hereby incorporated by reference), which provides methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "polymerase" refers to any polymerase suitable for use in the amplification of nucleic acids of interest. It is intended that the term encompass such DNA polymerases as Taq DNA polymerase obtained from *Thermus aquaticus*, although other polymerases, both thermostable and thermolabile are also encompassed by this definition.

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for insertion into recombinant vectors.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "nested primers" refers to primers that anneal to the target sequence in an area that is inside the annealing boundaries used to start PCR. (See, K. B. Mullis, et al., Cold Spring Harbor Symposia, Vol. LI, pp. 263–273 [1986]). Because the nested primers anneal to the target inside the annealing boundaries of the starting primers, the predominant PCR-amplified product of the starting primers is necessarily a longer sequence, than that defined by the annealing boundaries of the nested primers. The PCR-amplified product of the nested primers is an amplified segment of the target sequence that cannot, therefore, anneal with the starting primers. As used herein, the term "amplification reagents" refers to those reagents (deoxyribonucleoside triphosphates, buffer, etc.), needed for amplification except for primers, nucleic acid template and the amplification enzyme.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

The terms "targeting vector" or "targeting construct" refer to nucleotide sequences comprising a gene of interest flanked on either side by a recognition sequence which acts as a substrate for a protein, which is capable of homologous recombination of the DNA sequence located between the flanking recognition sequences.

As used herein, the terms "vector" and "vehicle" are used interchangeably in reference to nucleic acid molecules that transfer DNA segment(s) from one cell to another. The terms "shuttle vector" or "bifunctional vector" refer to a cloning vector (i.e., vector) that is capable of replication in two different organisms. These vectors can "shuttle" between the two hosts. For example, the present invention encompasses shuttle vectors that are capable of replicating in both *P. haemolytica* and *E. coli*.

The terms "expression vector" or "expression cassette" as used herein, refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), a ribosome binding site, and an initiation codon, often along with other sequences. The term "expression" may refer to "gene expression" and/or "protein expression."

As used herein, the term "multiple cloning site module" or refers to nucleic acid that contains multiple cloning sites (i.e., "restriction sites," "MCS," or "polylinker"). It is intended that the term encompass DNA that contain unique, as well as non-unique restriction sites. It also is intended to encompass multiple cloning site modules that contain foreign (i.e., exogenous) DNA inserted within the DNA containing the MCS. This foreign DNA may be inserted within the MCS by recombinant techniques. The DNA may also contain foreign DNA that is inserted in locations other than the MCS.

The terms "in operable combination," "in operable order," and "operably linked" as used herein, refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "promoter element," "promoter," or "promoter sequence" as used herein, refer to a DNA sequence that is located at the 5' end of (i.e., precedes) a gene in a DNA polymer and provides a site for initiation of the transcription of the gene into mRNA. A "strong promoter" is a promoter that can sustain a high rate of transcription, while a "weak promoter" is a promoter that is relatively inefficient, and capable of a sustaining only a low rate of transcription.

As used herein, the term "promoter-probe" refers to a DNA sequence that contains a selectable marker, but lacks a promoter sequence. For example, such promoter probes may be located on expression vectors. It is intended that the term encompass structures commonly referred to as "promoter traps" used in such methods as "promoter capture." It is contemplated that the term encompass such plasmids as pNF2283.

As used herein, the term "replicon" refers to a genetic element that behaves as an autonomous unit during DNA replication. The term also encompasses nucleic acid regions or units that have a single site for origin of replication. An "incompatible replicon" is a replicon that is inserted into an organism's chromosomal DNA and/or plasmid DNA, that is incompatible with other genetic elements present in the cell.

As used herein the term "portion" when in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions. The term "hybridization" as used herein includes "any process by which a strand of nucleic acid joins with a complementary strand through base pairing" (Coombs, *Dictionary of Biotechnology*, Stockton Press, New York N.Y. [1994].

"Stringency" typically occurs in a range from about $T_m-5°$ C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridisation, in *Nucleic Acid Hybridisation* [1985]). Other references include more sophisticated computations which take structural as well as sequence characteristics into account for the calculation of $T_m$.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH [fluorescent in situ hybridization]).

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "antigenic determinant" as used herein refers to that portion of an antigen that makes contact with a particular antibody (i.e., an "epitope"). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A", the presence of a protein containing epitope A (or free, unlabelled A) in a reaction containing labelled "A" and the antibody will reduce the amount of labelled A bound to the antibody.

As used herein, the term "neutralizing" is used in reference to antibodies with the ability to prevent the pathological actions of a particular substance, such as the leukotoxin of *P. haemolytica* (i.e., an "antitoxin"). It is contemplated that neutralizing antibodies be utilized in passive immunization protocols to prevent the action of toxins, in particular *P. haemolytica* leukotoxin. It is further contemplated that neutralizing antibodies be utilized to alleviate the effect(s) of toxins in an individual, in particular *P. haemolytica* leukotoxin.

As used herein, the term "immunogen" refers to a substance, compound, molecule, or other moiety which stimulates the production of an immune response. The term "antigen" refers to a substance, compound, molecule, or other moiety that is capable of reacting with products of the immune response. For example, verotoxin subunits may be used as immunogens to elicit an immune response in an animal to produce antibodies directed against the subunit used as an immunogen. The subunit may then be used as an antigen in an assay to detect the presence of anti-verotoxin subunit antibodies in the serum of the immunized animal.

"Alternations in the polynucleotide" as used herein comprise any alteration in the sequence of polynucleotides encoding active or inactive leukotoxin, including deletions, insertions, and point mutations that may be detected using hybridization assays. Included within this definition is the detection of alterations to the genomic DNA sequence which encodes active or inactive leukotoxin (e.g., by alterations in pattern of restriction enzyme fragments capable of hybridizing to any sequence (e.g., by RFLP analysis), the inability of a selected fragment of any sequence to hybridize to a sample of genomic DNA (e.g., using allele-specific nucleotide probes), improper or unexpected hybridization, such as hybridization to a locus other than the normal chromosomal locus for the leukotoxin genes (e.g., using FISH to metaphase chromosomes spreads, etc.).

A "variant" in regard to amino acid sequences is used to indicate an amino acid sequence that differs by one or more amino acids from another, usually related amino acid. The variant may have "conservative" changes, wherein a substituted amino acid has similar structural or chemical properties (e.g., replacement of leucine with isoleucine). More rarely, a variant may have "non-conservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software. Thus, it generations, then colonies were screened for loss of $Sm^R$ and plasmid DNA. pYFC1 was then transferred into the resulting $Sm^S$ strain, SH1217, by electroporation as described by Craig et al., (Craig et al., J. Gen. Microbiol., 135:2885–2890 [1989]).

Briefly, the plasmid DNA was isolated by the lysozyme-EDTA method known in the art (See, Maniatis et al., *Molecular Cloning: A Laboratory Manual*, Cold Spring Harbor Press, Cold Spring Harbor, N.Y. [1982]). Plasmid DNA was ethanol precipitated and washed with 70% ethanol to remove all ionic species, and then resuspended in 2 µl sterile distilled water. The approximate plasmid DNA concentrations in the preparation were determined by comparison of the staining intensities with ethidium bromide of increasing dilutions of the unknown sample, after separation on an agarose gel, with those of known quantities of reference DNA (λ DNA digested with HindIII). Gel electrophoresis was conducted with 0.7% (w/v) agarose (type II; Sigma) and TBE buffer, as known in the art and described by Maniatis et al. (Maniatis et al., supra).

Electrocompetent *P. haemolytica* cells were prepared by inoculating 1 l of BHI with 30–40 mls of an overnight culture (the $OD_{600}$ was close to 0.1). The culture was incubated at 37° C. with shaking, until an $OD_{600}$ of 0.5 to 1.0 was achieved, and the $OD_{600}$ value was recorded. The cells were then harvested by centrifugation for 10 minutes at 8,000 rpm, at 4° C. The cells were resuspended in 500 ml cold, sterile 9.3% sucrose, 10% glycerol (electroporation buffer). The cells were centrifuged for 10 minutes, at 8,000 rpm at 4° C., and the supernatant was removed. This wash step was repeated, and the pellet was then resuspended in 20 ml, cold, sterile electroporation buffer, and centrifuged for 10 minutes at 8,000 rpm, at 4° C. The supernatant was removed, and this wash step was repeated. The pellet was then resuspended in 2.5 ml cold, sterile 10% glycerol. The cell suspension was dispensed in 120 µl aliquots into sterile microfuge tubes, snap-frozen on dry ice/ethanol, and immediately placed in storage at −70° C. Prior to electroporation, the cells were removed from frozen storage and thawed on ice.

Controls were run in parallel with the test samples, including cells tested only on selective media (to detect contamination of the cultures), known quantities of plasmid DNA (to determine electroporation frequency), and electroporated cells were compared with non-electroporated cells plated on BHI (to check viability).

Electroporation was performed using a Gene Pulser (Bio-Rad) linked to a Capacitance Extender (Bio-Rad), and to a Pulse Controller (Bio-Rad). The cells were kept on ice throughout the procedure. Fifty µl of the cell suspension were added to the DNA suspension, and the mixture was placed in a cold, sterile, 0.1 cm gap cuvette. Excess moisture was wiped from the cuvette, the cuvette was placed in an electroporation holder and 15–20 kilovolts, 400 ohm, 25 µfarad pulse applied. One ml BHI/SOC medium was added to the cuvette and mixed by gentle pipetting, and the suspension was removed to a sterile tube. The mixture was incubated for 60 minutes at 37° C., with gentle shaking to allow expression of markers. The suspension was then plated on 5% sheep blood agar plates containing the appropriate antimicrobials.

The efficiency of plasmid transfer to *P. haemolytica* strain SH1217 by electroporation was determined for various plasmids as indicated in Table 1. In this determination, plasmid DNAs were isolated from SH1217 (serotype A1, $Ap^S$, $Sm^S$, $Cm^S$, $Km^S$) or from *E. coli* XL1-Blue (recA1, endA1, gyrA96, thi-1, hsdR7, supE44, relA1, lac [F'proAB lacIqZΔM15 Tn10]; Stratagene), and transformed into SH1217 by electroporation as described in Example 1. Plasmid transfer was confirmed by restriction analysis of reisolated plasmid DNA, and neither DNA deletion nor rearrangement were observed.

A 4.3-kb endogenous $Ap^R$ plasmid, pSH10, which is similar to pPH843 and pAB2 (Azad et al., Gene 145:81–85 [1994]; and Wood and Lainson, Res. Vet. Sci., 68:163–168 [1995]), could also be electroporated into this strain with high efficiency (Table 1). In each case, transfer of DNA isolated from *E. coli* occurred at equal frequency to that isolated from *P. haemolytica*, indicating that pYFC1 and pSH10 are immune to host restriction by this strain.

The results obtained for plasmids pYFC1, pSH10, pNF2153, pNF2176, pNF2192, pNF2214, pNF2200 (construction of these plasmids is described in the following Examples) are indicated in Table 1. In this Table, the values are reported as cfu/µg of input DNA. Also, the electroporation frequencies for pNF2200 were measured using either ampicillin or chloramphenicol as the primary selection agent, as indicated.

TABLE 1

Efficiency of Plasmid Transfer to
*P. haemolytica* Strain SH1217

| Plasmid | Resistance Selected | DNA from *P. haemolytica* | DNA from *E. coli* |
|---|---|---|---|
| pYFC1 | Sm | $10^6$ | $10^6$ |
| pSH10 | Ap | $10^7$ | $10^7$ |
| pNF2153 | Ap | $10^5$ | $10^5$ |
| pNF2176 | Ap | $10^6$ | $10^6$ |
| pNF2192 | Km | $10^5$ | $10^2$ |
| pNF2214 | Km | $10^5$ | $10^2$ |
| pNF2200 | Ap | $10^5$ | $10^3$ |
| pNF2200 | Cm | $10^3$ | $10^1$ |

EXAMPLE 2

Construction of Expression Vector pNF2176

Figure 2:
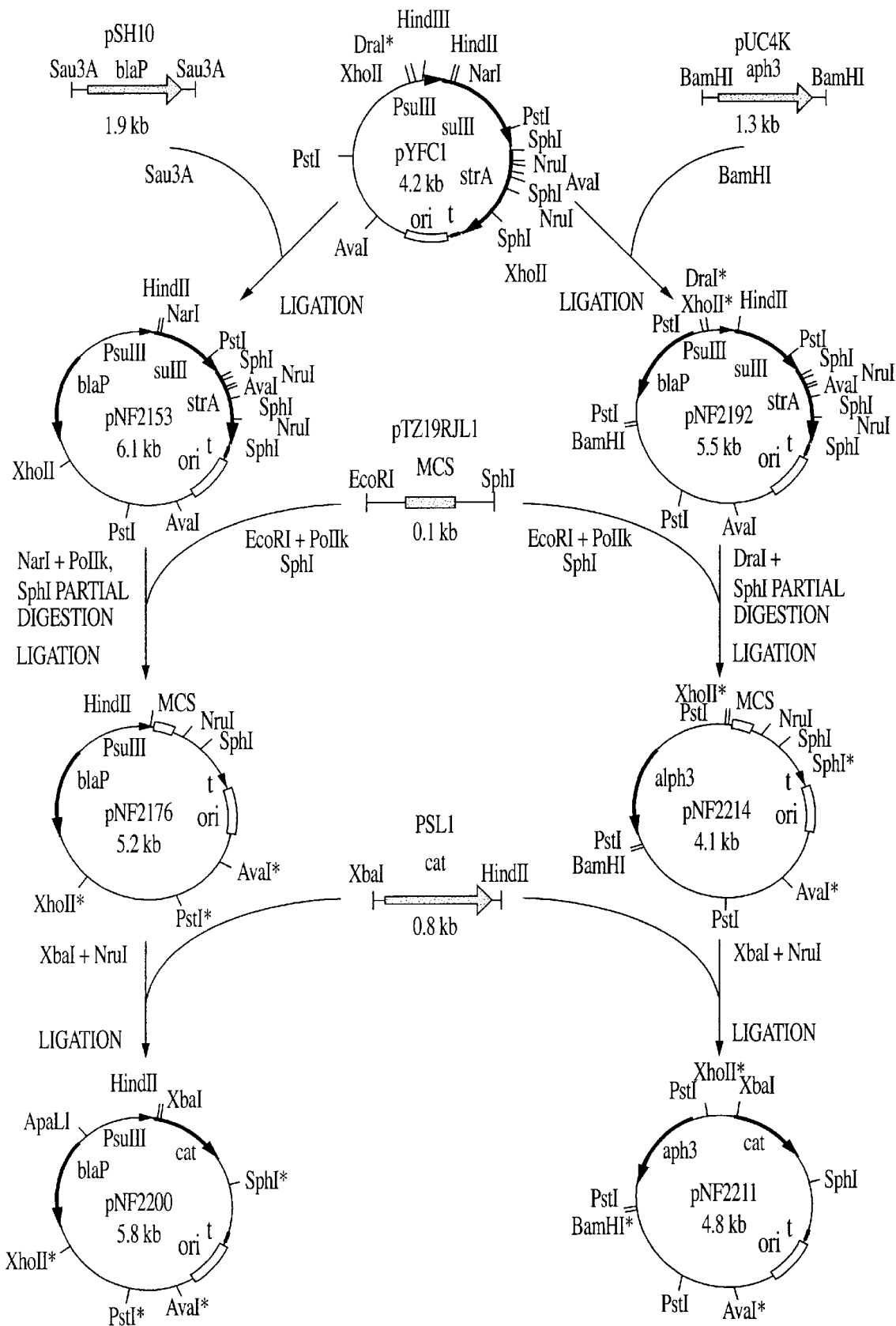

In this Example, a plasmid, pNF2176 (Genbank accession #U65076) capable of replication in both *P. haemolytica* and *E. coli* was constructed. As some *E. coli* promoters are not transcribed in *P. haemolytica* (West et al., Gene 160:81–86 [1995]), pYFC1 was modified to use $P_{sulII}$ for expression of foreign DNA in *P. haemolytica* (See, FIG. 2). The *P. haemolytica* ROB-1 β-lactamase gene, blaP (See, Liverly et al., Antimicrob. Agents Chemother., 35:242–251 [1991]; and Wood and Lainson, supra) was cloned as a 1.9 kb Sau3A fragment of pSH10 into the XhoII site of pYFC1 to create the plasmid pNF2153. Then, the sulII and stgrA genes were deleted and replaced with an MCS, by ligating the 5.1 kb NarI-SphI fragment of pNF2153 to the EcoRI-SphI fragment carrying the MCS of pTZRJL19 (Fermentas); for each fragment, the 3' recessed ends were first filled in, using polIK, and then the fragments were digested with SphI and ligated.

The expression plasmid pNF2176 carries the pYFC1 ori, the blaP gene, $P_{sulII}$, and has ten unique restriction sites for cloning that are located immediately downstream of the promoter. Plasmid pNF2176 was found to be capable of replication in both *P. haemolytica* and *E. coli*, and can be transferred from *E. coli* to *P. haemolytica* with relatively high efficiency, as shown in Table 1.

EXAMPLE 3

Construction of Cloning Vector pNF2214 and Expression of Kanamycin Resistance in *P. haemolytica*

In this Example, an alternate plasmid (pNF2214; GenBank accession #U65078) carrying a different marker for selection was created. This plasmid carries the Tn903 Kan$^R$ gene, aph3 (See, Oka et al., J. Mol. Biol., 147:217–226 [1981]). This gene is expressed in many organisms, including A. pleuropneumoniae and P. haemolytica (Homchampa et al., Vet. Microbiol., 42:35–44; West et al., supra). The construction method was analogous to that used for construction of pNF2176, except that the construction also resulted in deletion of P$_{sulII}$ (See, FIG. 2).

First, the aph3 was cloned as a 1.3 kb BamHI fragment from pUC4K (Pharmacia) into the XhoII site of pYFC1, to create pNF2192. Next, the 1.4 kb region between the DraI and SphI sites was replaced with the EcoRI-SphI MCS-containing fragment of pTZRJL19. The order of the restriction sites within this MCS is: EcoRI-MluI-SnaI-ApaI-KpnI-SmaI-XmaI-AvaI-BamHI-XhoII-XbaI-SalI-PstI-SphI; not all of these restriction sites are unique.

The aph3 gene was expressed in P. haemolytica in both orientations of insertion of the vector, indicating that it is transcribed from its own promoter in this microorganism. The efficiency of transfer of pNF2214 from E. coli to P. haemolytica was decreased with respect to DNA isolated from P. haemolytica. This suggested that the cloned sequences used in the vector contained sites for one or more of the P. haemolytica restriction systems.

EXAMPLE 4

Expression of Chloramphenicol Resistance in P. haemolytica

In this Example, chloramphenicol resistance was expressed in P. haemolytica. Expression of the type I and type II chloramphenicol resistance genes (cat) has been reported in P. haemolytica (See e.g., Frey, Res. Microbiol., 143:263–269 [1992]; Azad et al., Gene 145:81–85 [1994]; Briggs et al., Appl. Environ. Microbiol., 60:2006–2010 [1994]; and West et al., supra), although the reported resistance levels were low (e.g., 2 µg/ml), and plasmid DNA could not be recovered from the transformants.

However, chloramphenicol resistance was considered to be a desirable selectable marker at this point in the development of the present invention, as most P. haemolytica strains are sensitive to chloramphenicol, and do not exhibit detectable spontaneous resistance (See e.g., Craig et al., J. Gen. Microbiol., [1989]; and Diker et al., Vet. Rec., 134:597–598 [1994]).

To enhance cat expression in P. haemolytica, and to demonstrate the utility of pNF2176 as an expression vector, a promoterless cat cassette from pSL1 (Lukomski et al., supra) was used as a reporter gene. The promoterless cat cassette was ligated as a 0.8 kb XbaI-HindII fragment from pSL1 (Lukomski et al., J. Bacteriol., 178:240–247 [1996]) to XbaI+NruI linearized pNF2176 or pNF2214, to create pNF2200 and pNF221 1, respectively. The strA transcriptional terminator is marked in FIG. 2 (t).

In P. haemolytica, pNF2200 conferred chloramphenicol resistance at 10 µg/ml. This level of resistance is five times greater than that observed in P. haemolytica of similar copy number (See, Frey, supra; Azad et al., supra; and Briggs et al., supra), indicating that P$_{sulII}$ enhances cat transcription. However, it was also observed that the frequency of transfer of pNF2200 from E. coli to P. haemolytica was reduced by 100-fold, if chloramphenicol was used as the primary selective antimicrobial (See, Table 1), yet all of the transformants obtained were ampicillin and chloramphenicol resistant, regardless of the primary selection antimicrobial used. For pNF2211, where P$_{sulII}$ was deleted, chloramphenicol resistance was observed in E. coli, but not in P. haemolytica.

EXAMPLE 5

Construction of Promoter-Probe Vector pNF2283

Figure 3:
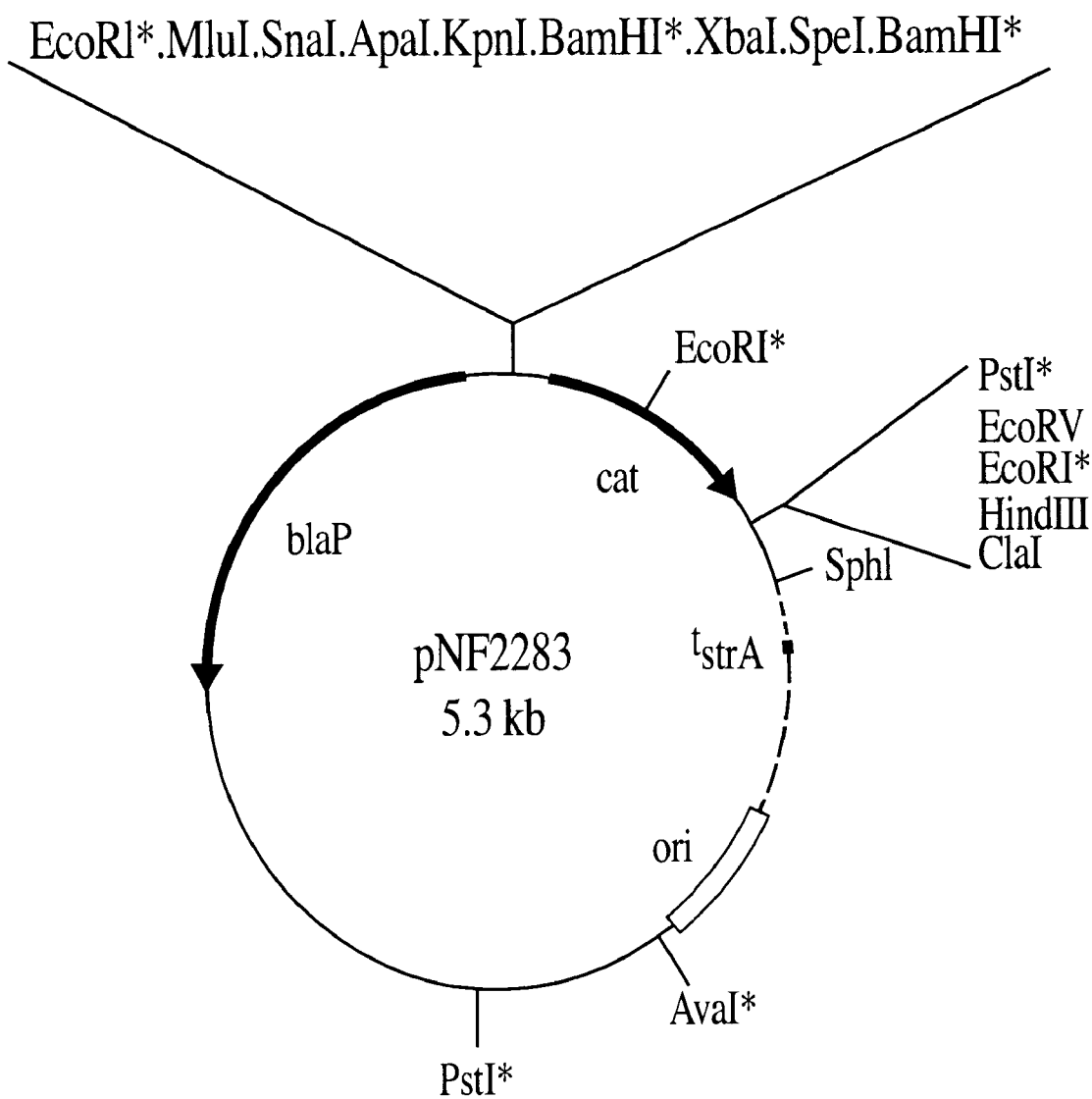

Chloramphenicol acetyltransferase is a convenient reporter for measuring gene expression from operon and protein fusions. Thus, in this Example, plasmid pNF2200 was adapted for use as a promoter-probe vector, using cat as a reporter gene, by deleting the upstream PsuIII, to create pNF2283 (See, FIG. 3). pNF2283 (GenBank accession #U65077) was created by deleting the 0.5 kb ApaLI-HindIII fragment containing P$_{sulII}$ from pNF2200. The ApaLI 3' recessed ends were first filled in using PoIIK, then the plasmid DNA was digested with HindIII, and self-ligated. Non-unique restriction sites are marked with asterisks in FIG. 3. In FIG. 3, t$_{strA}$ indicates the location of the strA transcriptional terminator.

pNF2283 is ampicillin resistant and chloramphenicol sensitive, both in E. coli and in P. haemolytica. Six unique restriction sites, plus two closely spaced BamHI sites are available for the insertion of promoter-containing fragments. The strA transcription terminator lies immediately downstream of cat, so the downstream replication region should be protected from potential disruptive effects of read-through transcription when strong promoters are cloned on the vector. It is contemplated that pNF2283 will be useful for promoter analysis both in E. coli and P. haemolytica. Importantly, this plasmid can be transferred from E. coli to P. haemolytica at an efficiency of approximately 100 cfu/µg DNA. It is further contemplated that pNF2211 may also be suitable as a promoter-probe vector in P. haemolytica, though its efficiency of transfer from E. coli to P. haemolytica is only 10 cfu/µg DNA.

EXAMPLE GROUP II

In the following set of Examples (Examples 6–12), an lktC mutant of P. haemolytica was created and trans-complementation was used to demonstrate that LktC is required for conversion of the proleukotoxin to mature active toxin. In addition, insertion of the cat gene at the leukotoxin locus created an operon fusion that can be used to quantitate leukotoxin transcription in P. haemolytica, providing a convenient assay to determine the quantity of leukotoxin produced by strains of P. haemolytica.

In these Examples, E. coli strain XL1-Blue (recA1 endA1 gyrA96 thi-1 hsdR17 supE44 relA1 lac [F'proAB lacI$^q$ZDM15 Tn10]; Stratagene) was used for plasmid propagation and cloning. E. coli was grown at 37° C. on liquid or solid Luria-Bertani medium. P. haemolytica strain SH1217 was also used in these Examples. P. haemolytica was grown at 37° C. in liquid or solid Brain Heart Infusion (BHI) media (Difco) or on 5% sheep blood agar plates. Unless otherwise indicated antimicrobials were used in the selective media at the following concentrations for E. coli: ampicillin (Ap), 50 µg/ml; chloramphenicol (Cm), 30 µg/ml; streptomycin (Sm), 20 µg/ml; for P. haemolytica, the concentrations used were Ap, 50 µg/ml; Cm, 5–10 µg/ml; Sm, 100–500 µg/ml. Also, unless otherwise indicated, blood agar base (Difco) with 5% sheep blood (i.e., 5% sheep blood agar plates) was used the selective media containing antimicrobials.

Standard recombinant DNA techniques known to those in the art were used in these Examples. Plasmid DNAs were isolated from P. haemolytica or from E. coli using the FlexiPrep Kit (Pharmacia). E. coli cells were transformed by electroporation as known in the art (See e.g., W. Dower et al., Nucl. Acids Res., 16:6127–6145 [1988], and Sharma and Schimke, BioTechn., 20:42–44 [1996]). Briefly, this method utilizes a salt-free growth medium to facilitate electroporation. Sterile solutions were used in all of these steps.

In this method, a fresh, overnight culture of *E. coli* was grown in liquid YENB medium (0.75% yeast extract, and 0.8% nutrient broth; DIFCO). One liter of fresh YENB medium was inoculated with 5–10 ml of the fresh culture and cells were grown at 37° C., with shaking. Cells were harvested at an $OD_{600}$ of 0.5 to 0.9, by chilling the culture on ice for about 5 minutes and centrifuging at 4000×g for 10 minutes at 4° C. The supernatant was removed, and the cell pellet was washed twice in 100 ml cold water, and rewashed as above. The cells were resuspended in 20 ml cold 10% glycerol, and then centrifuged at 4000×g for 10 minutes at 4° C., and the supernatant was discarded. The cells were then resuspended, to produce a final volume of 2–3 ml in cold 10% glycerol. The cell suspension contained approximately $2–4×10^{10}$ cells/ml. These cells were frozen by aliquoting 120 μl of the suspension into tubes, and placing the tubes in dry ice until frozen. The cells were then stored at −70° C. until use, at which time, the cells were thawed on ice.

*P. haemolytica* cells were prepared and electroporated, as previously described in Example 1. As a shuttle vector, an $Ap^R$ *P. haemolytica-E. coli* shuttle vector, pNF2176 prepared as described in the above Examples was used. pYFC1 and pNF2176 are incompatible because they both carry the same ori; and in the absence of selection, homoplasmid strains are easily segregated.

EXAMPLE 6

Construction of Mutagenic Plasmid pNF2237

Figure 4:
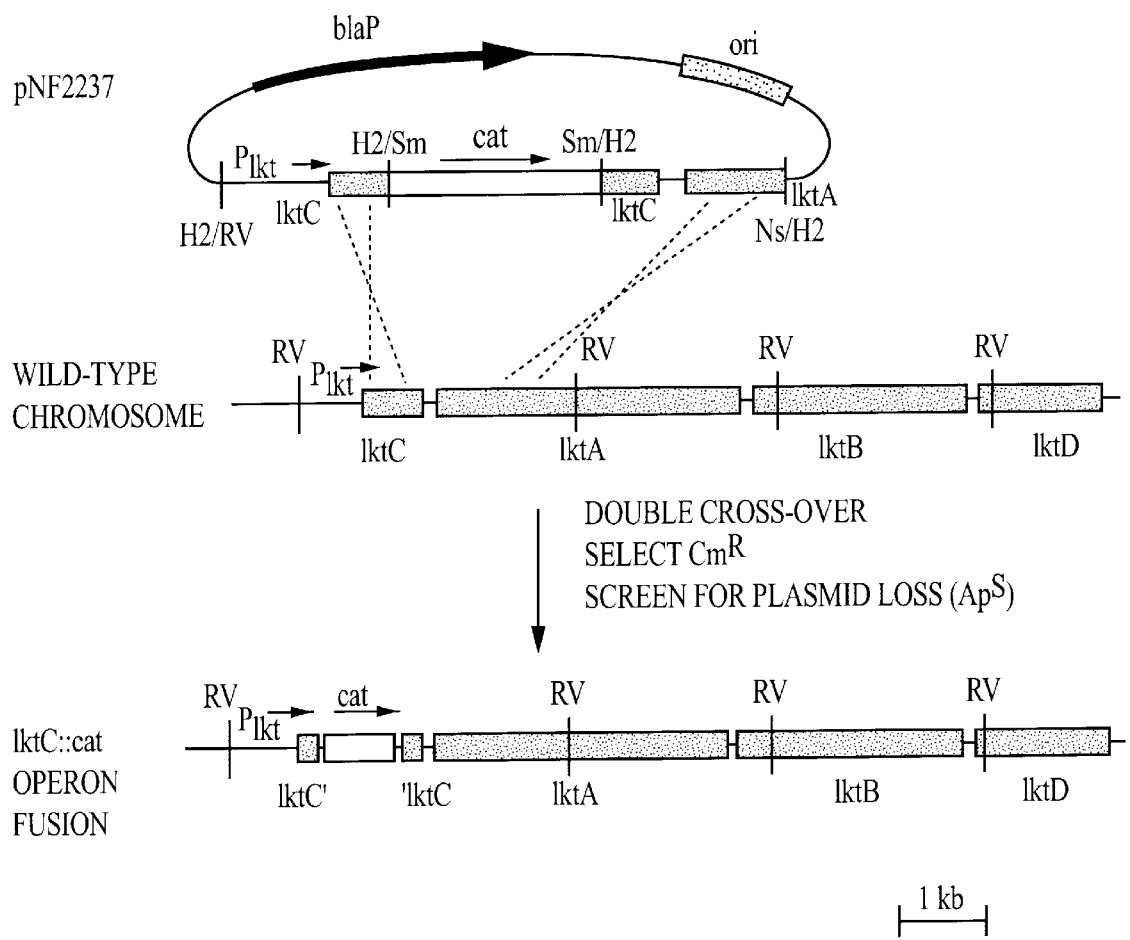

In this Example, the mutagenic plasmid pNF2237 was constructed. The sequence of this plasmid is SEQ ID NO:4 First, a plasmid, pNF2232, was constructed by cloning the 2 kb EcoRV-NsiI fragment of pSH224 (See e.g., S. Highlander et al., DNA Cell. Biol., 8:15–28 [1989]), carrying lktC and the 5' end of lktA, onto HincII-linearized pNF2176. Complete sequence information is available for the pNF2232 (SEQ ID NO:3) (the insert in the vector is deposited under the GenBank accession numbers M24197, M34943, and M34944). The promoterless nonpolar cat cassette was excised from pSL1 (See, S. Lukomski et al., J. Bacteriol., 178:240–247 [1996]) by SmaI digestion (0.7 kb), and inserted into the HincII site within the lktC reading frame on pNF2232, to create pNF2237. Thus, as shown in FIG. 4, the lktC gene is insertionally inactivated and the leukotoxin promoter is fused to cat in pNF2237. In this Figure, "RV" indicates "EcoRV" sites, "H2" indicates HincII sites, "Ns" indicates NsiI sites, "Sm" indicates SmaI sites, and $P_{lkt}$ indicates the leukotoxin promoter. The cat gene contains the complete CAT polypeptide coding sequence, but lacks a promoter and transcriptional terminator. Furthermore, the cat open reading frame is preceded by translational stop codons in all three reading frames and is immediately followed by a consensus ribosome-binding site, GGAGG, and an ATG start codon at its 5' end (See e.g., Lumoski et al., supra).

EXAMPLE 7

Selection of lktC Strains and Plasmid Curing in *P. haemolytica*

In this Example, lktC⁻ strains were identified and *P. haemolytica* lktC mutants were cured of pYFC1. In these experiments, *P. haemolytica* SH1217, carrying pNF2237 was electroporated (as described in Example 1) with the incompatible plasmid, pYFC1. The electroporated cultures were grown on media containing streptomycin, and transformants selected. The presence of both autonomous plasmids was confirmed by replica plating onto ampicillin and chloramphenicol-containing plates, and by preparing and analyzing plasmids minipreps as known in the art (See e.g., Maniatis, supra). Both plasmids were observed by agarose gel electrophoresis.

Transformants were pooled and propagated overnight in 5 ml BHI broth containing 500 μg/ml of streptomycin to permit plasmid segregation. To select clones where cat was rescued by allelic exchange at the lktCABD locus, 100 μl of the overnight culture was spread on BHI plates containing 5 μg/ml of chloramphenicol and 100 μg/ml of streptomycin. Then, $Sm^R Cm^R Ap^S$ double recombinants were detected by replica plating onto Ap plates. Of 500 colonies screened, four $Ap^S$ double recombinants were identified.

*P. haemolytica* lktC mutants (i.e., to create an isogenic LktC⁻ strain) were cured of pYFC1 by propagating them overnight in BHI broth containing 20 μg/ml of novobiocin (Sigma), passing them for three days in broth without antimicrobials and then plating the culture for single colony isolation to verify that the cat gene was stably maintained. Following this treatment, it was found that 75% of the colonies had lost pYFC1, but all had stably maintained the cat fusion.

EXAMPLE 8

Analysis of the Insert Configuration

In this Example, the configuration of the inserts in each strain was examined by Southern hybridization. *P. haemolytica* genomic DNA was isolated using the DNAzol reagent (Life Technologies). One microgram of genomic DNA was digested overnight with 20 units of EcoRV and fragments were separated by electrophoresis in a 0.8% agarose gel. Southern blotting was performed as known in the art (See e.g., Highlander et al., DNA Cell Biol., 8:15–28 [1989]. Briefly, the nucleic acids present in the electrophoresed gel were transferred to nylon membranes (Schleicher and Scheull) in alkaline transfer buffer (0.4 N NaOH, and 0.6 N NaCl) using the Vacublot vacuum transfer system (American Bionetics). The blot was neutralized, dried and then hybridized at 65° C. The blot was hybridized with one of the following $^{32}P$-labeled (Random Primed DNA Labeling Kit, Boehringer Mannheim) DNA fragments: the 2.0-kb EcoRV-NsiI fragment of pSH224, the 0.7-kb SmaI fragment of pSLI, or HincII-linearized pNF2176.

In each strain, the 3.1 kb EcoRV fragment carrying lktC was replaced by the inactivated copy corresponding to a fragment of 3.8 kb. This corresponds to the size of the fragment plus the cat cassette. When the cat cassette was used as a probe, the same fragments hybridized with the probe in the lktC mutants, and no hybridization signals were detected for the wild-type strain. Vector DNA alone did not hybridize to DNA in any of the mutants. Thus, in each of the $Sm^R Cm^R Ap^S$ isolates analyzed, double recombination had occurred at the leukotoxin locus. None contained replicon fusions between pNF2237 and pYFC1 and none resulted from single recombination events. One of the lktC mutants, "SH1562," was chosen for analysis in subsequent experiments.

EXAMPLE 9

Chloramphenicol Acetyl Transferase Assays

The cat gene is an important reporter to study transcriptional regulation because it produces an enzyme that can be easily assayed with specificity and great sensitivity (See e.g., Shaw, Chloramphenicol acetyltransferase from chloramphenicol-resistant bacteria, in J. H. Hushs (ed.), *Methods in Enzymology*, Academic Press, New York [1982] pp. 737–775). In this Example, the fluor-diffusion assay of Neumann et al., (See, Neumann et al., BioTechn., 5:444–447 [1987]) was adapted to measure Cm acetyl transferase activity from the lktC::cat operon fusions on the plasmid pNF2237 and on the chromosome (SH1562).

In this Example, cultures of the lktC::cat fusion strain (SH1562), SH1217, SH1217 carrying pNF2237, and SH1217 carrying pNF2176, were grown at 37° C. in BHI with rotatory shaking. At different time points on the growth curve, 1 ml culture samples were collected by centrifugation at 12,000×g for 2 minutes, then cooled to 4° C., washed in 1 ml of 0.1 M Tris (pH 7.8), and finally resuspended in 1 ml of 1 mM DTT, 0.1 M Tris (pH 7.8). Cells were sonicated for two 10 second bursts at 50 watts, and then centrifuged at 12,000×g for 30 minutes at 4° C., to remove cell debris. Cell extracts were normalized with respect to $OD_{600}$ and stored at −20° C. The CAT assay was carried out in 3.5 ml glass miniscintillation vials. Two $\mu$l of each cell extract were added to a 250 $\mu$l reaction mixture containing 100 mM Tris-HCl (pH 7.8), 1.0 mM Cm and 0.1 mM [$^3$H]acetyl coenzyme A (200 mCi/mmol, 0.5 mCi/ml; DuPont NEN Research Products). The reaction mixture was gently overlaid with 3 ml of a water-immiscible scintillation fluor (Econofluor, Packard) and then incubated at 25° C. At selected time intervals, the individual vials were counted for 1 min.

Figure 5A:
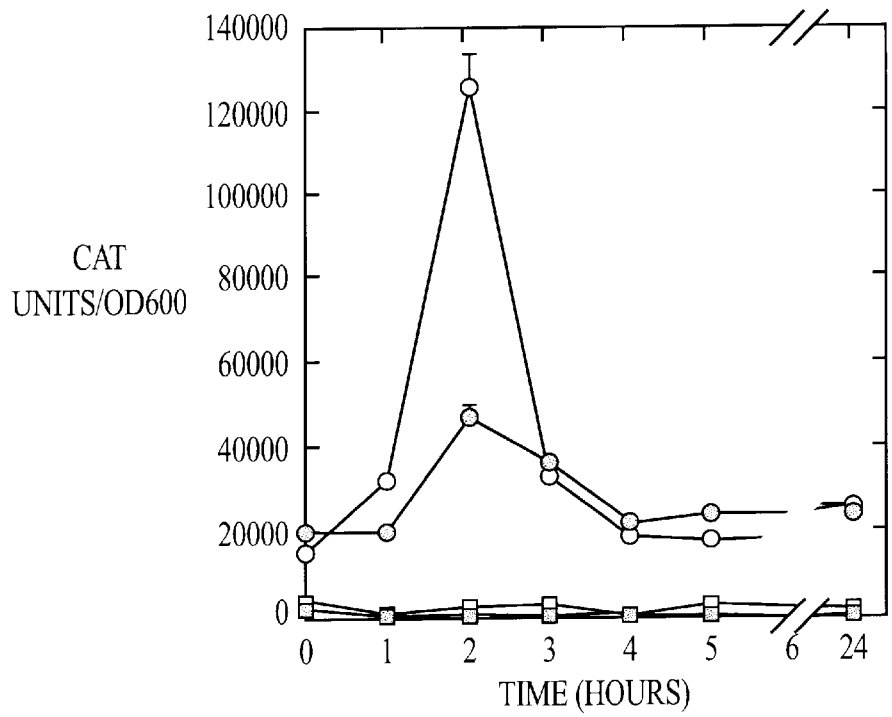
Figure 5B:
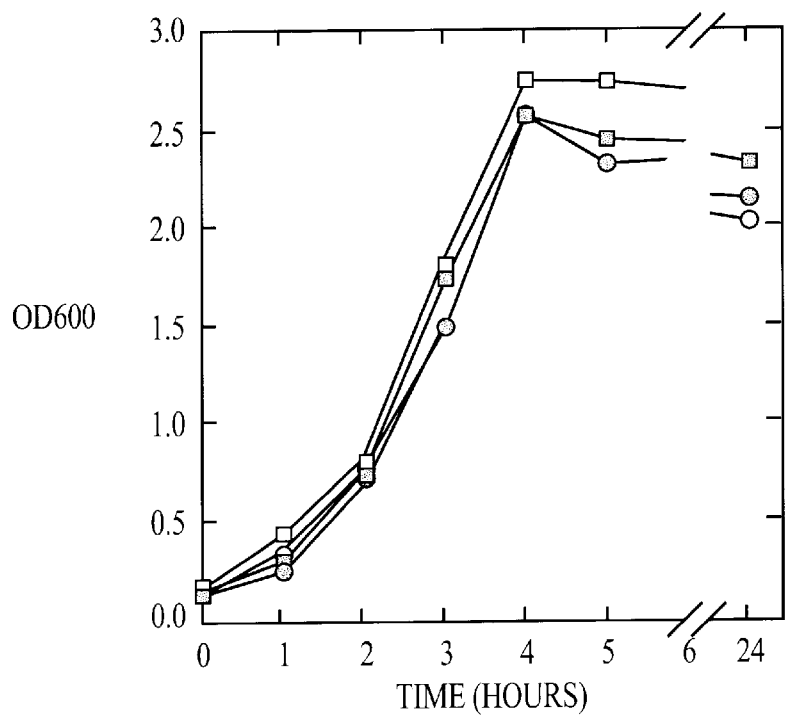

The results shown in FIG. 5, indicated that cat expression from the leukotoxin promoter was growth-phase dependent whether carried on the chromosome or on a plasmid. In this Figure, SH1562 is indicated by filled circles, SH1217 is indicated by open squares, SH1217 carrying pNF2176 is indicated by filled squares, and SH1217 carrying pNF2237 is indicated by open circles. In panel A, CAT activity is reported as counts per minute (cpm) per $OD_{600}$ of the culture at the indicated time points. Panel B shows the growth curves for each of the cultures. The results shown in this Figure represent averages for duplicate samples.

As indicated in FIG. 5, a peak of activity occurred during the early logarithmic phase of growth and activity rapidly declined to a steady-state level as the cells entered mid-logarithmic phase for each culture. A three-fold higher level of activity was observed in the multicopy plasmid state than in the single copy state, but in stationary phase, both the SH1217 carrying pNF2237, and SH1562 stains produced nearly equivalent levels of the enzyme. As mentioned above, based on copy number consideration, it was predicted that the plasmid encoded levels would be at least 10-fold higher than chromosomal levels.

EXAMPLE 10

Trans-Complementation of Hemolysis by lktC

In the related *E. coli* hemolysin system, the HlyC protein functions as an acyl transferase that post-translationally modifies and activates prohemolysin (See, J.-P. Issartel et al., Nature 351:759–761 [1991]). In this experiment, the LktC protein in *P. haemolytica* was assumed to have a similar mode of action. Since leukotoxin is responsible for the hemolytic activity of *P. haemolytica* (Murphy et al., Infect. Immun., 63:3209–3212 [1995]), it was hypothesized that inactivation of lktC would result in a non-hemolytic phenotype.

In this Example, *P. haemolytica* SH1562, SH1562 carrying pNF2176, SH1562 carrying pNF2232, and wild-type SH1217 were streaked on blood agar plate and incubated overnight at 37° C. The plates were observed for the presence of hemolysis by removing a portion of the growth of each strain with a cotton-tipped applicator. The results indicated that inactivation of lktC results in a non-hemolytic phenotype, further verifying that the $Cm^R$ $Ap^S$ isolates resulted from recombination at the leukotoxin locus. To provide direct evidence that LktC is required for leukotoxin hemolytic activity in *P. haemolytica* and to demonstrate the nonpolar character of the mutation in the lktC$^-$ strain, the lktC plasmid, pNF2232, was used to complement the mutation. Plasmid pNF2232, carrying a functional lktC gene, restored hemolytic activity to the lktC mutant, while pNF2176 did not. These results indicate that mature leukotoxin is required for the hemolysis observed in wild-type *P. haemolytica* strains.

EXAMPLE 11

Leukotoxin Production by lktC$^-$ Strain

As the results described in Example 10 indicated that the hemolytic phenotype was restored in the lktC$^-$ strain by trans-complementation, it was hypothesized that proleukotoxin (proLktA) was produced by strain SH1562. In this Example, immunoblotting was conducted to verify that the mutant strain produced and secreted proLktA.

In this Example, various antibody preparations were used, including convalescent polyclonal bovine antibodies and murine monoclonal antibodies from hybridomas MM601 (neutralizing), MM602 (neutralizing), MM603 (non-neutralizing), and MM605 (non-neutralizing) (See, Gentry and Srikumaran, Microbial Pathogen., 10:410–417 [1991]). The bovine convalescent serum was obtained from a feedlot heifer that had recovered from pneumonic pasteurellosis (provided by Cactus Feeders, Dumas, Tex.). Serum from this animal was previously shown to recognize a specific set of protein antigens in whole cell extracts and supernatants of *P. haemolytica* (See, Highlander et al., DNA Cell. Biol., 8:15–28 [1989]). The murine antibodies were obtained from S. Srikumaran (University of Nebraska).

*P. haemolytica* strains were grown at 37° C., with rotatory shaking to an $OD_{600nm}$ of 1.0 in BHI broth. Preparation and immunoblotting of culture supernatants and cell lysates was performed as described by Highlander et al. (Highlander et al., DNA Cell. Biol., 8:15–28 [1989]) with cell lysates being concentrated 10-fold with respect to supernatants. Whole cell lysate samples were prepared by mixing one volume of cell lysate with 1 volume of 2× SDS-reducing dye (125 mM Tris hydrochloride, pH 6.8, 10% β-mercaptoethanol, 4.5% SDS, 20% glycerol, and 0.005% bromphenol blue). Supernatants from mid-log phase cells were filtered through 0.45 $\mu$m filters, and mixed with one volume of 2× SDS reducing dye. Samples were boiled and then electrophoresed on SDS gels (7.5% polyacrylamide), as known in the art (See e.g., Laemmli, Nature 227:680–685 [1970]). The separated proteins were then electroblotted to nitrocellulose. The blotted proteins were probed with monoclonal mouse antibodies (MM601, MM602, MM603, and MM605) or with polyclonal bovine convalescent serum. Immune complexes were detected with biotin-conjugated goat anti-murine or goat anti-bovine antibodies (Kirkegaard and Perry Laboratories), followed by horseradish peroxidase conjugated streptavidin and 4-chloro-1-naphthol (Sigma).

Figure 6A:
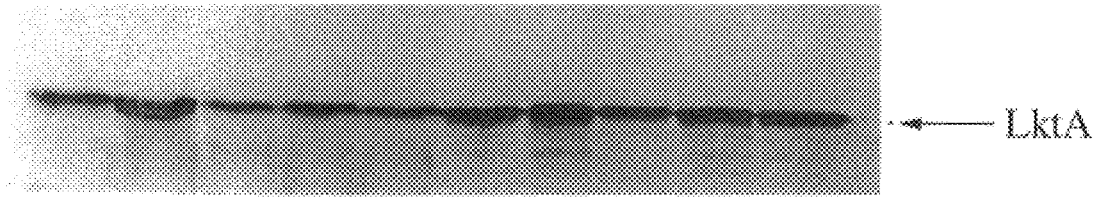
Figure 6B:
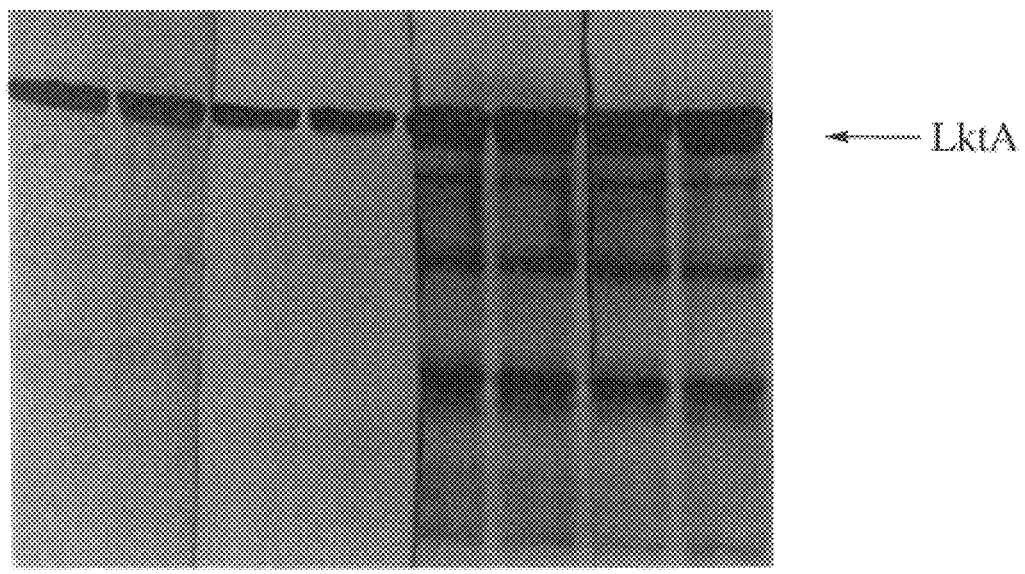
Figure 7:
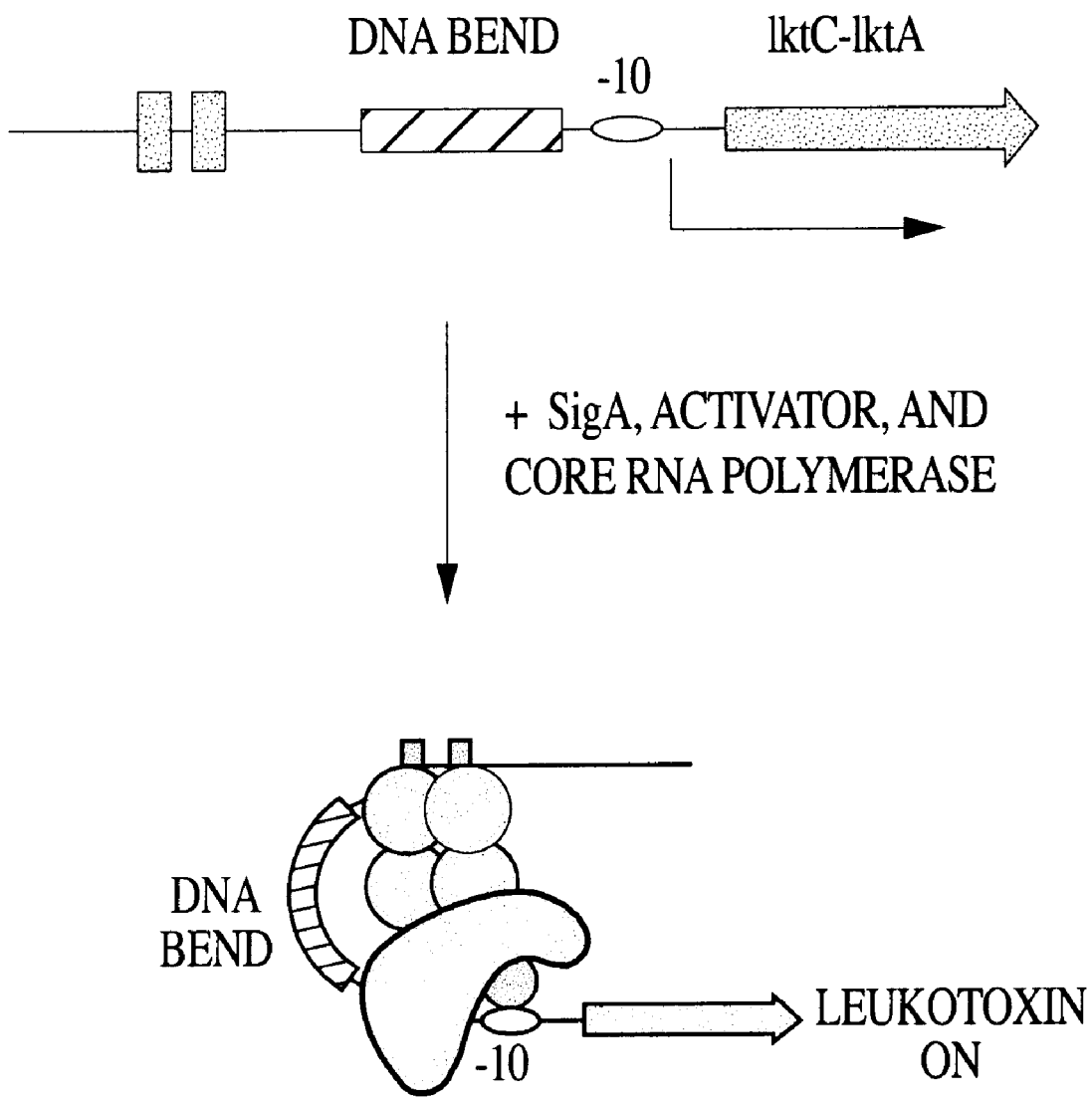

The 102 kD protein corresponding to leukotoxin was detected with the bovine convalescent serum both in supernatants and cell lysates from all *P. haemolytica* strains examined, including the wild-type strain, the mutant strain carrying the pNF2176 vector, the mutant carrying the complementing lktC plasmid, pNF2232, and the mutant, alone. The results are shown in FIG. 6 ("LktA" indicates the position of the leukotoxin protein). Panel A is a blot developed with convalescent bovine antiserum, with lanes 1–5 containing supernatants, and lanes 6–10 containing whole cell lysates of *P. haemolytica*. Lanes 1 and 6 contained SH1562 (lktC); lanes 2 and 7 contained SH1562 carrying pNF2232; lanes 3 and 8 contained SH1562 carrying pNF2176; lanes 4 and 9 contained SH1217 (wild-type); and lanes 5 and 10 contained SH1217 carrying pNF2176. Panel B contains blotted proteins from supernatants of the wild-type (lanes 1, 3, 5, and 7), and lktC mutant strains (lanes 2, 4, 6, and 8) that were developed with antibodies MM605 (lanes 1,2), MM603 (lanes 3,4), MM601 (lanes 5,6), and MM602 (lanes 7,8).

The result indicated that the lktC$^-$ mutation did not significantly affect expression or secretion of the proleukotoxin, because all the strains produced and secreted the proteins at approximately the same level. These results also demonstrate that inactive proLktA can be efficiently secreted from the cells. The relative electrophoretic mobility of LktA and proLktA was similar in this gel system, and more protein was observed in the supernatants than in whole cell samples. Since the inactivation of lktC leads to the production of inactive toxin, it was of interest to determine if neutralizing monoclonal antibodies directed against the toxin would react with the proleukotoxin.

Immunoblot analysis of supernatants from wild-type and mutant strains using murine monoclonal antibodies (FIG. 6, Panel B) confirmed the results obtained with convalescent serum (FIG. 6, Panel A), and demonstrated that proLktA is recognized by leukotoxin-neutralizing antibodies MM601 and MM602. Thus, the neutralizing epitope is not restricted to the acyl group(s) on the mature toxin. The large number of lower bands observed using MM603 and MM605 are likely to be proteolytic products of the toxin.

EXAMPLE 12

BL-3 Cytotoxicity Assays

*P. haemolytica* leukotoxin causes lysis of ruminant macrophages and other leukocytes (Shewen and Wilkie, Amer. J. Vet. Res., 46:1212–1214 [1985]). Sub-cytotoxic levels of leukotoxin may also impair pulmonary defenses and induce inflammatory responses (Confer et al., Can. J. Vet. Res., 54:S48–S52 [1990]). As LktC is required to activate proLktA, it was hypothesized that proLktA, secreted by strain SH1562, would not be cytotoxic. Thus, in this Example, the leukotoxic activity of culture supernatants from mutant, wild-type and trans-complemented *P. haemolytica* strains was investigated using cultured bovine lymphosarcoma (BL-3) cells (Clinkenbeard et al., Infect. Immun., 57:420–425 [1989]; and Waurzyniak et al, Amer. J. Vet. Res., 55:1267–1274 [1994]).

*P. haemolytica* leukotoxin was prepared from cultured supernatants, as follows. Strains were grown at 37° C. with rotatory shaking to mid-logarithmic phase ($OD_{600\ nm}$ of 1.0) in BHI broth, cells were then collected by centrifugation and resuspended in RPMI-1640 medium (Sigma), containing 3.5% bovine serum albumin, to an $OD_{600\ m}$ of 0.25. Cultures were incubated at 37° C. with shaking to an $OD_{600\ nm}$ of 1.0, and the cells were pelleted by centrifugation at 12,000×g for 30 minutes. The supernatant fluids were collected and filtered through 0.2 mm cellulose acetate filters, and stored at −80° C.

Leukotoxic activity was measured by leakage of LDH (lactate dehydrogenase) from bovine lymphosarcoma cells (BL-3; CRL 8037, ATCC), as described by Clinkenbeard et al. (Clinkenbeard et al., Infect. Immun., 57:420–425 [1989]). Briefly, BL-3 cells were resuspended in RPMI-1640 medium (5×10$^5$ cells/ml) and exposed for 2 hours at 37° C. to *P. haemolytica* culture supernatants from different strains, in a total volume of 250 μl. After incubation, unlysed cells were collected by centrifugation (2 minutes, 5,700×g), and the supernatants were assayed for LDH spectrophotometrically at 340 nm, and at 25° C., using a commercial LDH substrate reagent (LD-L50, Sigma). One toxic unit (TU) is the amount of leukotoxin that caused 50% leakage of the total LDH activity from 5×10$^5$ BL-3 cells in 250 μl of RPMI-1640 medium after 2 hours of incubation at 37° C. In controls for maximal leakage of LDH, 0.1% Triton X-100 was substituted for culture supernatants in the incubation mixture. Spontaneous leakage was determined from BL-3 cells incubated with RPMI-1640 medium alone.

Supernatants from logarithmic cultures of *P. haemolytica* wild-type strain contained 180 units of leukotoxic activity per ml, and a supernatant from the trans-complemented strain contained 60 units per ml. No leukotoxic activity was observed in supernatants from the mutant strain SH1562 (−10 units/ml), while Triton X-100 treatment yielded 300 cytotoxic units per ml. These results provide definitive evidence that expression of lktC is required for production of active leukotoxin by *P. haemolytica*. However, the failure to achieve full complementation in the mutant was unexpected since the vector was estimated to be present at 10–20 copies per cell and the complemented strain produces wild-type levels of LktA.

EXAMPLE GROUP III

In the following set of Examples (Examples 13–21), compositions and methods for the over-expression of inactive leukotoxin are described. It is contemplated that these preparations will find widespread use as vaccine preparations against *P. haemolytica*. As with the other examples, DNA and protein sequences were analyzed using the Intelligenetics (Mountain View, Calif.) and University of Wisconsin Genetics Computer Group (GCG) suites of sequence analysis programs. Protein identities and similarities were calculated using the BestFit algorithm. Database searches were performed using the BLAST algorithm, at the National Center for Biotechnology Information, using the GENINFO® Experimental BLAST Network Service.

Transcription of the leukotoxin gene cluster is regulated by an upstream activation system modeled in FIG. 7. This Figure shows the structures involved in production of leukotoxin, including a potential looped DNA structure that involves RNA polymerase holoenzyme (shaded) and an activator protein (open circles) bound to the upstream activator DNA repeats (filled boxes). The static DNA bend is indicated by the striped boxes.

The leukotoxin transcript initiates 30 base pairs (bp) upstream of the lktC start codon (See, FIG. 8), at one of two cytosine residues. An *E. coli*-like RNA polymerase $\sigma^{70}$ "extended-10" region (See, Keilty and Rosenberg, J. Biol. Chem., 262: 6389–6395 [1987] for a description of this region), with the sequence TGTTATAATT, lies 5 bp upstream from the start-site, but no consensus −35 region is observed. Such an arrangement is found in $\sigma^{70}$-dependent promoters that require enhancer proteins for full activity (See, Keilty and Rosenberg, supra; and Kumar et al., J. Mol. Biol. 232: 406–418 [1993]). A static DNA bend is centered at −70 bp with respect to the start-site, and deletion of the DNA bend decreases leukotoxin transcription two-fold, when measured using operon fusions in E. coli (Highlander and Weinstock, DNA Cell Biol. 13: 171–181 [1994]). Three repeats of sequence, TGT-N$_{11-12}$-ACA (SEQ ID NOS: 7 and 8) were located 5' to the DNA bend region; two TGT-N$_{11}$-ACA repeats were protected from DNase I cleavage by a Pasteurella-specific protein, indicating that these are protein-recognition sequences. Identification of these putative regulatory elements was followed by the determination of whether leukotoxin transcription is regulated by an upstream activation system that could require DNA bending to permit contact between an activator bound at the upstream activator sequences (UASs) and RNA polymerase bound at the promoter.

Figure 8:
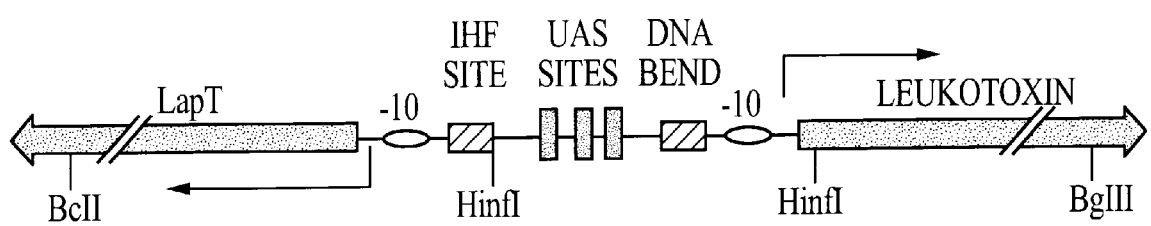

In addition, a divergently transcribed gene encoding a periplasmic arginine binding protein, LapT, maps immediately upstream of the leukotoxin promoter region (FIG. 8). The lapT transcript initiates 27 bp upstream of the start codon and begins at a cytosine residue. This promoter is preceded by a putative IHF (integration host factor) binding site and could also share interactions with the UASs. Although it is not needed for an understanding of the present invention, it is contemplated that because of their proximity and organization, it is possible that the two divergent promoters are coordinately regulated.

These experiments began with an investigation of leukotoxin expression in E. coli. As described below, an activator of leukotoxin transcription (AlxA) that causes a 4- to 5-fold enhancement of leukotoxin transcription in E. coli was isolated. The activator locus (alxA) was mapped and sequenced (GenBank accession number U46781; See, SEQ ID NO:6), and its activity was quantitated by measuring lktC-lacZ expression in E. coli, when expressed in trans. The activator gene is part of a continuous open reading frame that includes the hsdM methylase gene of the P. haemolytica type I restriction-modification system. In this Example, DNA subcloning and manipulation, preparation of chromosomal DNA and Southern blotting were as described in previous Examples.

Bacterial strains and plasmids used in these experiments are listed in Table 2. E. coli strains were grown, at 37° C., in L broth or on L agar (See e.g., Miller, Experiments in Molecular Genetics, Cold Spring Harbor Laboratory, Cold Spring Harbor, N.Y. [1972]), and P. haemolytica strains were grown at 37° C. in Brain Heart Infusion broth BHI (Difco). Antibiotics were added to the following levels when appropriate: ampicillin, 20 µg/ml; chloramphenicol, 30 µg/ml; tetracycline, 15 µg/ml. When needed, X-Gal (5-bromo-indolyl-β-D-galactoside) was added to agar plates to 40 g/ml. The P. haemolytica BamHI cosmid library (See, Highlander et al., Infect. Immun., 61:3942–3951 [1993]) and operon fusions (Highlander et al., DNA Cell Biol., 13:171–181 [1994]) have been described previously. E. coli competent cell preparation and electroporation were as described in previous Examples.

TABLE 2

Bacterial Strains and Plasmids

| Strains | Sources/Characteristics |
|---|---|
| KK2186 | E. coli endA1 hsdR supE sbc15 thi strA Δ(lac pro) [F' traD36 proAB lacIqZΔM15] |
| SH368 | MC4100 Δ(gal-G$^λ$)b2$^λ$::[Φ(lktC-lacZ$^+$) 274 bp HinFI lacY$^+$] |

TABLE 2-continued

Bacterial Strains and Plasmids

| Strains | Sources/Characteristics |
|---|---|
| SH370 | MC4100 Δ(gal-G$^λ$)b2$^λ$::[Φ(lktC-lacZ$^+$) 1.4 bp BclI-BglI lacY$^+$] |
| PHL101 | Pasteurella haemolytica, serotype A1 |
| PHL036 | Pasteurella haemolytica, serotype A1 |
| PHL194 | Pasteurella haemolytica, serotype A1 |
| PHL195 | Pasteurella haemolytica, serotype A1 |
| PHL199 | Pasteurella haemolytica, serotype A1 |
| PHL200 | Pasteurella haemolytica, serotype A1 |
| PHL203 | Pasteurella haemolytica, serotype A1 |
| PHL211 | Pasteurella haemolytica, serotype A1 |
| PHL213 | Pasteurella haemolytica, serotype A1 |
| PHL228 | Pasteurella haemolytica, serotype A1 |
| GE3116 | Pasteurella haemolytica, serotype A1 |
| ATCC 7228 | Pasteurella multocida |
| pLAFRX | RK2 replicon, λcos, T$_c^R$ |
| pSH2001 | pLAFRX::20 kb BamHI |
| pBCKS+ | 3.4 ColE1, fl$^+$, Cm$^R$ |
| pSH2006 | pBCKS+::5 kb EcoRI from pSH2001, orientation B |
| pH2007 | pBCKS+::5 kb EcoRI from pSH2001, orientation A |
| pH2013 | pBCKS+::0.5 kb DraIII from pSH2001, orientation B |
| pSH2014 | pBCKS+::0.5 kb DraIII from pSH2001, orientation A |
| pSH2021 | p2006 ΔEcoRI-DraIII |
| pSH2024 | pBCKS+::1.16 kb XmnII from pSH2001, orientation A |
| pSH2025 | pBCKS+::1.16 kb XmnII from pSH2001, orientation B |
| pSH2026 | pBCKS+::1.28 kb XmnII from pSH2001, orientation B |
| pSH2030 | pBCKS+::8.3 kb XmnII from pSH2001, orientation B |

EXAMPLE 13

Identification of an Activator of Leukotoxin Transcription

In this Example, an lktC-lacZ operon fusion was used as a reporter system to screen a BamHI cosmid library of P. haemolytica DNA for members that could influence leukotoxin transcription in E. coli. Since expression of the leukotoxin promoter is weak in E. coli, it was expected that activators of leukotoxin transcription could be identified by using this method. For screening purposes, the chromosomal operon fusion strain SH370 was used (Highlander and Weinsock, DNA Cell Biol., 13:171–181 [1994]). SH370 carries the 1.4 kb BclI to BglII fragment (FIG. 8) that contains the leukotoxin promoter plus 117 codons (70%) of the lktC reading frame; it also includes an additional one kilobase (kb) of sequence 5' to the primary start site for leukotoxin transcription. This 5' region includes the promoter and 90% (211 of 237 codons) of the divergently transcribed lapT periplasmic arginine binding protein gene (See e.g., Highlander et al., Infect. Immun., 61:3942–3951 [1993]). In FIG. 8, transcriptional start sites for lkt and lapT are indicated by the arrows, the static DNA bend, and putative IHF binding site are shown as striped boxes, and the potential sites for upstream activator protein binding are marked by filled boxes.

Because strain SH370 grew poorly when leukotoxin transcription was activated (described below), a second operon fusion strain, SH368 (Highlander and Weinstock, supra), was used to assay β-galactosidase activity. SH368 carries the 274 bp HinfI fragment that includes sequences from −270 to +4 with respect to the LktC protein start codon. This fusion contains the primary leukotoxin promoter, the DNA bend region, and the putative UAS sites for enhancer binding (See, FIG. 8). It does not include the divergent lapT promoter and does not encode truncated LktC and LapT proteins, as does fusion SH370.

Figure 9A:
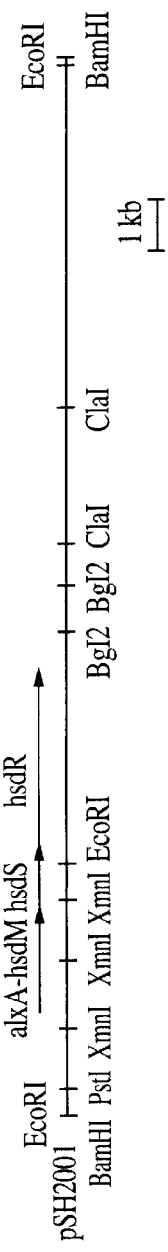
Figure 9B:
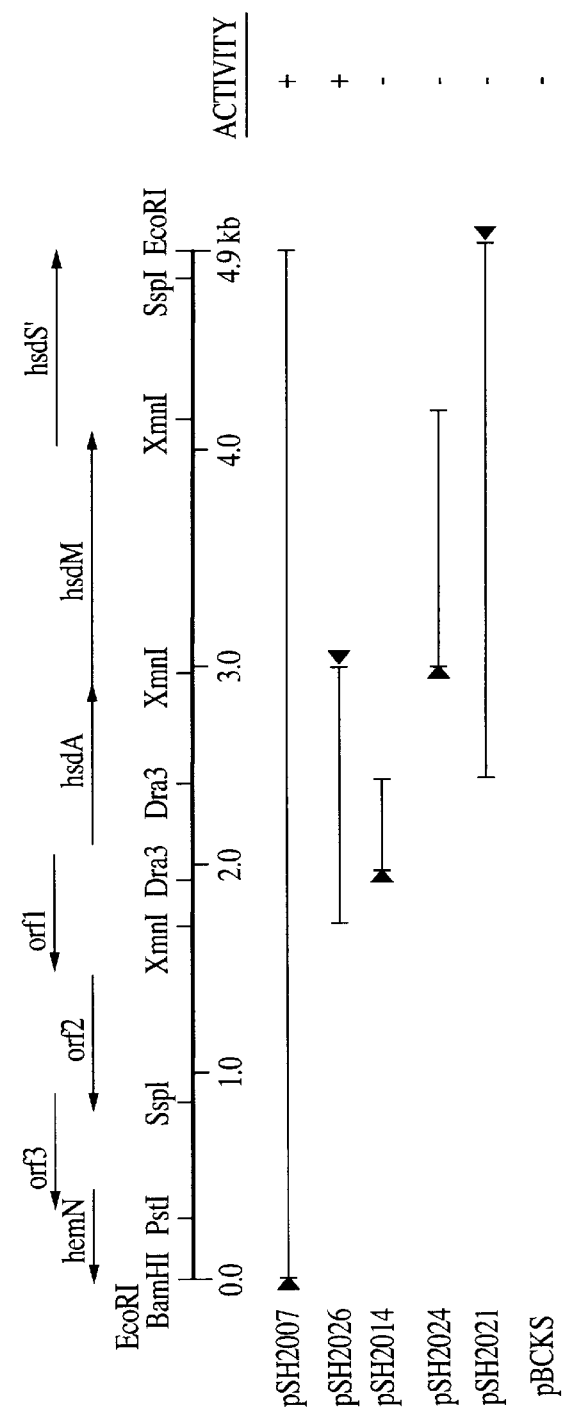

A pLAFRX cosmid library was transduced into strain SH370 and transductants were plated on agar containing X-Gal. In a representative screen, approximately 3000 transductants were tested. Most colonies were medium blue in color, as is the fusion strain in the presence of the pLAFRX vector alone. Twelve colonies with color phenotypes that differed from the fusion alone were picked, streaked to purify, and their DNAs were analyzed. By limited restriction mapping, the twelve isolates fell into one of seven groups. Transduction of cosmid DNA from each into strain SH370 reproduced the colony coloration and morphology observed in the primary screen: three were darker blue than the original fusion, one was white, and three displayed a mixed phenotype, with the colonies having a dark blue center and white perimeter. One of the cosmids that conferred the darker blue phenotype on strain SH370 was called "pSH2001," this plasmid was chosen for further characterization as described below. An abbreviated restriction map of pSH2001 is shown in FIG. 9, Panel A. In FIG. 9, only the relevant restriction sites are shown.

The remaining two transductants that produced the dark blue phenotype had restriction patterns that were unique, in comparison with pSH2001. One of these likely carries the *P. haemolytica* lacZ gene since it produced dark blue colonies on X-Gal agar when transduced into *E. coli* MC4100 (ΔargF-lac). The remaining cosmid appears to encode a protein that binds to the UASs.

EXAMPLE 14

Mapping the Activator Locus

To identify the region of pSH2001 responsible for the activation observed in the phenotypic screen, fragments of pSH2001 were subcloned into the chloramphenicol resistant plasmid, pBCKS+. The resulting plasmids were then transformed into operon fusion strains and tested for color change on plates containing X-Gal (FIG. 9, Panel B). In this Figure, only the relevant restriction sites are shown. Horizontal lines below the restriction map indicate DNA fragments carried on the pBCKS+ vector. Triangles mark the position of the lac promoter on the vector, with respect to the inserted fragment. Potential open reading frames are drawn above the restriction map. Activator function (i.e., as determined by observation of colony color on X-gal containing plates), is indicated by a "+" or "−" sign in the column on the right under "Activity."

Plasmids carrying the 5 kb EcoRI fragment of pSH2001 (pSH2006 or pSH2007) conferred a dark blue phenotype on strain SH370. Plasmid pSH2026, carrying the internal 1.28 kb XmnI fragment, also conferred a dark blue color, while plasmids pSH2014, pSH2024 and pSH2021 did not. This led to the conclusion that the activator function mapped within the 1.28 kb XmnI fragment of the original cosmid, pSH2001. A plasmid carrying the 1.28 kb XmnI fragment in the opposite orientation of insertion, where transcription would be driven by the lac promoter, was not obtained during the cloning process, implying that overexpression of its gene product(s) may be lethal to the cell. Expression of the activator function from pSH2026 indicated that the XmnI fragment carries an active promoter. In the presence of pSH2006, pSH2007, or pSH2026, very small colonies were formed, also suggesting that the cloned fragment encoded a toxic gene product; small colony morphology was also observed in standard *E. coli* cloning strains such as JM105. In strain SH370, both dark blue and light blue colonies were observed. Plasmids encoding the activator function were so unstable in SH370 that it was difficult to reisolate the original plasmid following overnight growth in broth culture. In view of these results, further characterization was done using strain SH368.

EXAMPLE 15

Figure 10:

Restriction Fragment Length Heterogeneity Within the Region Encoding the Activator While subcloning and developing a restriction map for pSH2007, size heterogeneity within the central 450 bp DraIII fragment was observed. Agarose gel electrophoresis indicated that the fragment contained DNA insertions varying from 50 to 150 bp in size; this was confirmed by DNA sequence analysis (see below). Stable subclones were those that had acquired the insertions. It seemed likely that the mixed light blue/dark blue colony color, seen in SH370 carrying plasmids such as pSH2007, was the result of DNA sequence changes that disrupted the locus responsible for the activation phenotype. To verify that the pSH2001 fragment had not undergone a gross rearrangement during the cloning process, chromosomal fragment lengths were analyzed, by Southern blotting. Approximately 1 μg of *P. haemolytica* plasmid or chromosomal DNA was digested with XmnI, separated on an agarose gel and blotted, as described in previous Examples. In this experiment, the 4.0 kb SspI fragment (See, FIG. 9, Panel B) was used as a probe. The results are shown in FIG. 10. In this Figure, lane a contains pSH2001; lane b contains pOG2030; lane c contains PHL101; lane d contains GE3116; lane e contains ATCC 7228 (*P. multocida*); lane f contains PHL036; lane g contains PHL194; lane h contains PHL195; lane i contains PHL199; lane j contains PHL200; lane k contains PHL203; lane l contains PHL211; lane m contains PHL213; and lane n contains PHL228. DNA fragment lengths, predicted from the DNA sequence are indicated to the left of the blot.

As shown in FIG. 10, identical 1.28 and 1.16 kb XmnI fragments were detected in the original *P. haemolytica* cloning strain, PHL101, in the cosmid clone pSH2001, and in a pSH2001 subclone, pOG2030 (See, Highlander and Garza, Gene 178:89–96 [1996]). When additional *P. haemolytica* A1 strains were probed, fragments varying from 1.16 kb to 1.28 kb were observed in place of the 1.28 kb XmnI fragment seen in PHL101 (i.e., lanes d, f, h, j, l, m, and n); the 1.16 XmnI fragment was constant in all strains. In some, a third, minor fragment at about 1.35 kb was also observed (i.e., lanes f, h, j, m and n).

No hybridizing DNA was observed when *Pasteurella multocida* DNA was probed (i.e, lane e). These observations suggest that small insertions or deletions occur within the 1.28 kb XmnI fragment both on plasmids, and on the chromosome of *P. haemolytica*. This was likely to be a consequence of changes in numbers of a pentanucleotide repeat within the activator gene, as described below.

EXAMPLE 16

Activator Locus-Induced Increased Leukotoxin Transcription in *E. coli*

Figure 11:
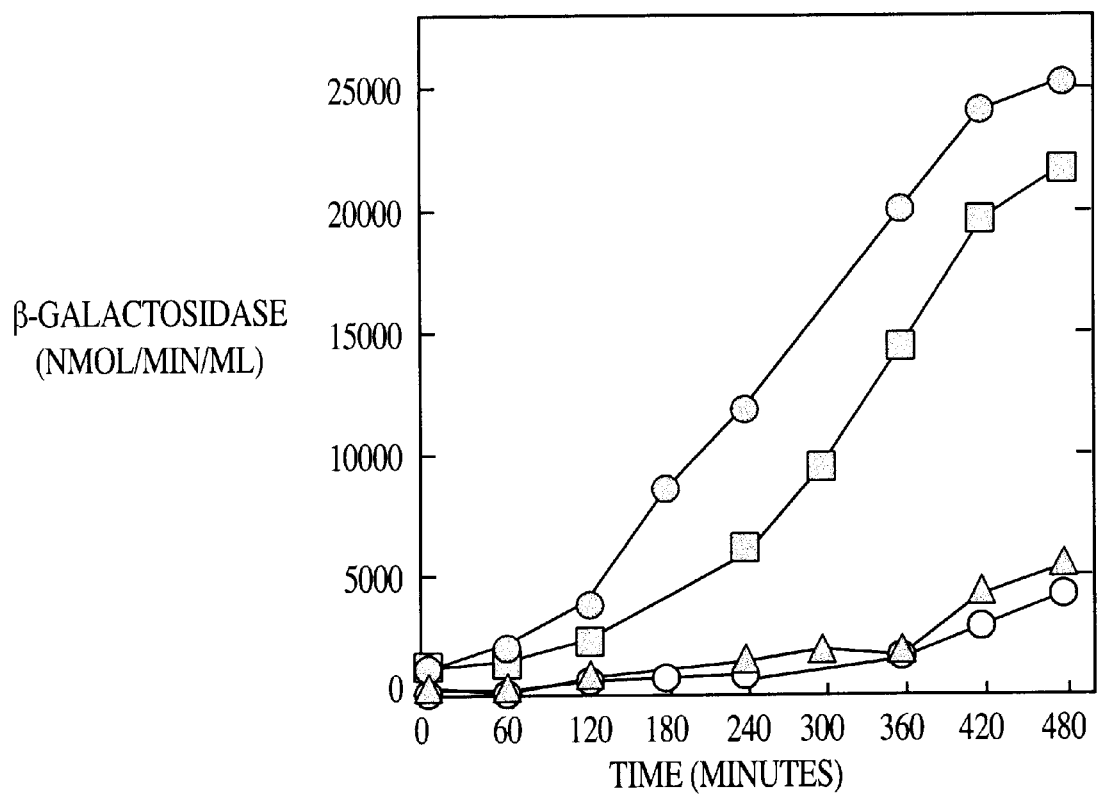

In this Example, transcriptional activation by plasmid subclones was quantitated by measuring β-galactosidase activities in strain SH368. The β-galactosidase activities of operon fusion strains was determined using the method of Miller (Miller, supra), as described by Weisemann et al., (Weisemann et al., J. Bacteriol., 160:112–121 [1984]). The results are shown in FIG. 11. In this Figure, the filled circles indicate the results for pSH2007, while the filled squares indicate the results for pSH2026, filled triangles indicate the results for pSH2021, and open circles indicate the results for PBCKS+; the units are reported as nmol β-galactosidase mini$^{-1}$ min$^{-1}$, and "time" represents minutes of growth of freshly diluted (1/20) overnight culture.

As shown in FIG. 11, plasmid pSH2007, carrying the entire 5 kb EcoRI fragment, and plasmid pSH2026, carrying the internal 1.28 kb XmnI fragment, increased activity four to five-fold, while pSH2021, carrying the DraIII to EcoRI fragment, did not activate transcription. This result verified that the activator locus maps within the variable 1.28 kb XmnI fragment. β-galactosidase activity was not measured for DraIII subclones, since they were unstable and had acquired small insertions.

EXAMPLE 17

Identification of Open Reading Frames Within a 5 kb Region That Includes the Activator Locus In this Example, the nucleotide sequence of the 5 kb EcoRI fragment and additional flanking DNA was determined. Six open reading frames on pSH2007 were identified (FIG. 9, Panel B) and features of these are listed in Table 3.

TABLE 3

Features of Predicted Peptides Encoded by pSH2007

| Reading Frame | Peptide Length | Predicted Molecular Weight (kD) | Features/Comments |
|---|---|---|---|
| alxA-hsdM | 616 | 69 | Putative cleavage site at Gly-284 |
| alxA | 236 | 37 | STAQH repeats; Leu heptads (4 × 2); Trimer repeats; 61% identity with H. influenzae ORF 5' to hsdM |
| hsdM | 380 | 32 | N-6-methylase signature 74% identity with H. influenzae HsdM |
| hsdS' | 315 | 36 | 38% identity with H. influenzae ORF 3' to hsdM |
| orf1 | 125 | 15 | 44% identity with H. influenzae ORF near ponB 50% identity with ORF near E. coli speED |
| orf2 | 195 | 22 | Acidic 63% identity with H. influenzae ORF near rrn 45% identity with S. typhimurium ORF-171 in polA-gln intergenic region |
| orf3 | 156 | 18 | 22 amino acid signal sequence 49% identity with H. influenzae ORF near rrn |
| hemN' | 145 | 18 | 68% identity with S. typhimurium HemN 30% identity with H. influenzae HemN |

FIG. 12 shows the DNA sequence and predicted amino acid sequences for AlxA and hsdM. In this Figure, nucleotide numbering is indicated on the left and the amino acid numbering for the AlxA-hsdM reading frame is indicated on right, in parentheses. Putative translational signals (ribosome binding sites, start codons, termination) are shown in bold. This Figure shows the position of the termination codons in the plus one and plus two frames at bp 682 and 669, respectively. The STAQH repeats are marked by the dotted underlining, and the hydrophobic heptad repeat regions are marked with solid underlining. A putative signal peptidase cleavage/recognition site is indicated by the wavy underlining and the HsdM N-6-adenine methylase signature is marked with a double underline. In addition, key restriction sites are indicated in italics.

As indicated in FIG. 12, a 616 codon open reading frame initiates within the 0.45 kb DraIII fragment, crosses the XmnI site at 2.9 kb and ends before the XmnI site at 4.1 kb. This reading frame encodes two separate activities. Complementation using the 1.28 kb XmnI fragment on pSH2026 indicates that activator function maps within the amino terminal one third of the reading frame. Sequences homologous to the amino terminal protein sequence were not found in database searches. In contrast, the carboxy-terminal two-thirds of the peptide is very similar to the HsdM methylase subunit of type I restriction-modification enzymes. The associated specificity (hsdS) and restriction (hsdR) subunit genes map downstream of hsdM and methylase activity correlates with the carboxy-terminus of the 616 codon reading frame (See also, Highlander and Garza, Gene 178:89–96 [1996]). Thus, the activator gene, AlxA (i.e., activator of leukotoxin expression), forms the first of a four gene cluster that encodes both transcriptional activation finction and the type I restriction-modification system of P. haemolytica A1.

The predicted peptide encoded by AlxA begins with the pentapeptide repeat, STAQH, which occurs 13 times within the amino terminus of the protein. This is encoded by 39 copies of the pentanucleotide DNA repeat, GCACA. Addition or deletion of a single pentanucleotide repeat, presumably by slipped-strand mispairing across the sequence (See e.g., Levinson and Gutman, Mol. Biol. Evol., 4:203–221 [1987]), causes frame-shifting that results in termination of activator translation at one of two UGA triplets that occur downstream of the repeats (See, FIG. 12). Slipped-strand mispairing across these repeats is likely to be the basis of the fragment length heterogeneities observed in different A1 strains. The STAQH repeat region is followed by two sets of hydrophobic leucine heptad repeat sequences (amino acids 81 to 109, and 145 to 173). Such repeats often constitute leucine zipper domains in eukaryotic and prokaryotic transcription factors. In addition, an overlapping acidic region (amino acids 136–168), characteristic of some transcription factors, was also observed in the AlxA sequence.

The inferred amino acid sequence of AlxA matched a sequence derived by translating the H. influenzae sequences immediately upstream of the proposed hsdM gene (See, Fleischmann et al., Science 269:496–5121 [1995], for a review of the H. influenzae genome). Here, a repeat, CGAGA, occurred only two times (these are not shown in FIG. 12). Two additional pentapeptide repeats were arbitrarily added to restore the frame; this provided a plausible AUG start codon with appropriate ribosome binding sequence that could encode a peptide of 64 kD. Excluding the repeat region, the AlxA-HsdM and H. influenzae protein sequences were found to be 68% identical and 79% similar (including functionally similar amino acid matches) across the entire sequence. As indicated in Table 3, the HsdM peptides are more homologous than are the AlxA proteins, though the AlxA peptides very similar within the leucine heptad and acidic sequences (not shown). The DNA sequences are 69% homologous and maintain the same continuous reading frame (less one codon in the P. haemolytica sequence) across the entire region.

EXAMPLE 18

Identification of AlxA and HsdM Proteins

In this Example, AlxA and HsdM proteins were identified. Trans-activation indicated that the 1.28 kb XmnI fragment was sufficient for AlxA function, yet the 616 codon reading frame traverses the XmnI site. An *E. coli*-like ribosome binding site occurs upstream of the AlxA-hsdM reading frame, but a potential second start site is not apparent within the reading frame (See e.g., FIG. 12).

In vitro transcription and translation were performed to determine if one or more polypeptides were produced from the AlxA-hsdM genes. In vitro transcription and translation was performed using the Prokaryotic DNA-directed Translation Kit from Amersham. Two µg of cesium chloride purified, covalently closed circular DNA template were transcribed and translated using 5 µl of S30 extract, in the presence of 2 µl Trans$^{35}$S-Label ($^{35}$S-methionine, $^{35}$S-cysteine, 10 mCi/ml, 1000 Ci/mmol; ICN). Samples were combined with 0.5 volume 3x SDS-reducing dye (187 mM Tris hydrochloride pH 6.8, 15% β-mercaptoethanol, 6.9% SDS, 20% glycerol, 0.007% bromophenol blue), boiled 5 minutes, then were electrophoresed at 150 volts on an SDS-10% (37.5:1) polyacrylamide gel as known in the art (See, Laemmli, supra). $^{14}$C-labeled protein molecular weight markers were also from Amersham. Following electrophoresis, the gel was treated with En$^3$hance for 60 minutes (Dupont NEN), washed with distilled water for 30 minutes, then dried, and autoradiographed.

Figure 13:
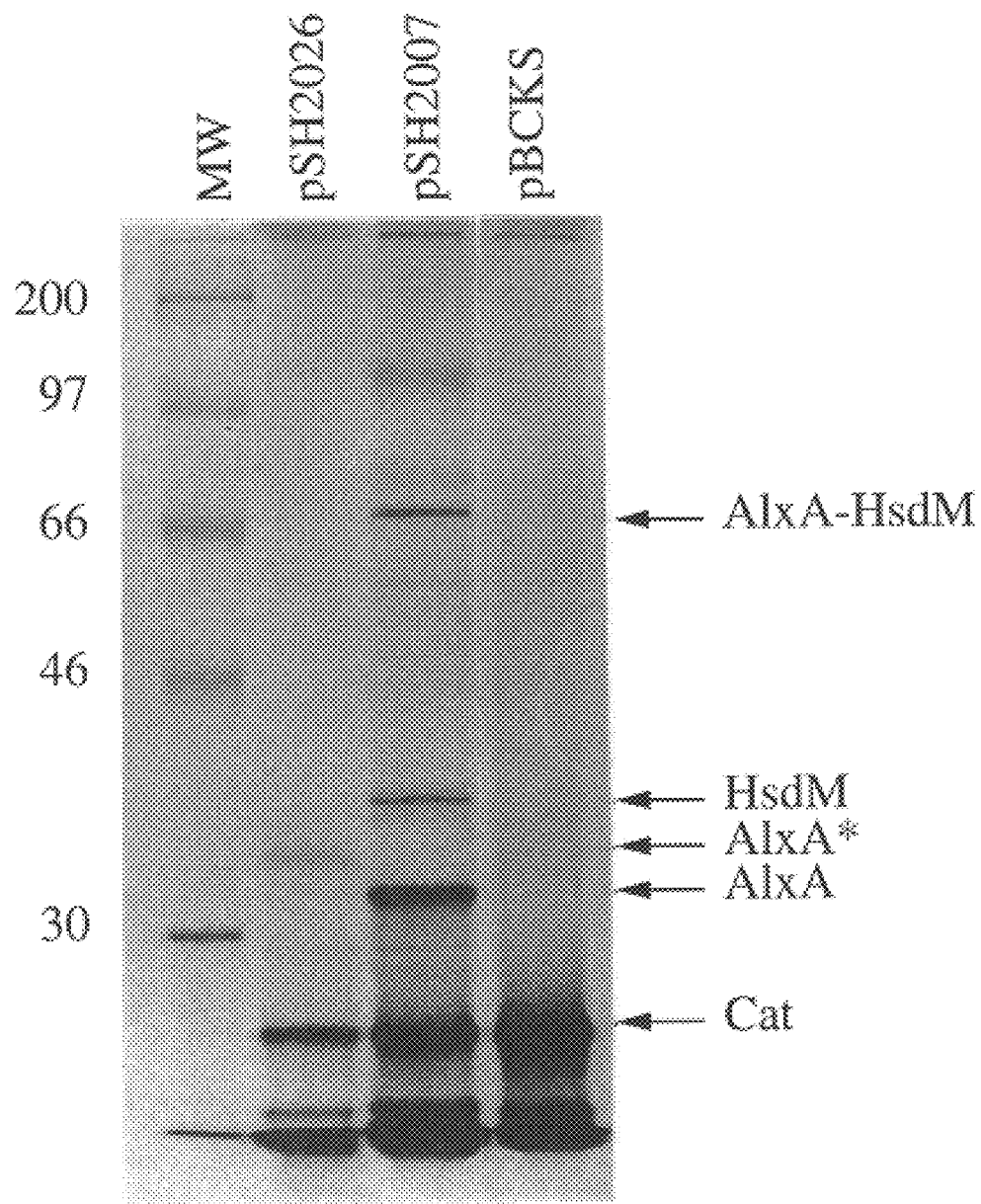

A large peptide of about 72 kD, and two smaller peptides of 38 kD and 31 kD were produced by the EcoRI clone, as shown in FIG. 13. FIG. 13 is an autoradiograph of a 10% SDS-PAGE gel, in which proteins produced in vitro by plasmids pSH2026, pSH2007, and pBCKS are shown. Labelled ($^{14}$C-) molecular weight markers (kD) are shown in the first lane, with "pSH2026" indicating the presence of pSH2026-directed proteins in the second lane, "pSH2007" indicating the presence of pSH2007-directed proteins in the third lane, and "pBCKS" indicating the presence of pBCKS-directed proteins in the last lane. In this Figure, the positions of the AlxA-HsdM polyprotein and the HsdM, AlxA, and chloramphenicol transferase (Cat) proteins are marked by the arrows. The position of an aberrantly processed AlxA protein produced by pSH2026 is indicated by "AlxA*."

The results are consistent with proteolytic processing of a single precursor into 31 kD AlxA and 38 kD HsdM peptides. Peptides of about 20 kD, 18 kD and 15 kD were also resolved using 12% SDS-PAGE gels. These peptides are likely correspond to products of the or*f*2, or*f*3 or hemN', and or*f*1 open reading frames (See, Table 3). A peptide corresponding to the amino terminal portion of HsdS (36 kD expected) was not observed on either the 10% or 12% gels; the truncated peptide may be unstable or the hsdS RNA may be inefficiently translated since it has been found to contain many rare codons.

Further confirmation of the precursor-product relationship between the large peptide and AlxA was revealed when plasmid pSH2026 was used as a template for the in vitro transcription/translation reaction. In this case, a peptide of about 33 kD observed (indicated as "AlxA*" in FIG. 13). This is slightly larger than that produced using pSH2007, suggesting that the appropriate processing site is missing from the peptide encoded by pSH2026. Plasmid pSH2007 produced more AlxA peptide than did pSH2026; this was expected since transcription on pSH2007 can be driven by the lac promoter on the vector. Nevertheless, using pSH2007, the AlxA peptide was more abundant than the polyprotein or HsdM.

EXAMPLE 19

Interaction of AlxA With a Leukotoxin Promoter Fragment

Since AlxA acts as transcriptional activator, gel mobility shift experiments were performed to test whether the protein could interact with the leukotoxin promoter. Cleared whole cell extracts from *E. coli* strains expressing AlxA were used to examine the interaction of AlxA with the 274 bp HinfI fragment (FIG. 8) that carries the leukotoxin promoter.

Crude cell extracts were first prepared and then analyzed for DNA binding. Ten ml cultures of *E. coli* cells, carrying pSH2007, pSH2026, or the pBCKS+ vector, were grown at 37° C., to an OD$_{600}$ of 1.0. Aliquots of one ml of cells were pelleted by centrifugation for 1 minute, 13,000×g at room temperature, then the pellet was resuspended in 100 µl DNA extract buffer (50 mM Tris-HCl, pH 7.5, 1 mM EDTA, and 1 mM dithiothreitol). The cells were disrupted by two bursts of sonication, 10 seconds each, at 50 watts. The extracts were then cleared by centrifugation for 30 minutes at 13,000×g, 4° C. Glycerol was added to 25% to the cleared supernatant, and the extracts were stored at −20° C., until analysis.

In addition, a 274 bp HinfI fragment containing the leukotoxin promoter was end-labeled by phosphate exchange using [γ-$^{32}$P]ATP and T4 DNA kinase (See, Highlander and Weinstock, supra). The 298 bp fragment from the 1 kb ladder (Gibco-BRL) was also end-labeled for use as a negative control. For mobility shift assays, 0.1 µl of crude extract and 1 ng of the labeled promoter fragment were incubated together, for 10 minutes at room temperature, in a 25 µl reaction mixture composed of DNA binding buffer (10 mM Tris, pH 7.5, 100 mM KCl, 1 mM dithiothreitol, and 1 mM EDTA), plus 100 µg/ml bovine serum albumin and 40 µg/ml poly dI·dC. The entire sample was loaded onto a 4% (80:1) polyacrylamide, Tris glycine (25 mM Tris, pH 8.3, 190 mM glycine, and 1 mM EDTA) gel that had been pre-run for 60 minutes at 25 mA with buffer circulation. The DNA binding samples were electrophoresed for 2.5 hours at 35 mA with buffer circulation, then the gel was dried and autoradiographed.

Figure 14:
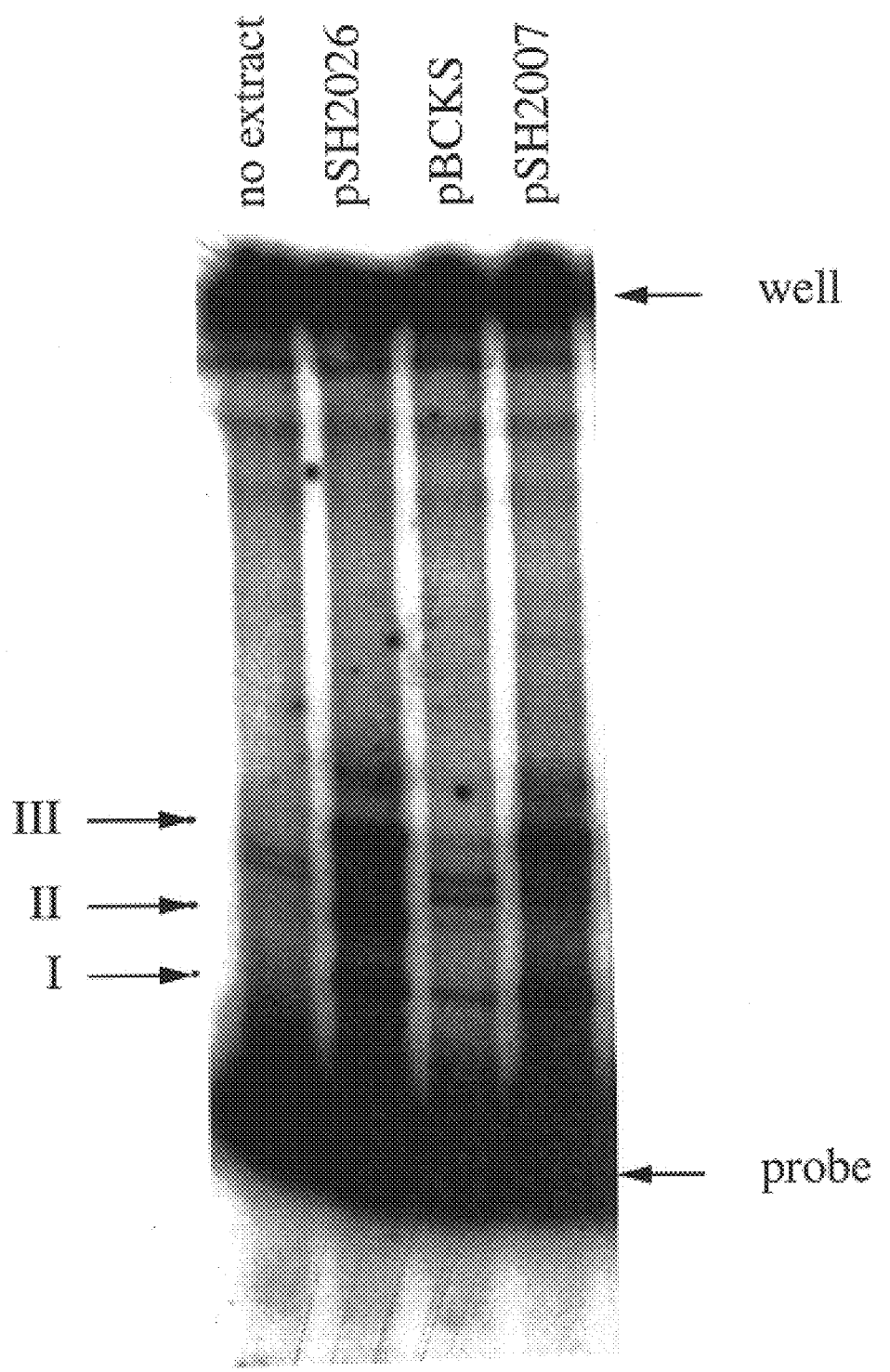

As illustrated in FIG. 14, specific DNA-protein complexes were formed (I, II, III) in the presence of AlxA. In this Figure, the location of the well and the free probe are indicated by arrows on the right side of the gel, and the positions of the three shifted species observed to be most prominent with pSH2006, are marked (I, II, and III) on the left. Extracts from cells carrying pSH2026 yielded three shifted complexes while those from pSH2007 produced only two (complexes I and III). An extract from pBCKS also yielded a small amount of complex I, but the intensity of the signal was not as great as that observed using pSH2026 or pSH2007. A mobility shift was not observed using these extracts with a non-specific probe derived from the Gibco-BRL 1 kilobase ladder. Thus, it appears that AlxA, in crude extracts, can interact with the promoter.

EXAMPLE 20

Alternative Methods for Enhancement of Leukotoxin Expression

In this Example, methods to increase LKTA expression by introducing the AlxA activator, on a multicopy plasmid, into *P. haemolytica* is described. The AlxA gene and its promoter, are cloned onto pNF2176 (See, FIG. 16), and electroporated into both the wild-type and lktC⁻ deletion strains, as described in Example 1.

Following insertion of the *P. haemolytica* fragments into pNF2176, and electroporation into *P. haemolytica*, leukotoxin production of the organisms is quantitated. In the case of increased expression, Northern blots (See e.g., Thomas, Proc. Natl. Acad. Sci., 77:5201–5205 [1980]) are used to assay transcript levels.

However, insertion of an antibiotic resistance cassette may interfere with transcription of the downstream lktA gene. Nonetheless, in the mutant strain, transcription is likely to be driven by the leukotoxin promoter. Thus, in order to overproduce inactive leukotoxin, lktA transcription driven by a strong or inducible P. haemolytica promoter is desirable, since many E. coli promoters don't appear to function in this organism.

EXAMPLE 21

Figure 16:
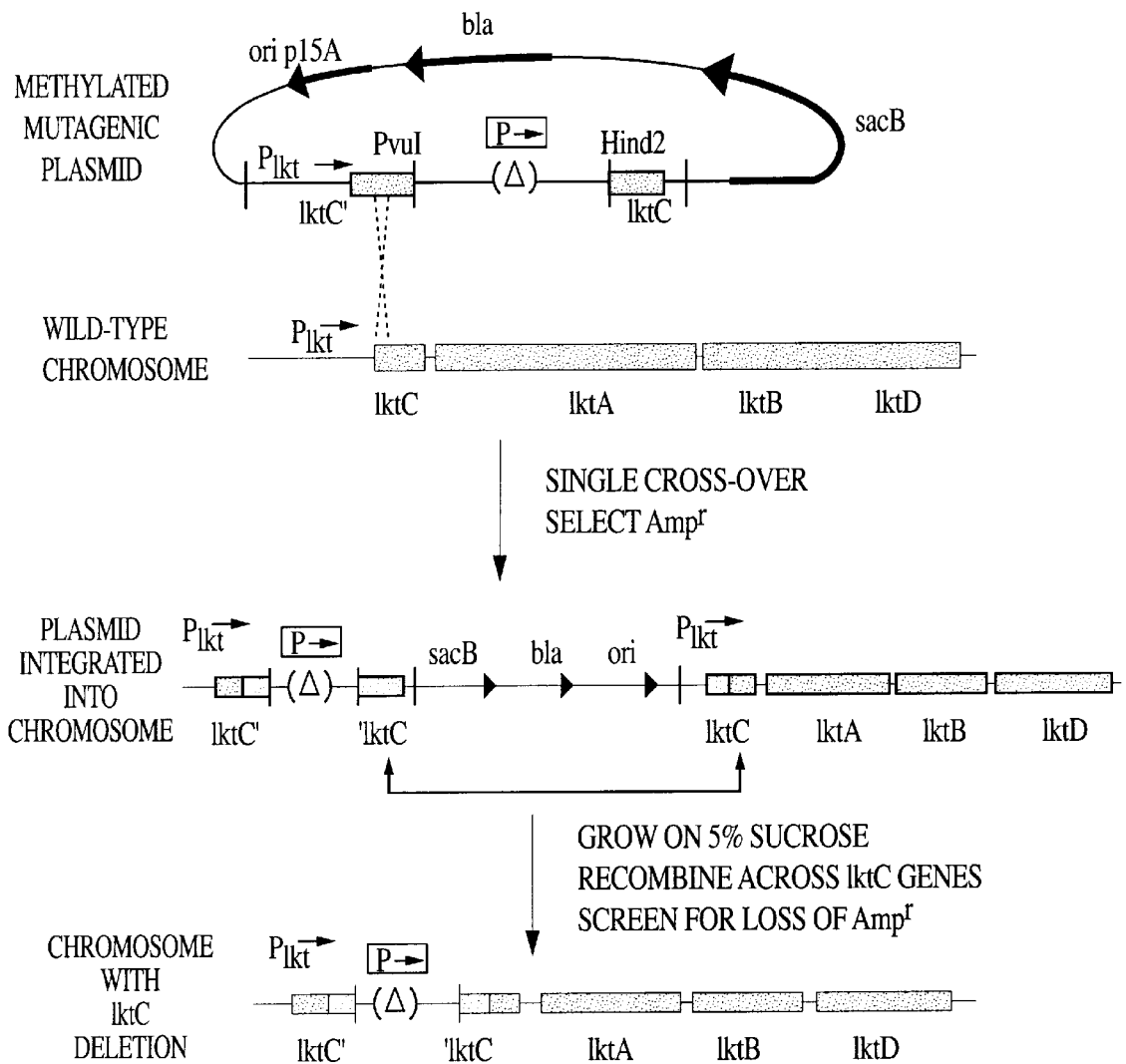

Production of Targeted Chromosomal Deletion of lktC and Insertion of Promoter Upstream of lktA In this Example, a targeted chromosomal deletion of the lktC gene in P. haemolytica, and insertion of a promoter upstream of the lktA gene is created. First, a known strong promoter from the lapT periplasmic binding protein gene (See, Highlander et al., Infect. Immun., 61:3942–3951 [1993]), and a heat-shock inducible promoter from the lapC gene are used. It is contemplated that this latter promoter will provide induction of leukotoxin expression following a temperature upshift. Heat-stable promoter sequences are included in the lktC deletion plasmid, shown in FIG. 16. FIG. 16 shows one embodiment of this method. In this Figure, the promoter upstream of the leukotoxin structural gene lktA is boxed. A deletion in the lktC reading frame is created on a pNF2176 plasmid carrying a marker gene (e.g., the levansucrase gene (sacB)) and the ROB-1 β-lactamase gene in E. coli; a regulated or strong promoter may be inserted in place of the deleted DNA. The DNA is electroporated into P. haemolytica with selection for ampicillin resistance as described in previous Examples; pYFC1 is also introduced as described in previous Examples. Colonies are replicated to plates containing 5% sucrose, and surviving colonies screened by PCR and Southern blotting for recombination/deletion across the 3' ends of the duplicated lktC genes, as known in the art. One resulting strain carries a deletion within the lktC reading frame, and a second strain also contains a promoter to drive lktA transcription.

Figure 17:
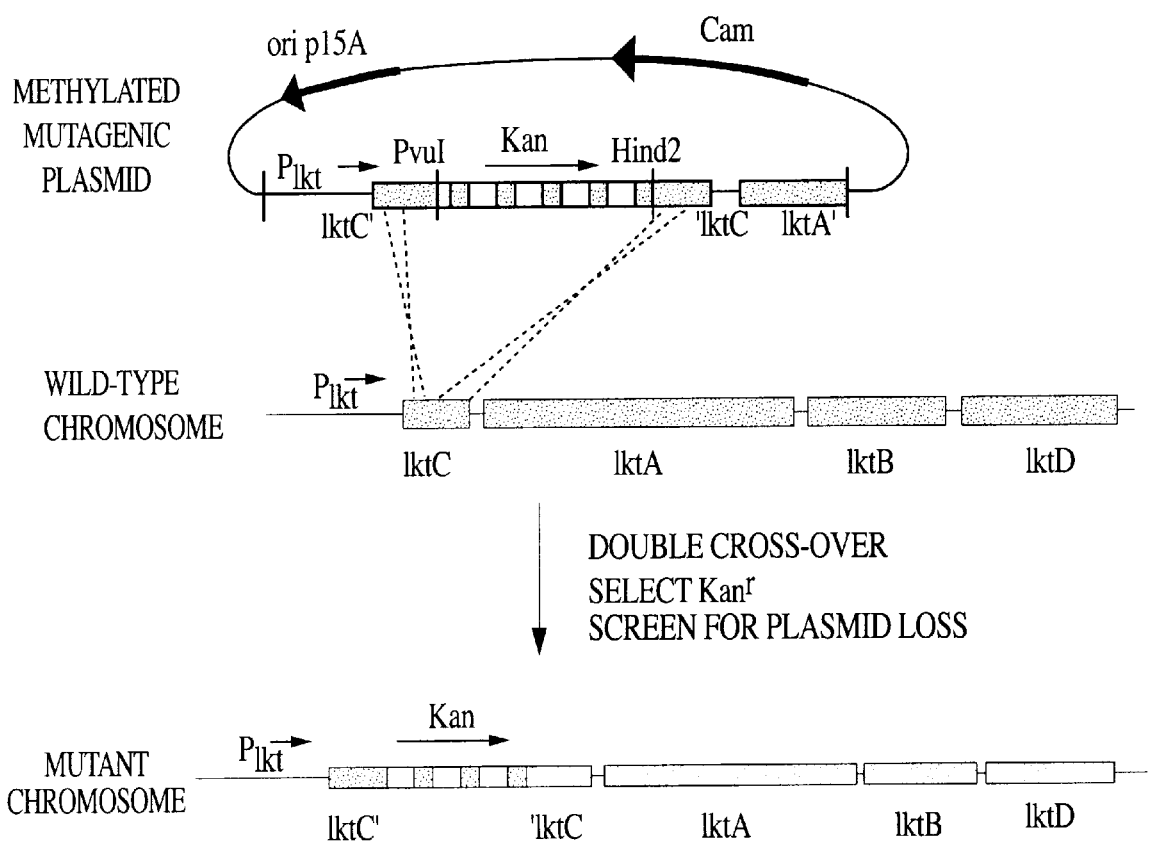

In other experiments, promoters are also cloned downstream from an antimicrobial resistance cassette and introduced onto the chromosome as shown in FIG. 17. In this Figure, one embodiment for producing a targeted allelic replacement of the lktC gene with an insertionally inactivated copy is provided. The kanamycin resistance gene is inserted into the lktC reading frame cloned on a plasmid such as pNF2176 in E. coli. The DNA is electroporated into P. haemolytica, and pYFC1 is introduced as previously described. Kanamycin resistant colonies are then recovered, screened for the loss of vector DNA by colony hybridization, and mapped by Southern hybridization, as known in the art. LktC⁻ strains produced by this method have the kanamycin cassette inserted in the P. haemolytica chromosome as shown in FIG. 17.

Figure 15:
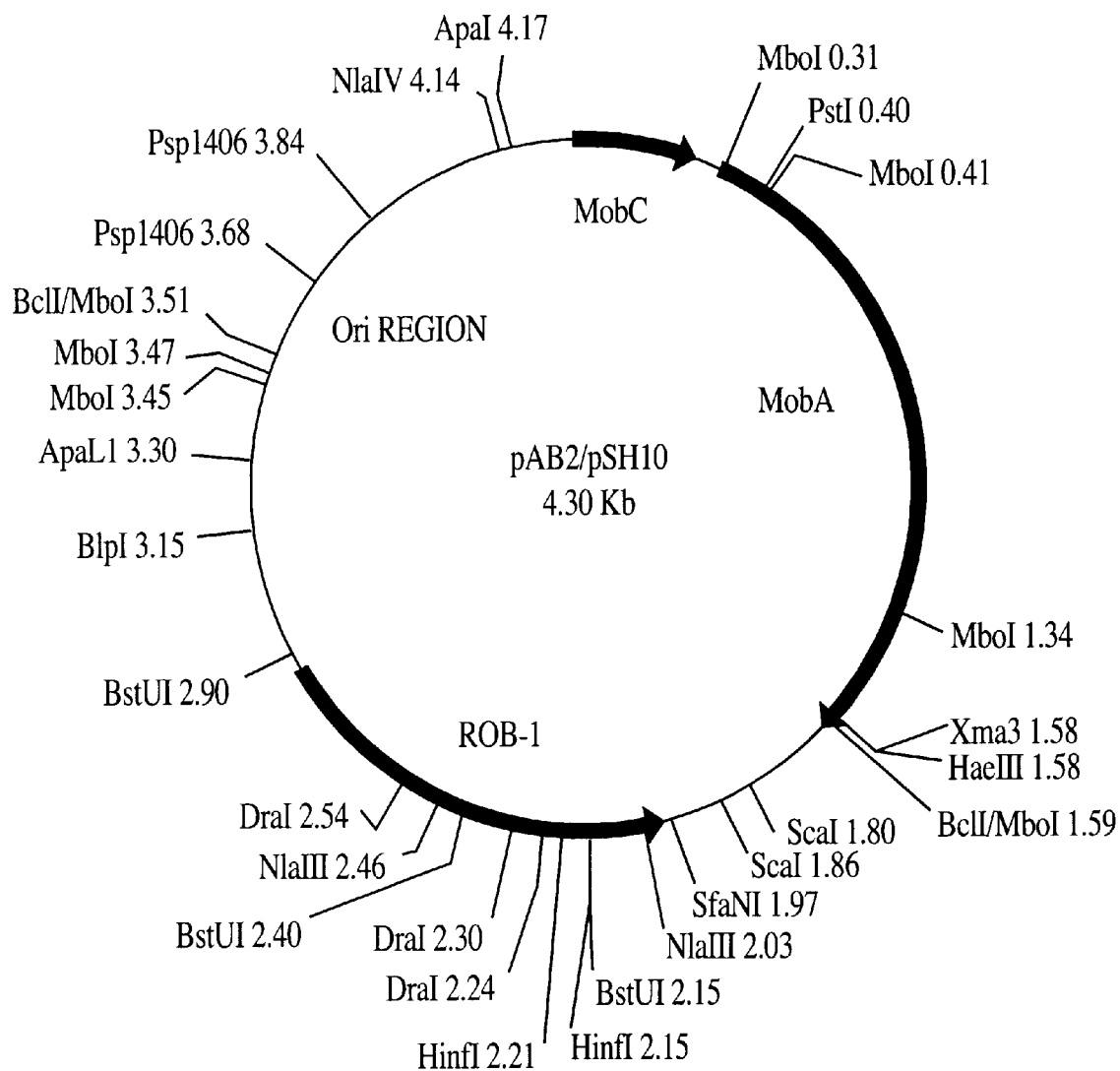

In further experiments, the cat gene on pNF2283 is used to identify additional strong P. haemolytica promoters. Random P. haemolytica DNA fragments are cloned upstream of the cat gene as illustrated in FIG. 15, and cells are selected for growth on high chloramphenicol concentrations (i.e., 100 μg/ml or more). Fragments that enhance expression of the cat gene are analyzed by DNA sequencing and subcloning, to establish that the increased cat activity is due to transcriptional enhancement and not to plasmid copy number increases. These promoters are also introduced onto the P. haemolytica chromosome.

EXAMPLE GROUP IV

In the following Examples (Examples 22–23), methods for the excision of the antimicrobial resistance markers are described. Especially in view of the widespread development of antimicrobial resistance in bacteria of veterinary and medical importance, it is preferable to use vaccine strains of organisms that do not contain antimicrobial resistance genes.

Thus, an LKTC⁻ strain that does not contain an antimicrobial resistance gene is a preferred embodiments of live vaccines against P. haemolytica. FIG. 17, as described above, provides an outline of the approach.

EXAMPLE 22

Production of LKTC⁻ Strain Without Antimicrobial Resistance

In this Example, production of an LKTC⁻ that does not contain an antimicrobial resistance gene is described. As indicated in previous Examples, a deleted copy of the lktC gene were introduced into P. haemolytica on a plasmid that expresses both a selectable antibiotic resistance gene and the Bacillus subtilis sacB (See, Gay et al., J. Bacteriol., 164:918–921 [1985], for a description of the sacB gene). Expression of sacB makes cells sensitive to growth on 5% sucrose, so it can be used as a conditional selection for loss of integrated plasmid DNA. The sacB gene was cloned as a 3.5 kb BamHI fragment from plasmid pBB50 into pNF2176 to create the plasmid pNF2177. pNF2177 was electroporated into SH1217, cells were plated on BHI agar containing 5% sucrose. However, the cells were found to be sucrose-resistant, indicating that the sacB gene was not expressed in P. haemolytica.

EXAMPLE 23

Site-Specific Recombination for Production of Live Vaccines

In this Example, site-specific recombination is described for development of live P. haemolytica vaccines that do not contain antimicrobial resistance genes. In this Example, modules for site-specific recombination of phage λ and transposon Tn1545 are used. Integration of λ into the P. haemolytica chromosome is accomplished by recombination between the λattP and λattB sites using λ integrase. Effective excision of the prophage from the chromosome flanked there by λattL and λattR, is dependent upon the action of λXis and λInt proteins.

A cassette consisting of the kanamycin resistance gene flanked by λattL and λattR was constructed as described in previous Examples. This has been placed in the chromosome of P. haemolytica, using the techniques described in previous Examples. This cassette allows selection of clones with DNA fragment insertions into the P. haemolytica chromosome. In these experiments, the resistance gene is excised upon integration in the presence of the λXis and λInt proteins. This excision is accomplished by the introduction of a helper plasmid carrying the λxis and λint genes into the recombinant P. haemolytica cells. Under the control of a P. haemolytica promoter, these genes provide production of λ excisase and integrase which excises the kanamycin gene from the chromosome, while leaving the lktC inactivated by the insertion of λattP.

In an alternative method, the lktC gene is inactivated using the phage P1 cre/lox recombination system or the Tn1545 transposon system, using methods known in the art and as described in the previous Examples.

It is clear from the above that the present invention provides compositions and methods for the production and use of improved *P. haemolytica* vaccines, as well as *P. haemolytica* plasmids and methods useful for the development of additional strains of veterinary and medical importance for development of improved methods of treatment and/or prevention of pasteurellosis. Indeed, from the above it is clear that the present invention provides compositions and methods for the preparation of effective multivalent vaccines against *P. haemolytica* leukotoxin. It is also contemplated that the recombinant leukotoxin proteins be used for the production of antitoxins.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A whole cell vaccine composition comprising a therapeutically effective amount of recombinant *Pasteurella haemolytica* organism comprising an inactivated lktC gene, wherein said recombinant *Pasteurella haemolytica* organism expresses inactive leukotoxin, wherein and said inactive leukotoxin comprises proleukotoxin.

2. The vaccine composition of claim 1, further comprising a diluent.

3. The vaccine of claim 2, further comprising one or more compounds selected from the group consisting of excipients and adjuvants.

4. The vaccine composition of claim 1, wherein said recombinant *Pasteurella haemolytica* comprises an lktC::cat operon fusion.

5. The vaccine composition of claim 1, wherein said expression of inactive leukotoxin is stably maintained.

6. The vaccine composition of claim 1, wherein said recombinant *Pasteurella haemolytica* contains an activator for expression of said inactive leukotoxin.

7. The vaccine composition of claim 6, wherein said activator is AlxA.

8. The vaccine composition of claim 1, wherein said recombinant *Pasteurella haemolytica* further comprises a strong leukotoxin promoter.

9. A whole cell composition comprising recombinant *Pasteurella haemolytica* organism comprising an inactivated lktC gene, wherein said recombinant *Pasteurella haemolytica* organism expresses inactive leukotoxin, and wherein said inactive leukotoxin comprises proleukotoxin.

10. The composition of claim 9, further comprising a diluent.

11. The composition of claim 10, further comprising one or more compounds selected from the group consisting of excipients and adjuvants.

12. The composition of claim 9, wherein said recombinant *Pasteurella haemolytica* comprises an lktC::cat operon fusion.

13. The composition of claim 9, wherein said expression of inactive leukotoxin is stably maintained.

14. The composition of claim 9, wherein said recombinant *Pasteurella haemolytica* contains an activator for expression of said inactive leukotoxin.

15. The composition of claim 14, wherein said activator is AlxA.

16. The composition of claim 9, wherein said recombinant *Pasteurella haemolytica* further comprises a strong leukotoxin promoter.

* * * * *

SEQUENCE LISTING

<160> NUMBER OF SEQ ID NOS: 11

<210> SEQ ID NO 1
<211> LENGTH: 5162
<212> TYPE: DNA
<213> ORGANISM: Artificial Sequence
<220> FEATURE:
<223> OTHER INFORMATION: Description of Artificial Sequence: Synthetic

<400> SEQUENCE: 1

```
aagcttgtca ttaagtaatg tttgaagcat aagaatagag agttagtatt attttttgcg      60
attacatttt actactctct attttttttat ttcaaatgtt caacagaccc tattatagaa     120
gcccccatga ataaatcgct catcattttc ggcatcgtca ataaacctc ggacagtttc       180 tccgatggag gccggtatct ggcgaattcg tacgcgtata cttaagggcc catggtaccc     240
ggggatcctc tagagtcgac ctgcaggcat gcttggtgat aacggcaatt ccgggagtac    300
cggcggctga tctgtctgga gcggatttgc tcaaagcgtg gccgtcaatg gggcagcaac    360 ttgcgctgt tcacagctat cggttgatca atgtcccgtt tgagcgcagg ctgtcgcgaa      420
tgttcggacg cgccgttgat gtggtgtccc gcaatgccgt caatcccgac ttcttaccgg    480
acgaggacaa gagtacgccg ctgcacgatc ttttggctcg tgtcgaacga gagctaccgg   540
tgcggctcga ccaagagcgc accgatatgg ttgtttgcca tggtgatccc tgcatgccga   600
acttcatggt ggaccctaaa actcttcaat gcacgggtct gatcgacctt gggcggctcg    660
gaacagcaga tcgctatgcc gatttggcac tcatgattgc taacgccgaa gagaactggg    720
cagcgccaga tgaagcagag cgcgccttcg ctgtcctatt caatgtattg gggatcgaag   780
cccccgaccg cgaacgcctt gccttctatc tgcgattgga ccctctgact tggggttgat   840
gttcatgccg cctgttttc ctgctcattg gcacgtttcg caacctgttc tcattgcgga    900 cacctttcc agcctcgttt ggaaagtttc attgccagta ataccaatgc tttagaaaga    960
aaaggatcga acttttgaca ttcgatccct ttttctgtaa tctgtttcgt gcgttctttg  1020
ctaagataca gaccctagac aagtcatatc ttagcaaagg gtagctagta atgcaagaga    1080
ttgcgaagcg tccctactac caaaaaacca ttcaacgacg taaacagaca aacgcaaacc    1140
ttaaattaga cggtcttcag ctcggacttc ggaagaataa acaggcgtag aagtgataac   1200
gttcttaata cgaaaattaa gctctgtctc cgtttcgtgc tacggttaga aacggaaagc    1260
cccaagaaat acaagcacac ctgataagcg agatttaagg ataacagcga aattcaatag   1320
ggtctgaatt tccaaactag gttaaatgcc acgacgtttt attgttgccc cattcaagca    1380
acatttgaga accgaataga aatcttttag taaaaagcgt tctttttttgg gtcagcggtt    1440 aatgtggacg gtttaacggt ttttcctgcg ggtcgtattg gaaagccatt gaaaagctga   1500
```

-continued

```
tggataactc tgcgagttac ccacgagctt tccaacagct ttccaacact aaaaacctac    1560
cgcccacaat aaccacttcc ctaataataa aattttttta tttttatttt ggttcaaagc    1620
tcacgatgtt cgcctaataa aacgaagtcc gtatcgcgtc cgctgatttt tatatatcac    1680
tctcggggct tttggtgtac tattgtcttt tgtaatagca aggacacaaa aagggtactc    1740
ttcgagtttc cttttttgacc ttgcaaaagg ctttgccccc ttgaccccg accgctttca    1800 gcggtcaaaa tagaagaacg gacaccatta tgaaacgtga gaaagagata aaaatcaggc    1860
tcaccgaaaa cgagtatcaa gccttgttag agagaaaaac gaaagcaagg cttgcggagt    1920
gggttcggga agttgccctg aacagcaac ctaagcgaca gccgaaagta atcgaccctg    1980
cgttactgtt cgagctgaac cgcataggcg taaacctgaa ccaaatcgcc cgacaatgca    2040
acagtcaaaa gccgagcatt gaccttgtta gcgtgttggc gaccttgcga gaaattgaaa    2100
aaaatctcaa aaaattgcga gaattgagcc tatgatcgtt aaattttttta agaaacacgg    2160 taagggaaaa gctagtagtt gcaaggcttg cgtggactat ttactaaata agcctgacga    2220
caccgcccaa atcctgcagg gcgatcccg actatcacaa agtattgctg atagtcttga    2280
ttttaataac acttacaccg caggttgctt gtcttttgaa gaaagcgacc tacccgaaat    2340
acaaaagcgt gagattatgg cacgcttga aaaggcaatg tttgcagggc ttgagcctga    2400
acaatataac attgcgtggg tacaacacac cgacaaaggc aggcttgagc tgaatttcgt    2460
tatcccaaac gtagagatga caagcggaaa acgcctacaa ccctactacg acagggcaga    2520
ccgccacttg ctgaaaactt caagcaggta atcaaccacg aatacagcct aagcgaccca    2580 aacaaccta taaagcaaaa aacctgattg accgcaaaga cctaccaacc gataaaacag    2640
gctttacagg cgattacgga cggtttaaca gctttagcga acgcagggca gataaacgac    2700
cgacaggacg ttataaatgc cctagaacgt gcaggttttg aaattgcacg cattacgcca    2760
aaaaacctat caatcaagac tgacggacag aatttaagat taaaggggc tttctatgag    2820 caagatttta gatttagcac agaccttca gcagacatca cagaaagagc tagagagtac    2880
aagcgagata gtgcagaacg ctatcaaacg gcacgagcaa aacttgatac agcagttaca    2940
gcacgcaggg aacaatttag ccgaaaatat ccaaatcgag caggcgaaat tgataaaaaa    3000
taccgtgaga atgtatcgct tgccgaccct aatcgccttg acgatattaa ccttgatagc    3060
cataaccact ccatatccgg atcattcaac agtacaacga aatcagcgag caattaacga    3120
cattacagag tttaataaac agcttgaaac ggtaatatct caacgcaaaa gacaaagcag    3180
gggtatgagc agataaaaca aggggggagaa ttatggcaac acttatggaa aaagacagtt    3240
taataaatgg tatttctcaa acactcggct tattgtaaga tgtcggtagg aagtactcat    3300
catttggaag tggtttttgt gtggaaacaa aattatattc tagttgatga gtacttcttt    3360
ttttgttgca cttggattgt aaattcagcc ctaaattttc actttttcta acaaaatgaa    3420
tttgttagtt gagctgtaaa gtatgaaata cttgctttgc tgcatcttct actaatttat    3480
tgttgaattt ggcttcttcg gtaaattgcg tactcatgat tgccatcaca atcggtttgc    3540
gatttggtat gcgaaccacc gcaatatcat tgcgtacacc atatttaccc gccccgcttt    3600
tatcgtacac tttccacgat gttggcgtag cagcgcgaat caatggattg cctgttgcgt    3660
tattgtccaa ccaattccac aaaatcgttt tttgcgattc ggttaatgtg ttgcccaata    3720
aatacgcatt taaattcatc gccatttgtt tgggtgtact cgtatcacga atatcgttgg    3780
gtttggcttg atttaaatcg ggttctagcc gattggtatg ggttacgtta tcgcctaatt    3840
```

| | |
|---|---:|
| gtcgcaaaat acgttgatat tgttccacgc cacccaattc tttgagcagc aaattggtcg | 3900 |
| cgctgttgtc gctaaaccgc acggctgctt cacataattg ggcaatcgtc atgcctttgc | 3960 |
| caacgtatttt ttgggtttcg ggagaataac taaccaaatc ttttttggcta tatgaaatgg | 4020 |
| tacgatttaa atcttttca ggcagcgatt gcaacaccgc cccagccaac aacgccttga | 4080 |
| aagtggacgc ataagcaaag cgttcatctg cacgataaga caaagaatgt cccgtttctg | 4140 |
| tatcccatac ataaacgcca attcgggctt gatactgctg ttccaaattc gccaaagtct | 4200 |
| gttgaaaggt ggcttgtgtg gctgattgtt gcacaggcgc actagcaggc tgcggattag | 4260 |
| acgttaccga atgaacagaa ttgggcgaac aagccgttaa tgtcagcaat aataatgtgc | 4320 |
| cgattttttaa cttatttaac ataaattatc ctttgatttt actaaataaa tttcttttca | 4380 |
| ggcagcctga aacgtacatt gcgcggaaat tcggataatt tgtttgtaga caaaaaaac | 4440 |
| agattttggc gaatttaagc gcaaaagtct agcaatttag cctttaatct caatgctttc | 4500 |
| tacaatgaaa tgcactttga tattctcaag taagttcgcc tctaggtatg caatttgctt | 4560 |
| gtctaagtct tgaagcggat aaataaccct tgccccaatt cgtagaggtt tcacataaat | 4620 |
| caccccctta gcactataag gctaagcgac taggctcaca ctatgaacgg tagtgcgagc | 4680 |
| cgccgccata gtgcgaaagt gattttaaca cataaccgcc taacaaggcg gtttttgttt | 4740 |
| attcgggact gaaaaagccg ttgaaacttg ctttcaatgg ctttttttagt ctaacaaccg | 4800 |
| cagggcgtta gcagaaaggt gcacgaattt tcataaaatt acacggtaag aaaggtgtat | 4860 |
| ggatttttcac aaaggtgtac agatttttaat aaaatacacc ttaaagcctt taataccaat | 4920 |
| gctttagaaa agaaaagg atctttaata agttgtttaa aattttggt gaatttatcc | 4980 |
| aattttgtcc atcttctaaa agttttaaaa acagtattat actttccaaa gcattctggt | 5040 |
| aaatatcgcc atgggcagcc tgttttcagg cgatataaga ttcctgtgaa aatatttctt | 5100 |
| aaatttggtt tgtcatagat attcaaatct aggataatag gctttagttt caaccaaagc | 5160 |
| tt | 5162 |

<210> SEQ ID NO 2
<211> LENGTH: 6850
<212> TYPE: DNA
<213> ORGANISM: Artificial Sequence
<220> FEATURE:
<223> OTHER INFORMATION: Description of Artificial Sequence: Synthetic

<400> SEQUENCE: 2

| | |
|---|---:|
| aagcttgtca ttaagtaatg tttgaagcat aagaatagag agttagtatt attttttgcg | 60 |
| attacattt actactctct attttttat ttcaaatgtt caacagaccc tattatagaa | 120 |
| gccccccatga ataaatcgct catcattttc ggcatcgtcg ggctgcagat ccttagcaaa | 180 |
| gctaaggatt ttttttaagc ttggcactgg ccgtcgtttt acaacgtcgt gactgggaaa | 240 |
| accctggcgt tacccaactt aatcgccttg cagcacatcc ccctttcgcc agatcaagct | 300 |
| tatcgatacc gtcatcttgt gcctgcgcag taaccacaca cccgaataaa agggtcaaaa | 360 |
| gtgttttttt cataaaaagt ccctgtgttt tcattataag gattaccact ttaacgcagt | 420 |
| tactttctta aaaaagtct tcttttcata agtttgttt tatgtcatac aaacacatca | 480 |
| aattgagatg tagtttctca atcctcttga ttcctctatc tcaaaaaaac aacccaaaag | 540 |
| aaaaaagaaa agtatatgtt acattaatat tacaatgtaa ttattttgtt taatttccct | 600 |
| acattttgta taacttaaa acactccttt ttctcttctg attatataaa agacaaaaaa | 660 |
| tacaatttaa gctacaaaaa acaacaaaaa acaacaaaaa acacgacaat aagatcgagt | 720 |

-continued

```
aatgattata ttatgttata atttttgacc taatttagaa taattatcga gtgcaaatta      780
tgaatcaatc ttattttaac ttactaggaa acattacttg gctatggatg aactcctccc      840
tccacaaaga atggagctgt gaactactag cacgcaatgt gattcctgca attgaaaatg      900
aacaatatat gctacttata gataacggta ttccgatcgc ttattgtagt tgggcagatt      960
taaaccttga gactgaggtg aaatatatta aggatattaa ttcgttaaca ccagaagaat     1020
ggcagtctgg tgacagacgc tggattattg attgggtagc accattcgga cattctcaat     1080
tactttataa aaaatgtgt cagaaatacc ctgtatgat cgtcagatct atacgctttt      1140
atccaaagca gaaagaatta ggcaaaattg cctactttaa aggaggtaaa ttagataaaa     1200
aaacagcaaa aaaacgtttt gatacatatc aagaagagct ggcaacacga cttaaaaatg     1260
aatttaattt tattaaaaaa tagaaggaga catcccttat gggaactaga cttacaaccc     1320
tatcaaatgg gctaaaaaac actttaacgg caaccaaaag tggcttacat aaagccggtc     1380
aatcattaac ccaagccggc agttctttaa aaactggggc aaaaaaaatt atcctctata     1440
ttccccaaaa ttaccaatat gatactgaac aaggtaatgg tttacaggat ttagtcaaag     1500
cggccgaaga gttggggatt gaggtacaaa agaagaacg caataatatt gcaacagctc      1560
aaaccagttt aggcacgatt caaaccgcta ttggcttaac tgagcgtggc attgtgttat     1620
ccgctccaca aattgataaa ttgctacaga aaactaaagc aggccaagca ttaggttctg     1680
ccgaaagcat tgtacaaaat gcaaataaag ccaaaactgt attatctggc attcaatcta     1740
ttttaggctc agtattggct ggaatggatt tagatgaggc cttacagaat aacagcaacc     1800
aacatgctct tgctaaagct ggcttggagc taacaaattc attaattgaa atattgctaa     1860
attcagtaaa aacacttgac gaatttggtg agcaaattag tcaatttggt tcaaaactac     1920
aaaatatcaa aggcttaggg actttaggag acaaactcaa aaatatcggt ggacttgata     1980
aagctggcct tggtttagat gttatctcag gctattatc gggcgcaaca gctgcacttg      2040
tacttgcaga taaaaatgct tcaacagcta aaaaagtggg tgcgggtttt gaattggcaa     2100
accaagttgt tggtaatatt accaaagccg tttcttctta catttttagcc caacgtgttg     2160 cagcaggttt atcttcaact gggcctgtgg ctgctttaat tgcttctact gtttctcttg     2220
cgattagccc attagcattt gccggtattg ccgataaatt taatcatgca aaaagtttag     2280
agagttatgc cgaacgcttt aaaaaattag gctatgacgg agataattta ttagcagaat     2340
atcagcgggg aacagggact attgatgcaa tttggcactc atgattgcta acgccgaaga     2400
gaactgggca gcgccagatg aagcagagcg cgccttcgct gtcctattca atgtattggg     2460
gatcgaagcc cccgaccgcg aacgccttgc cttctatctg cgattggacc ctctgacttg     2520
gggttgatgt tcatgccgcc tgtttttcct gctcattggc acgtttcgca acctgttctc     2580
attgcggaca ccttttccag cctcgtttgg aaagtttcat tgccagtaat accaatgctt     2640
tagaaagaaa aggatcgaac ttttgacatt cgatcccttt ttctgtaatc tgtttcgtgc     2700
gttctttgct aagatacaga ccctagacaa gtcatatctt agcaagggt agctagtaat      2760 gcaagagatt gcgaagcgtc cctactacca aaaaccatt caacgacgta acagacaaa       2820 cgcaaacctt aaattagacg gtcttcagct cggacttcgg aagaataaac aggcgtagaa     2880
gtgataacgt tcttaatacg aaaattaagc tctgtctccg tttcgtgcta cggttagaaa     2940
cggaaagccc caagaaatac aagcacacct gataagcgag atttaaggat aacagcgaaa     3000
ttcaataggg tctgaatttc caaactaggt taaatgccac gacgttttat tgttgcccca     3060
```

-continued

```
ttcaagcaac atttgagaac cgaatagaaa tcttttagta aaaagcgttc ttttttgggt    3120
cagcggttaa tgtggacggt ttaacggttt ttcctgcggg tcgtattgga aagccattga    3180
aaagctgatg gataactctg cgagttaccc acgagctttc aacagctttc caacactaa     3240
aaacctaccg cccacaataa ccacttccct aataataaaa tttttttatt tttattttgg    3300
ttcaaagctc acgatgttcg cctaataaaa cgaagtccgt atcgcgtccg ctgatttta     3360
tatatcactc tcggggcttt tggtgtacta ttgtcttttg taatagcaag gacacaaaaa    3420
gggtactctt cgagtttcct ttttgacctt gcaaaaggct ttgcccccett gacccccgac   3480
cgctttcagc ggtcaaaata gaagaacgga caccattatg aaacgtgaga agagataaa     3540
aatcaggctc accgaaaacg agtatcaagc cttgttagag agaaaaacga agcaaggct     3600
tgcggagtgg gttcgggaag ttgccctgga acagcaacct aagcgacagc cgaaagtaat    3660
cgaccctgcg ttactgttcg agctgaaccg cataggcgta aacctgaacc aaatcgcccg    3720
acaatgcaac agtcaaaagc cgagcattga ccttgttagc gtgttggcga ccttgcgaga    3780
aattgaaaaa aatctcaaaa aattgcgaga attgagccta tgatcgttaa attttttaag    3840
aaacacggta agggaaaagc tagtagttgc aaggcttgcg tggactattt actaaataag    3900
cctgacgaca ccgcccaaat cctgcagggc gatccccgac tatcacaaag tattgctgat    3960
agtcttgatt ttaataacac ttacaccgca ggttgcttgt cttttgaaga aagcgaccta    4020
cccgaaatac aaaagcgtga gattatggca cgctttgaaa aggcaatgtt tgcagggctt    4080
gagcctgaac aatataacat tgcgtgggta caacacaccg acaaaggcag gcttgagctg    4140
aatttcgtta tcccaaacgt agagatgaca agcggaaaac gcctacaacc ctactacgac    4200
agggcagacc gccacttgct gaaaacttca agcaggtaat caaccacgaa tacagcctaa    4260
gcgacccaaa caaccctata aagcaaaaaa cctgattgac cgcaaagacc taccaaccga    4320
taaaacaggc tttacaggcg attacggacg gtttaacagc tttagcgaac gcagggcaga    4380
taaacgaccg acaggacgtt ataaatgccc tagaacgtgc aggttttgaa attgcacgca    4440
ttacgccaaa aaacctatca atcaagactg acggacagaa tttaagatta aaagggggctt   4500
tctatgagca agattttaga tttagcacag acctttcagc agacatcaca gaaagagcta    4560
gagagtacaa gcgagatagt gcagaacgct atcaaacggc acgagcaaaa cttgatacag    4620
cagttacagc acgcagggaa caatttagcc gaaaatatcc aaatcgagca ggcgaaattg    4680
ataaaaaata ccgtgagaat gtatcgcttg ccgaccctaa tcgccttgac gatattaacc    4740
ttgatagcca taaccactcc atatccggat cattcaacag tacaacgaaa tcagcgagca    4800
attaacgaca ttacagagtt taataaacag cttgaaacgg taatatctca acgcaaaaga    4860
caaagcaggg gtatgagcag ataaaacaag ggggagaatt atggcaacac ttatggaaaa    4920
agacagttta ataaatggta tttctcaaac actcggctta ttgtaagatg tcggtaggaa    4980
gtactcatca tttggaagtg ttttttgtgt ggaaacaaaa ttatattcta gttgatgagt    5040
acttctttt ttgttgcact tggattgtaa attcagccct aaattttcac ttttctaac      5100
aaaatgaatt tgttagttga gctgtaaagt atgaaatact tgctttgctg catcttctac    5160
taatttattg ttgaatttgg cttcttcggt aaattgcgta ctcatgattg ccatcacaat    5220
cggtttgcga tttggtatgc gaaccaccgc aatatcattg cgtacaccat atttacccgc    5280
cccgctttta tcgtacactt tccacgatgt tggcgtagca gcgcgaatca atggattgcc    5340
tgttgcgtta ttgtccaacc aattccacaa aatcgttttt tgcgattcgg ttaatgtgtt    5400
gcccaataaa tacgcatttta aattcatcgc catttgtttg ggtgtactcg tatcacgaat    5460
```

-continued

```
atcgttgggt tggcttgat ttaaatcggg ttctagccga ttggtatggg ttacgttatc    5520
gcctaattgt cgcaaaatac gttgatattg ttccacgcca cccaattctt tgagcagcaa    5580
attggtcgcg ctgttgtcgc taaaccgcac ggctgcttca cataattggg caatcgtcat    5640
gcctttgcca acgtattttt gggtttcggg agaataacta accaaatctt tttggctata    5700
tgaaatggta cgatttaaat cttttttcagg cagcgattgc aacaccgccc cagccaacaa    5760
cgccttgaaa gtggacgcat aagcaaagcg ttcatctgca cgataagaca aagaatgtcc    5820
cgtttctgta tcccatacat aaacgccaat tcgggcttga tactgctgtt ccaaattcgc    5880
caaagtctgt tgaaaggtgg cttgtgtggc tgattgttgc acaggcgcac tagcaggctg    5940
cggattagac gttaccgaat gaacagaatt gggcgaacaa gccgttaatg tcagcaataa    6000
taatgtgccg attttttaact tatttaacat aaattatcct ttgattttac taaataaatt    6060
tcttttcagg cagcctgaaa cgtacattgc gcggaaattc ggataatttg tttgtagaac    6120
aaaaaaacag attttggcga atttaagcgc aaaagtctag caatttagcc tttaatctca    6180
atgctttcta caatgaaatg cactttgata ttctcaagta agttcgcctc taggtatgca    6240
atttgcttgt ctaagtcttg aagcggataa ataacccttg ccccaattcg tagaggtttc    6300
acataaatca ccccettage actataagge taagegacta ggetcacact atgaacggta    6360 gtgcgagccg ccgccatagt gcgaaagtga ttttaacaca taaccgccta acaaggcggt    6420 tttgtttttat tcgggactga aaaagccgtt gaaacttgct ttcaatggct tttttagtct    6480
aacaaccgca gggcgttagc agaaaggtgc acgaattttc ataaaattac acggtaagaa    6540
aggtgtatgg attttcacaa aggtgtacag attttaataa aatacacctt aaagcccttta   6600 ataccaatgc tttagaaaag aaaaagggat ctttaataag ttgtttaaaa attttggtga    6660
atttatccaa ttttgtccat cttctaaaag ttttaaaaac agtattatac tttccaaagc    6720
attctggtaa atatcgccat gggcagcctg ttttcaggcg atataagatt cctgtgaaaa    6780
tatttcttaa atttggtttg tcatagatat tcaaatctag gataataggc tttagtttca    6840
accaaagctt                                                            6850
```

<210> SEQ ID NO 3
<211> LENGTH: 4066
<212> TYPE: DNA
<213> ORGANISM: Artificial Sequence
<220> FEATURE:
<223> OTHER INFORMATION: Description of Artificial Sequence:  Synthetic

<400> SEQUENCE: 3

```
aacataaccct cggacagttt ctccgatgga ggccggtatc tggcgaattc gtacgcgtat     60
acttaagggc ccatggtacc cgggctgcag gaattcgata tcaagcttat cgataccgtc    120
cgaatgttcg gacgcgccgt tgatgtggtg tcccgcaatg ccgtcaatcc cgacttctta    180
ccggacgagg acaagagtac gccgctgcac gatcttttgg ctcgtgtcga acgagagcta    240
ccggtgcggc tcgaccaaga gcgcaccgat atggttgttt gccatggtga tccctgcatg    300
ccgaacttca tggtggaccc taaaactctt caatgcacgg gtctgatcga ccttgggcgg    360
ctcggaacag cagatcgcta tgccgatttg cactcatga ttgctaacgc gaagagaac    420 tgggcagcgc cagatgaagc agagcgcgcc ttcgctgtcc tattcaatgt attggggatc    480
gaagcccccg accgcgaacg ccttgccttc tatctgcgat tggaccctct gacttggggt    540
tgatgttcat gccgcctgtt tttcctgctc attggcacgt ttcgcaacct gttctcattg    600
```

-continued

| | |
|---|---|
| cggacacctt ttccagcctc gtttggaaag tttcattgcc agtaatacca atgctttaga | 660 |
| aagaaaagga tcgaactttt gacattcgat ccctttttct gtaatctgtt tcgtgcgttc | 720 |
| tttgctaaga tacagaccct agacaagtca tatcttagca aagggtagct agtaatgcaa | 780 |
| gagattgcga agcgtccctc ctaccaaaaa accattcaac gacgtaaaca gacaaacgca | 840 |
| aaccttaaat tagacggtct tcagctcgga cttcggaaga ataaacaggc gtagaagtga | 900 |
| taacgttctt aatacgaaaa ttaagctctg tctccgtttc gtgctacggt tagaaacgga | 960 |
| aagccccaag aaatacaagc acacctgata agcgagattt aaggataaca gcgaaattca | 1020 |
| atagggtctg aatttccaaa ctaggttaaa tgccacgacg ttttattgtt gccccattca | 1080 |
| agcaacattt gagaaccgaa tagaaatctt ttagtaaaaa gcgttctttt ttgggtcagc | 1140 |
| ggttaatgtg gacggtttaa cggttttttcc tgcgggtcgt attggaaagc cattgaaaag | 1200 |
| ctgatggata actctgcgag ttacccacga gctttccaac agctttccaa cactaaaaac | 1260 |
| ctaccgccca caataaccac ttccctaata ataaaatttt tttattttta ttttggttca | 1320 |
| aagctcacga tgttcgccta ataaaacgaa gtccgtatcg cgtccgctga ttttatata | 1380 |
| tcactctcgg ggcttttggt gtactattgt cttttgtaat agcaaggaca caaaaagggt | 1440 |
| actcttcgag tttccttttt gaccttgcaa aaggctttgc cccttgacc cccgaccgct | 1500 |
| ttcagcggtc aaaatagaag aacggacacc attatgaaac gtgagaaaga gataaaaatc | 1560 |
| aggctcaccg aaaacgagta tcaagccttg ttagagagaa aaacgaaagc aaggcttgcg | 1620 |
| gagtgggttc gggaagttgc cctggaacag caacctaagc gacagccgaa agtaatcgac | 1680 |
| cctgcgttac tgttcgagct gaaccgcata ggcgtaaacc tgaaccaaat cgcccgacaa | 1740 |
| tgcaacagtc aaaagccgag cattgacctt gttagcgtgt tggcgaccatt gcgagaaatt | 1800 |
| gaaaaaaatc tcaaaaaatt gcgagaattg agcctatgat cgttaaattt tttaagaaac | 1860 |
| acggtaaggg aaaagctagt agttgcaagg cttgcgtgga ctatttacta aataagcctg | 1920 |
| acgacaccgc ccaaatcctg cagggcgatc cccgactatc acaaagtatt gctgatagtc | 1980 |
| ttgattttaa taacacttac accgcaggtt gcttgtcttt tgaagaaagc gacctacccg | 2040 |
| aaatacaaaa gcgtgagatt atggcacgct ttgaaaaggc aatgtttgca gggcttgagc | 2100 |
| ctgaacaata taacattgcg tgggtacaac acaccgacaa aggcaggctt gagctgaatt | 2160 |
| tcgttatccc aaacgtagag atgacaagcg gaaaacgcct acaaccctac tacgacaggg | 2220 |
| cagaccgcca cttgctgaaa acttcaagca ggtaatcaac cacgaataca gcctaagcga | 2280 |
| cccaaacaac cctataaagc aaaaaacctg attgaccgca aagacctacc aaccgataaa | 2340 |
| acaggcttta caggcgatta cggacggttt aacagcttta gcgaacgcag ggcagataaa | 2400 |
| cgaccgacag gacgttataa atgccctaga acgtgcaggt tttgaaattg cacgcattac | 2460 |
| gccaaaaaac ctatcaatca agactgacgg acagaattta agattaaaag gggctttcta | 2520 |
| tgagcaagat tttagattta gcacagacct ttcagcagac atcacagaaa gagctagaga | 2580 |
| gtacaagcga gatagtgcag aacgctatca acggcacga gcaaaacttg atacagcagt | 2640 |
| tacagcacgc agggaacaat ttagccgaaa atatccaaat cgagcaggcg aaattgataa | 2700 |
| aaaataccgt gagaatgtat cgcttgccga ccctaatcgc cttgacgata ttaaccttga | 2760 |
| tagccataac cactccatat ccggatccgt cgacctgcag gggggggggg gcgctgaggt | 2820 |
| ctgcctcgtg aagaaggtgt tgctgactca taccaggcct gaatcgcccc atcatccagc | 2880 |
| cagaaagtga gggagccacg gttgatgaga gctttgttgt aggtggacca gttggtgatt | 2940 |
| ttgaactttt gctttgccac ggaacggtct gcgttgtcgg gaagatgcgt gatctgatcc | 3000 |

-continued

```
ttcaactcag caaaagttcg atttattcaa caaagccgcc gtcccgtcaa gtcagcgtaa      3060
tgctctgcca gtgttacaac caattaacca attctgatta gaaaaactca tcgagcatca      3120
aatgaaactg caatttattc atatcaggat tatcaatacc atatttttga aaaagccgtt      3180
tctgtaatga aggagaaaac tcaccgaggc agttccatag gatggcaaga tcctggtatc      3240
ggtctgcgat tccgactcgt ccaacatcaa tacaacctat taatttcccc tcgtcaaaaa      3300
taaggttatc aagtgagaaa tcaccatgag tgacgactga atccggtgag aatggcaaaa      3360
gcttatgcat ttctttccag acttgttcaa caggccagcc attacgctcg tcatcaaaat      3420
cactcgcatc aaccaaaccg ttattcattc gtgattgcgc ctgagcgaga cgaaatacgc      3480
gatcgctgtt aaaaggacaa ttacaaacag gaatcgaatg caaccggcgc aggaacactg      3540
ccagcgcatc aacaatattt tcacctgaat caggatattc ttctaatacc tggaatgctg      3600
ttttcccggg gatcgcagtg gtgagtaacc atgcatcatc aggagtacgg ataaaatgct      3660
tgatggtcgg aagaggcata aattccgtca gccagtttag tctgaccatc tcatctgtaa      3720
catcattggc aacgctacct ttgccatgtt tcagaaacaa ctctggcgca tcgggcttcc      3780
catacaatcg atagattgtc gcacctgatt gcccgacatt atcgcgagcc catttatacc      3840
catataaatc agcatccatg ttggaattta atcgcggcct cgagcaagac gtttcccgtt      3900
gaatatggct cataacaccc cttgtattac tgtttatgta agcagacagt tttattgttc      3960
atgatgatat ttttatct tgtgcaatgt aacatcagag attttgagac acaacgtggc      4020
tttccccccc ccccctgcag gtcgacggat ctttaataag ttgttt                    4066
```

<210> SEQ ID NO 4
<211> LENGTH: 5162
<212> TYPE: DNA
<213> ORGANISM: Artificial Sequence
<220> FEATURE:
<223> OTHER INFORMATION: Description of Artificial Sequence: Synthetic

<400> SEQUENCE: 4

```
aagcttgtca ttaagtaatg tttgaagcat aagaatagag agttagtatt attttttgcg       60
attacatttt actactctct attttttat ttcaaatgtt caacagaccc tattatagaa      120 gccccccatga ataaatcgct catcattttc ggcatcgtca acataacctc ggacagtttc      180
tccgatggag gccggtatct ggcgaattcg tacgcgtata cttaagggcc catggtaccc      240
ggggatcctc tagagtcgac ctgcaggcat gcttggtgat aacggcaatt ccgggagtac      300
cggcggctga tctgtctgga gcggatttgc tcaaagcgtg gccgtcaatg ggcagcaac      360 ttggcgctgt tcacagctat cggttgatca atgtcccgtt tgagcgcagg ctgtcgcgaa      420
tgttcggacg cgccgttgat gtggtgtccc gcaatgccgt caatcccgac ttcttaccgg      480
acgaggacaa gagtacgccg ctgcacgatc ttttggctcg tgtcgaacga gagctaccgg      540
tgcggctcga ccaagagcgc accgatatgg ttgtttgcca tggtgatccc tgcatgccga      600
acttcatggt ggaccctaaa actcttcaat gcacgggtct gatcgacctt gggcggctcg      660
gaacagcaga tcgctatgcc gatttggcac tcatgattgc taacgccgaa gagaactggg      720
cagcgccaga tgaagcagag cgcgccttcg ctgtcctatt caatgtattg gggatcgaag      780 ccccccgaccg cgaacgcctt gccttctatc tgcgattgga ccctctgact tggggttgat      840
gttcatgccg cctgttttt ctgctcattg gcacgtttcg caacctgttc tcattgcgga      900 cacctttttcc agcctcgttt ggaaagtttc attgccagta ataccaatgc tttagaaaga      960
```

-continued

```
aaaggatcga acttttgaca ttcgatccct ttttctgtaa tctgtttcgt gcgttctttg    1020
ctaagataca gaccctagac aagtcatatc ttagcaaagg gtagctagta atgcaagaga    1080
ttgcgaagcg tccctactac caaaaaacca ttcaacgacg taaacagaca aacgcaaacc    1140
ttaaattaga cggtcttcag ctcggacttc ggaagaataa acaggcgtag aagtgataac    1200
gttcttaata cgaaaattaa gctctgtctc cgtttcgtgc tacggttaga aacggaaagc    1260
cccaagaaat acaagcacac ctgataagcg agatttaagg ataacagcga aattcaatag    1320
ggtctgaatt tccaaactag gttaaatgcc acgacgtttt attgtgccc cattcaagca     1380 acatttgaga accgaataga aatctttag taaaaagcgt tcttttttgg gtcagcggtt     1440
aatgtggacg gtttaacggt ttttcctgcg ggtcgtattg gaaagccatt gaaaagctga    1500
tggataactc tgcgagttac ccacgagctt tccaacagct ttccaacact aaaaacctac    1560
cgcccacaat aaccacttcc ctaataataa aattttttta tttttatttt ggttcaaagc    1620
tcacgatgtt cgcctaataa aacgaagtcc gtatcgcgtc cgctgatttt tatatatcac    1680
tctcggggct tttggtgtac tattgtcttt tgtaatagca aggacacaaa aagggtactc    1740
ttcgagtttc cttttttgacc ttgcaaaagg ctttgccccc ttgaccccg accgctttca    1800 gcggtcaaaa tagaagaacg gacaccatta tgaaacgtga gaaagagata aaaatcaggc    1860
tcaccgaaaa cgagtatcaa gccttgttag agagaaaaac gaaagcaagg cttgcggagt    1920
gggttcggga agttgccctg gaacagcaac ctaagcgaca gccgaaagta atcgaccctg    1980
cgttactgtt cgagctgaac cgcataggcg taaacctgaa ccaaatcgcc cgacaatgca    2040
acagtcaaaa gccgagcatt gaccttgtta gcgtgttggc gaccttgcga gaaattgaaa    2100
aaaatctcaa aaaattgcga gaattgagcc tatgatcgtt aaatttttta agaaacacgg    2160
taagggaaaa gctagtagtt gcaaggcttg cgtggactat ttactaaata agcctgacga    2220
caccgcccaa atcctgcagg gcgatccccg actatcacaa agtattgctg atagtcttga    2280
ttttaataac acttacaccg caggttgctt gtcttttgaa gaaagcgacc tacccgaaat    2340
acaaaagcgt gagattatgg cacgctttga aaaggcaatg tttgcagggc ttgagcctga    2400
acaatataac attgcgtggg tacaacacac cgacaaaggc aggcttgagc tgaatttcgt    2460
tatcccaaac gtagagatga caagcggaaa acgcctacaa ccctactacg acagggcaga    2520
ccgccacttg ctgaaaactt caagcaggta atcaaccacg aatacagcct aagcgaccca    2580
aacaacccta taaagcaaaa aacctgattg accgcaaaga cctaccaacc gataaaacag    2640
gctttacagg cgattacgga cggtttaaca gctttagcga acgcagggca gataaacgac    2700
cgacaggacg ttataaatgc cctagaacgt gcaggttttg aaattgcacg cattacgcca    2760
aaaaacctat caatcaagac tgacggacag aatttaagat taaaaggggc tttctatgag    2820 caagattta gatttagcac agacctttca gcagacatca cagaaagagc tagagagtac    2880
aagcgagata gtgcagaacg ctatcaaacg gcacgagcaa aacttgatac agcagttaca    2940
gcacgcaggg aacaatttag ccgaaaatat ccaaatcgag caggcgaaat tgataaaaaa    3000
taccgtgaga atgtatcgct tgccgaccct aatcgccttg acgatattaa ccttgatagc    3060
cataaccact ccatatccgg atcattcaac agtacaacga atcagcgag caattaacga    3120 cattacagag tttaataaac agcttgaaac ggtaatatct caacgcaaaa gacaaagcag    3180
gggtatgagc agataaaaca aggggagaa ttatggcaac acttatgaa aaagacagtt     3240 taataaatgg tatttctcaa acactcggct tattgtaaga tgtcggtagg aagtactcat    3300
catttggaag tggttttttgt gtggaaacaa aattatattc tagttgatga gtacttcttt    3360
```

```
ttttgttgca cttggattgt aaattcagcc ctaaattttc acttttttcta acaaaatgaa    3420 tttgttagtt gagctgtaaa gtatgaaata cttgctttgc tgcatcttct actaatttat    3480
tgttgaattt ggcttcttcg gtaaattgcg tactcatgat tgccatcaca atcggtttgc    3540
gatttggtat gcgaaccacc gcaatatcat tgcgtacacc atatttaccc gccccgcttt    3600
tatcgtacac tttccacgat gttggcgtag cagcgcgaat caatggattg cctgttgcgt    3660
tattgtccaa ccaattccac aaaatcgttt tttgcgattc ggttaatgtg ttgcccaata    3720
aatacgcatt taaattcatc gccatttgtt tgggtgtact cgtatcacga atatcgttgg    3780
gtttggcttg atttaaatcg ggttctagcc gattggtatg ggttacgtta tcgcctaatt    3840
gtcgcaaaat acgttgatat tgttccacgc cacccaattc tttgagcagc aaattggtcg    3900
cgctgttgtc gctaaaccgc acggctgctt cacataattg gcaatcgtc atgcctttgc     3960 caacgtattt ttgggtttcg ggagaataac taaccaaatc ttttttggcta tatgaaatgg    4020 tacgatttaa atcttttttca ggcagcgatt gcaacaccgc cccagccaac aacgccttga   4080
aagtggacgc ataagcaaag cgttcatctg cacgataaga caaagaatgt cccgtttctg    4140
tatcccatac ataaacgcca attcgggctt gatactgctg ttccaaattc gccaaagtct    4200
gttgaaaggt ggcttgtgtg gctgattgtt gcacaggcgc actagcaggc tgcggattag    4260
acgttaccga atgaacagaa ttgggcgaac aagccgttaa tgtcagcaat aataatgtgc    4320 cgattttttaa cttatttaac ataaattatc ctttgatttt actaaataaa tttcttttca    4380
ggcagcctga aacgtacatt gcgcggaaat tcggataatt tgtttgtaga acaaaaaaac    4440
agattttggc gaatttaagc gcaaaagtct agcaatttag cctttaatct caatgctttc    4500
tacaatgaaa tgcactttga tattctcaag taagttcgcc tctaggtatg caatttgctt    4560
gtctaagtct tgaagcggat aaataaccct tgccccaatt cgtagaggtt tcacataaat    4620
caccccctta gcactataag gctaagcgac taggctcaca ctatgaacgg tagtgcgagc    4680
cgccgccata gtgcgaaagt gattttaaca cataaccgcc taacaaggcg ttttgtttt    4740 attcgggact gaaaaagccg ttgaaacttg ctttcaatgg ctttttttagt ctaacaaccg    4800 cagggcgtta gcagaaaggt gcacgaattt tcataaaatt acacggtaag aaaggtgtat    4860
ggattttcac aaaggtgtac agattttaat aaaatacacc ttaaagcctt taataccaat    4920
gctttagaaa agaaaaaggg atctttaata agttgtttaa aaattttggt gaatttatcc    4980
aattttgtcc atcttctaaa agttttaaaa acagtattat actttccaaa gcattctggt    5040
aaatatcgcc atgggcagcc tgttttcagg cgatataaga ttcctgtgaa aatatttctt    5100
aaatttggtt tgtcatagat attcaaatct aggataaatag gctttagttt caaccaaagc    5160
tt                                                                   5162
```

<210> SEQ ID NO 5
<211> LENGTH: 5262
<212> TYPE: DNA
<213> ORGANISM: Artificial Sequence
<220> FEATURE:
<223> OTHER INFORMATION: Description of Artificial Sequence: Synthetic

<400> SEQUENCE: 5

```
aacataaccct cggacagttt ctccgatgga ggccggtatc tggcgaattc gtacgcgtat      60
acttaagggc ccatggtacc cggggatcct ctagaactag tggatccccc gggtgactaa     120
ctagaggaag ctaaaatgga gaaaaaaatc actggatata ccaccgttga tatatcccaa     180
```

-continued

| | |
|---|---|
| tcgcatcgta aagaacattt tgaggcattt cagtcagttg ctcaatgtac ctataaccag | 240 |
| accgttcagc tggatattac ggcctttta aagaccgtaa agaaaaataa gcacaagttt | 300 |
| tatccggcct ttattcacat tcttgcccgc ctgatgaatg ctcatccgga attccgtatg | 360 |
| gcaatgaaag acggtgagct ggtgatatgg gatagtgttc acccttgtta caccgttttc | 420 |
| catgagcaaa ctgaaacgtt ttcatcgctc tggagtgaat accacgacga tttccggcag | 480 |
| tttctacaca tatattcgca agatgtggcg tgttacggtg aaaacctggc ctatttccct | 540 |
| aaagggttta ttgagaatat gtttttcgtc tcagccaatc cctgggtgag tttcaccagt | 600 |
| tttgatttaa acgtggccaa tatggacaac ttcttcgccc ccgttttcac catgggcaaa | 660 |
| tattatacgc aaggcgacaa ggtgctgatg ccgctggcga ttcaggttca tcatgccgtc | 720 |
| tgtgatggct tccatgtcgg cagaatgctt aatgaattac aacagtactg cgatgagtgg | 780 |
| cagggcgggg cgtaatttct ggaaggataa tgacccgggc tgcaggaatt cgatatcaag | 840 |
| cttatcgata ccgtccgaat gttcggacgc gccgttgatg tggtgtcccg caatgccgtc | 900 |
| aatcccgact tcttaccgga cgaggacaag agtacgccgc tgcacgatct tttggctcgt | 960 |
| gtcgaacgag agctaccggt gcggctcgac caagagcgca ccgatatggt tgtttgccat | 1020 |
| ggtgatccct gcatgccgaa cttcatggtg gaccctaaaa ctcttcaatg cacgggtctg | 1080 |
| atcgaccttg gcggctcgg aacagcagat cgctatgccg atttggcact catgattgct | 1140 |
| aacgccgaag agaactgggc agcgccagat gaagcagagc gcgccttcgc tgtcctattc | 1200 |
| aatgtattgg ggatcgaagc ccccgaccgc gaacgccttg ccttctatct gcgattggac | 1260 |
| cctctgactt ggggttgatg ttcatgccgc ctgtttttcc tgctcattgg cacgtttcgc | 1320 |
| aacctgttct cattgcggac acctttttcca gcctcgtttg gaaagtttca ttgccagtaa | 1380 |
| taccaatgct ttagaaagaa aaggatcgaa cttttgacat tcgatcccct tttctgtaat | 1440 |
| ctgtttcgtg cgttctttgc taagatacag accctagaca agtcatatct tagcaaaggg | 1500 |
| tagctagtaa tgcaagagat tgcgaagcgt ccctactacc aaaaaaccat tcaacgacgt | 1560 |
| aaacagacaa acgcaaacct taaattagac ggtcttcagc tcggacttcg gaagaataaa | 1620 |
| caggcgtaga agtgataacg ttcttaatac gaaaattaag ctctgtctcc gtttcgtgct | 1680 |
| acggttagaa acggaaagcc ccaagaaata caagcacacc tgataagcga gatttaagga | 1740 |
| taacagcgaa attcaatagg gtctgaattt ccaaactagg ttaaatgcca cgacgtttta | 1800 |
| ttgttgcccc attcaagcaa catttgagaa ccgaatagaa atctttagt aaaaagcgtt | 1860 |
| ctttttttggg tcagcggtta atgtggacgg tttaacggtt tttcctgcgg gtcgtattgg | 1920 |
| aaagccattg aaaagctgat ggataactct gcgagttacc cacgagcttt ccaacagctt | 1980 |
| tccaacacta aaaacctacc gcccacaata accacttccc taataataaa attttttat | 2040 |
| ttttattttg gttcaaagct cacgatgttc gcctaataaa acgaagtccg tatcgcgtcc | 2100 |
| gctgattttt atatatcact ctcggggctt ttggtgtact attgtctttt gtaatagcaa | 2160 |
| ggacacaaaa agggtactct tcgagtttcc ttttgacct tgcaaaaggc tttgcccct | 2220 |
| tgaccccga ccgctttcag cggtcaaaat agaagaacgg acaccattat gaaacgtgag | 2280 |
| aaagagataa aaatcaggct caccgaaaac gagtatcaag ccttgttaga gagaaaaacg | 2340 |
| aaagcaaggc ttgcggagtg ggttcgggaa gttgccctgg aacagcaacc taagcgacag | 2400 |
| ccgaaagtaa tcgaccctgc gttactgttc gagctgaacc gcataggcgt aaacctgaac | 2460 |
| caaatcgccc gacaatgcaa cagtcaaaag ccgagcattg accttgttag cgtgttggcg | 2520 |
| accttgcgag aaattgaaaa aaatctcaaa aaattgcgag aattgagcct atgatcgtta | 2580 |

```
aattttttaa gaaacacggt aagggaaaag ctagtagttg caaggcttgc gtggactatt    2640
tactaaataa gcctgacgac accgcccaaa tcctgcaggg cgatccccga ctatcacaaa    2700
gtattgctga tagtcttgat tttaataaca cttacaccgc aggttgcttg tcttttgaag    2760
aaagcgacct acccgaaata caaaagcgtg agattatggc acgctttgaa aaggcaatgt    2820
ttgcagggct tgagcctgaa caatataaca ttgcgtgggt acaacacacc gacaaaggca    2880
ggcttgagct gaatttcgtt atcccaaacg tagagatgac aagcggaaaa cgcctacaac    2940
cctactacga cagggcagac cgccacttgc tgaaaacttc aagcaggtaa tcaaccacga    3000
atacagccta agcgacccaa acaaccctat aaagcaaaaa acctgattga ccgcaaagac    3060
ctaccaaccg ataaaacagg ctttacaggc gattacggac ggtttaacag ctttagcgaa    3120
cgcagggcag ataaacgacc gacaggacgt tataaatgcc ctagaacgtg caggttttga    3180
aattgcacgc attacgccaa aaaacctatc aatcaagact gacggacaga atttaagatt    3240 aaaagggggct ttctatgagc aagattttag atttagcaca gacctttcag cagacatcac    3300
agaaagagct agagagtaca agcgagatag tgcagaacgc tatcaaacgg cacgagcaaa    3360
acttgataca gcagttacag cacgcaggga acaatttagc cgaaaatatc caaatcgagc    3420
aggcgaaatt gataaaaaat accgtgagaa tgtatcgctt ccgaccccta atcgccttga    3480
cgatattaac cttgatagcc ataaccactc catatccgga tcattcaaca gtacaacgaa    3540
atcagcgagc aattaacgac attacagagt ttaataaaca gcttgaaacg gtaatatctc    3600
aacgcaaaag acaaagcagg ggtatgagca gataaaacaa ggggggagaat tatggcaaca    3660 cttatggaaa aagacagttt aataaatggt atttctcaaa cactcggctt attgtaagat    3720
gtcggtagga agtactcatc atttggaagt ggttttttgtg tggaaacaaa attatattct    3780
agttgatgag tacttctttt tttgttcac ttggattgta aattcagccc taaattttca    3840 cttttttctaa caaaatgaat ttgttagttg agctgtaaag tatgaaatac ttgctttgct    3900
gcatcttcta ctaatttatt gttgaatttg gcttcttcgg taaattgcgt actcatgatt    3960
gccatcacaa tcggtttgcg atttggtatg cgaaccaccg caatatcatt gcgtacacca    4020
tatttacccg ccccgctttt atcgtacact ttccacgatg ttggcgtagc agcgcgaatc    4080
aatggattgc ctgttgcgtt attgtccaac caattccaca aaatcgtttt ttgcgattcg    4140
gttaatgtgt tgcccaataa atacgcattt aaattcatcg ccatttgttt gggtgtactc    4200
gtatcacgaa tatcgttggg tttggcttga tttaaatcgg gttctagccg attggtatgg    4260
gttacgttat cgcctaattg tcgcaaaata cgttgatatt gttccacgcc acccaattct    4320
ttgagcagca aattggtcgc gctgttgtcg ctaaaccgca cggctgcttc acataattgg    4380
gcaatcgtca tgcctttgcc aacgtatttt tgggtttcgg gagaataact aaccaaatct    4440
ttttggctat atgaaatggt acgatttaaa tcttttttcag cagcgattg caacaccgcc    4500 ccagccaaca acgccttgaa agtggacgca taagcaaagc gttcatctgc acgataagac    4560
aaagaatgtc ccgtttctgt atcccataca taaacgccaa ttcgggcttg atactgctgt    4620
tccaaattcg ccaagtctg ttgaaaggtg gcttgtgtgg ctgattgttg cacaggcgca    4680
ctagcaggct gcggattaga cgttaccgaa tgaacagaat tgggcgaaca agccgttaat    4740
gtcagcaata ataatgtgcc gattttttaac ttatttaaca taaattatcc tttgatttta    4800
ctaaataaat ttcttttcag cagcctgaa acgtacattg cgcggaaatt cggataattt    4860
gtttgtagaa caaaaaaaca gattttggcg aatttaagcg caaaagtcta gcaatttagc    4920
```

-continued

| | |
|---|---|
| ctttaatctc aatgctttct acaatgaaat gcactttgat attctcaagt aagttcgcct | 4980 |
| ctaggtatgc aatttgcttg tctaagtctt gaagcggata ataacccttg ccccaattc | 5040 |
| gtagaggttt cacataaatc accccttag cactataagg ctaagcgact aggctcacac | 5100 |
| tatgaacggt agtgcgagcc gccgccatag tgcgaaagtg attttaacac ataaccgcct | 5160 |
| aacaaggcgg ttttgtttta ttcgggactg aaaaagccgt tgaaacttgc tttcaatggc | 5220 |
| ttttttagtc taacaaccgc agggcgttag cagaaaggtg ca | 5262 |

<210> SEQ ID NO 6
<211> LENGTH: 8501
<212> TYPE: DNA
<213> ORGANISM: Pasteurella haemolytica

<400> SEQUENCE: 6

| | |
|---|---|
| ggatccattt caatgctgat ttccgcatca tcgctcacat caaaattggc tcgtagcatt | 60 |
| tgcattaaac gtgccgattg atcttcgtct aaataagtcg gcgtaccgcg accccagtgt | 120 |
| atttgggtca ctaaacgatt ttgaaacaga ggtgcgcgag ttttaatttc acgctctaaa | 180 |
| taatctaaat aaatttcaac tttatggcga tgacgagtaa tcactttatt acagccacag | 240 |
| aaatagcaca gttatggca aaacggaata tgcacataaa gcgaaagcgg acgctcaggg | 300 |
| taacgagctg cagcacgaat aaaatcttca ttggtgtaat tttcgttaaa ctccaacgct | 360 |
| gttgggtaag aggtataacg aggccctgaa tggttatatt tttgaataag gctaaatcc | 420 |
| caaataattt ctgacattag attgcctttc tcatttcttc aatatctttt ataattggt | 480 |
| aacactcatt tttgatgtct gattcaagct ccgcttcttt tgcttcccgc tctaaatcca | 540 |
| acttcattct ttcgttacgt tttaaatttt tgcgttcatc taaaatcggc atattttcta | 600 |
| ccacgccata caacgcccac atcgccgtat agtcgcttaa ttttctgccg agaacatcta | 660 |
| atagcggttt taaacgtaaa acgccttccg aaaaatcgca ctgttctgaa atcattgccc | 720 |
| gagcaataac ttcaatgctg tctaaaatcc gaatataacg atcttttgt gcttgctttg | 780 |
| cctgttcaat cagtgcttgt tcgtgctttt tctgagctcg cactttcagc attaagtgca | 840 |
| gtgcataccc gcccagcgaa attaaaatca agcggcaag caccatcagg aatattctta | 900 |
| gcatcataat cggctaccta gcggaattta ttaatatcca tcgtttcaaa ttggcgtaat | 960 |
| aacgcatcgc cattatcgcc ctcttcatct tcatattcga tgccaagctc agtcattaat | 1020 |
| tcatcaatgc gatctaaaca ttcattcata aatttctgat cttctgcgga taaggttttg | 1080 |
| cccgcctcca atcatctaa caactgattt aaacattcgt tatttctaa ctgctccagc | 1140 |
| tcttgttccg gtgaaagcgt tggtttgatt ggctcaaccg gcacagcctt aatcgtccgc | 1200 |
| ccttttccg gctggttcac aaattccacc attaacggca cttttttacg gctaccgata | 1260 |
| cgcggatctt tcacctcttt caccactgct tttttctgct ctgccggatc agcattgcgt | 1320 |
| gagcctgtcg gcaagccttt atgtttacgc ttacgttttt cctcacgggc ttgagcatct | 1380 |
| aactcataac gggtcagttt gcgattttc cccccaccta atttaggcat gggctgttta | 1440 |
| ggtttatcgg tctttcttgc cggcataatg tcggtaatac gacgtgtttt tttagtacga | 1500 |
| ctcataaatt taatatctta aaattgctat aaacggctat tctacaagga attagatttc | 1560 |
| cttaatagct ttggtttcaa ttaatcattt caatcaatga taagtttgca caaaatgttg | 1620 |
| gtaggctttc aaaaatttct caaagtcatc taagccacaa aatgcgatgc tctcttcatt | 1680 |
| gtaaaattga aagccttctt ccatttcctc atcatcaaaa gcagcatcta aattgtttgc | 1740 |
| ttttgccatc acttcatcat aatcaaaata gagactatac tcccgcccct caaacacaca | 1800 |

```
ttcataatga ttcggaaatg cggctcgaca cttctctatt tcagcgaaaa tagggctaa    1860
ctggctagga ttttccgtta tttcggcatt caaccaacga gcaaacgcct cgtgatccat    1920
cgaacatttt gccaccaccc cgtgaatact atgggtaaat tgatattcca taccgattct    1980
cctttgaatt ggtctgtttg gttggctatt atagcctaac aagcggtctt ttttttggaaa    2040
attttgcaaa acgctaattt ttaaatgtta tcaactcctc gattacccag aaatctgcta    2100
gaataataca ggttattttt agtattgata catcaaaaag gaactactat gccaaacagc    2160
acagcacagc acagcacagc acagcacagc acagcacagc acagcacagc acagcacagc    2220
acagcacagc acagcacagc acagcacagc acagcacagc acagcacagc acagcacagc    2280
acagcacagc acagcacagc acagcacagc acagcacagc acagcacagc acagcacagc    2340
acagcacagc acagcgtgat ctcaacgtct gacacaagtc aagcctttt aaacgaactc    2400
gaccaaaccc tctggactgc cgccgacaaa ctgcgtaaaa acctcgatgc cgccaactac    2460
aaacacatcg ttcttggctt tatcttccta aaatacatct ccgacagctt taccgatttc    2520
caagccaagc taaaaaccca gcttaccacc cccgaaagcg aactctatct tgaccctgca    2580
ctatttgacg aacaagaatt tagccaaatt cttgccgaag agttggaaca gagagattac    2640
tacgccgctg aaaacatctt ttgggtgccg gagcaagccc gctgggacaa catcaaatca    2700
ttaagcaaac tcaatcttgg cgatgaattg ccttggggag acaaatttaa aggtgtcagc    2760
cgcttgattg atgatgcctt tgaagccatc gaacgggaaa accccaaact caaaggcgta    2820
ctccaacgca ttgccggctt tggcgtgcct gatgaaatgc tcacaggctt aattgacctg    2880
ttctcacgca ccaatttcac ccagcctatg cacaatggcg aacctgtgca tctgcaagcc    2940
aaagacattt tagggcacgt ctatgaatac tttcttgggc aatttgccct tgccgaaggc    3000
aaaaaaggcg gtcaatactt cacgccaaaa tccatcgtta ccctgattgt tgaaatgctc    3060
gaaccctatt cagggcggat ttacgaccca gctatgggca gcggcggctt ttttgtgcaa    3120
gctgaccgct ttattcaggc tcacgcaggc aaccgcaacg ccatttccgt ttatgggcaa    3180
gaatccaact ccaccactcg caaactggcg gtgatgaata tggcgattcg tggtattccc    3240
tttgactttg gcgacaagcc cgaagatacc ctactaaacc cttttgcacat cgacaaaaaa    3300
atggatgttg tgatggcaaa tccgcccttt aaccaaaaag agtggtggaa tgaaagccta    3360
gcaaacgatc cacgctgggc atacggcaca ccgccgcaag gcaacgccaa ctttgcgtgg    3420
ttgcaacata tgatttacca cctctccccc aaaggcaaaa tggcactcct gcctcgcaac    3480
ggctcaatga gcagccaaac ttcaggcgaa ggcgacattc gcaaaaacat cgtgcaagct    3540
gaccttgtcg aagcgatgat tgccctgccc aatcagctat tcaccaacac ccaaatccct    3600
gcctgcattt ggattatcaa taaagccaaa gccagaaaag gtgaagtgct gtttatcaac    3660
gccacccaaa taggctacct gaaggaccgc gtcttgcgtg attttaccgc tgatgacatc    3720
gccaaaatca gcgacaccta ccacaactgg caaaaacaga acggctacga aaatatccct    3780
gcgtttttgtt attgtgccac gctggacgaa atcgccaaaa acgattttgt gctgaccgca    3840
gggcgatatg tcggtgcggt acaagaagaa aatgacggcg tgcggtttgc agaaaaaatg    3900
caggaattga ccgctttatt gaatgaacaa tttaaacaag gcgggaatt ggaacagcaa    3960
atcgcagaga atttaaaggg gttgggatat ggcatttaat cagtatgtat tttcagatat    4020
tgttgaatta atatccgaaa aaataaaaat caaagactta aaaaaagaaa actatatttc    4080
gacagataat atgctgccta attttggtgg aataacactt gctgaaaacc ttccaaattc    4140
```

```
agcttcttgc aataggtttg ccaaaaaaga cattttgttt tccaatataa gaacctactt    4200
taaaaaagtt tggcttgctg aattttcagg tggttgttct cctgatgttc tggtaatgcg    4260
cagtaaaaac acagatattt tattaaatga gtatttattt ttacttatcc gttctgatga    4320
ttttattaac tttacagtta tatcagcaaa tggagcaaaa atgccacgag gggataaaaa    4380
tgcaatgaaa ggttttattt tcaatatccc aagtattgaa tatcaaaaaa aatgtattgc    4440
taattatttt gcctttgacc aaaaaatcca actcaacacc caaaccaacc aaaccctaga    4500
agccattgca caggcaatct tcaaaagctg gtttgtggat tttgaccctg tgcgcgccaa    4560
agccgccgcc ctaagcgaag gcaaaagcga acacgaagcc aaccttgcgg caatgtcggt    4620
gatttgtggt aaagacacca gcgagttaaa cgacaccgaa tacaaagcgc tttggcaaat    4680
cgccgaagcc ttcccaagtg agtttggaga tgaagggtta cctattggct ggaaattcaa    4740
tcaagcagac aatttatttg atgttggtat tgggaaaacc ccaccaagaa aagagagtga    4800
atggttttct gataatgcaa atgatacaga atggatttct attaaagata tgggaaatca    4860
gggattattt atcacagaaa gtagcgaata tctaaaagct gaagccgtag atacatttaa    4920
tattaaaaga attcctgaaa atactgtaat tttgagtttt aaattaaccg ttggtagagt    4980
ttcaattacg acaaaagaaa caactactaa cgaagctatt gctcatttta aaattcctag    5040
ctcatcaaat ctaagctcag agtttttata ctgctactta aaaaattttg attttaataa    5100
tctaggaagt acatcatcaa tcgcaacggc agtcaattca aaaatgataa aagagatgga    5160
aattttagaa ccatcagttc tagttattaa tcactttaat gaatatattg aaggtatttt    5220
taataagata aaagaaaata ttattcaaaa taataactta tctaaaatta gagataagtt    5280
attacctaaa ttattaagtg gggagatgga gttgtgatga ttaccatcaa cgaaaacacc    5340
attgaacaat ccgccattgc aactttgcaa agcttgggct gggactacac ctacggcaaa    5400
aaaattttgg caggtttaga acacgaatgg cgggacggaa ccgctgaggt gattttaaag    5460
ccgcttttgg cgcaagcgat tgcaaaattc aacccgaatt tgcccgcttg tgaggtggaa    5520
aatgtggtgg cacaggtgtg ccgtgccgac agtggcgatt tggcggacgg taatcgtcag    5580
gcttatgatt ggctaagaaa tggggtcaaa atcacttatc agttgtacgg tgagcaggtg    5640
tctgatgtgg tgcagctgat tgattttcag cgtccagaaa ataacgattt tcgcattgtc    5700
aatcagctgg atattagcgg caaaaaaggc aaacgcattc cggatttgat tggctttgtt    5760
aatggcttgc cgctggtggt gtttgagctg aaaaatccgc tcaaagaaaa tgccgacatt    5820
ggcaaggcgt tgcccaact gcaaacctat aaagatgaaa tttctgattt gtttgtgttt    5880
aatcaggcac tcgtgatttc agacggcatt gtcgcccgca tcggttcgct gaccgctgat    5940
ttcgaccgtt ttacccttg gcgtgtggtt gatgaaaaaa atcagagcaa acgcattgtg    6000
tttgaagatg aactcaccgc cctgctgcaa ggcgtgatga cacccaaaaa tctcttggat    6060
tatgtgcaga ttttgtggt gtttgaacgg gacggcaaaa accgcttaat taagaaaatc    6120
ggagcatatc atcagttttta tggcgtgaat gaagcggtgg attgcacctt gcttgccgcc    6180
acaggcaacc gcaaaatcgg cgtgttttgg catacgcaag gttcgggcaa atcgctttcg    6240
atgctgtttt atgcaggtaa agtattaagc caaagcagcc tgaaaaatcc aactttggtg    6300
ttggtaaccg accgcaacga tttggacggt cagctttacg ccacttttttg cggtggcgag    6360 gcactgctca acaaacgcc aatccaagcc gatgggcgag acgaactccg ctctgccctt    6420
gccagtcgtt cggcaggcgg tgtgattttt accaccattc aaaaattcgg cttaatggag    6480
ggtgagcttg cccacctgt attaaacgag cgggaaaaca tcattgtgat taccgatgaa    6540
```

```
gcacaccgct cacaatatgg ttttagccaa aaaatcaacc acaaaggcga gtatcgtgag      6600
ggttatgcca agcatttacg cagtgcattg ccgaatgcct cttttattgg ctttactggc      6660
acaccgattg aacttgatga caaagacacc caagaagtct tcggtaaata tgtctcgatt      6720
tatgattttg aagatgcggt ggaagatggg gcaaccgtgc cgattattta tgagccacgc      6780
caaatcagct taggcgaaag tggcgagttt tccaaagtga tggaagaggc acaacaactg      6840
attgatgacg atgaaaacag ctataacttc cgcctgcgtg aaaaactgca cagcgtggat      6900
agccgtttgc aaaaaatggc ggaagatatt attgcccatt acgatgagcg taccaaacag      6960
caagacggca aggcgatggt tgtggtgatg agccgtgcca tttgcgtgaa attgtacgaa      7020
aaaatcaccg cacttcgtcc agaatggcac tcaaacgatg tgcttcaagg cagcattaaa      7080
attgtgatga caagtaatgc cagcgaccct gccgagtggc aaaaacacaa tcaggataag      7140
aaaaccttag aaaaacgctt taagaccca gacgatccgc tcaacatcgt gattgtgcgg       7200
gatatgtggc tgacaggctt tgatgcgccc tgctgtaaca caatgtacat tgataaacca      7260
atgagcggac acaacctgat gcaggcaatc gctcgggtaa atcgggtatt tcgcaacaaa      7320
agccgtgaaa atggcggctt gattgtggat tatgtgggct tgaccgatga gctggaaaaa      7380
gcgatgaagc agtacaccaa cgcaggcggt aaagaaaagc cggtgcggga catttcagcg      7440
gtgctggaaa aaatggtgga acatatcacg gtcattcgtg ggcaatttgc acaccgattg      7500
acggacaagc ggttgatatt gccaaaaatg ttgcaaatca gcgaaccgcc taaactgctc      7560
aatgcgattt tgacatcagc caaccatatt cttgccctag accgcattca gccacctgat      7620
aacactgcca agacaaaac cccacgcaaa acgcctttt tgcaatcggt acgcttggcg       7680
gaaaaaggtt atgctttgtg tggggcatta aaagcagttg aaccctataa acaggaactg      7740
gcgttttatg atgcagtgcg tgccaccatt atcaaaaaca gcaccgctcc tcgcaattct      7800
tcgagcgaaa atgaccgctt gttgcagctt accgccttga tgaatcgtgc ggtacagtcg      7860
gatggtgtgg tggattttatt tgatttgctg aaaaaagacc gcccaaacat caacctgctt      7920
tctgatgagt ttttggaaac agtaaaaaac agcccaacca aagatttgtg gctatcagca      7980
atggagcgtt atcttgcctc acaactgcga gacgaaagcg gtgccaatct tgccacaaaa      8040
aaagcatttg aacagaaact caaagaggcg atgaaccaat accacaacca caatttaagc      8100
gtattggaaa ttttagaaga gctgatcgcc ctcgccaaag agtttgaagc ccgccaaaaa      8160
cgaggggaag cgttgggact aagccctgcg gaaatggcgt tttatgatgc tttggcacgt      8220
aatgaaagtg cggtgcggga atgggcgat gaggtattga tgaaacttgc caaagacatt      8280
accgataaat tacgcaaatc ggtcaccgta gattggcaat ataaagactc ggttcgtgcc      8340
aaaatgcgaa ccttaatcgc attgctctgc gtacctataa atacccgccc gatttacagg      8400
cggaagcgat tgagtttgtg ttgcaacaag cggaagagat cgccggagag ttcgctatca      8460
ccgaaacggc gtaatctata ttagggcgtg caatgtacgc c                         8501
```

<210> SEQ ID NO 7
<211> LENGTH: 17
<212> TYPE: DNA
<213> ORGANISM: Pasteurella haemolytica

<400> SEQUENCE: 7

```
tgtnnnnnnn nnnnaca                                                      17
```

<210> SEQ ID NO 8

```
<211> LENGTH: 18
<212> TYPE: DNA
<213> ORGANISM: Pasteurella haemolytica

<400> SEQUENCE: 8
tgtnnnnnnn nnnnnaca                                                   18

<210> SEQ ID NO 9
<211> LENGTH: 2445
<212> TYPE: DNA
<213> ORGANISM: Pasteurella haemolytica

<400> SEQUENCE: 9
gaaagccttc ttccatttcc tcatcatcaa aagcagcatc taaattgttt gcttttgcca     60
tcacttcatc ataatcaaaa tagagactat actcccgccc ttcaaacaca cattcataat    120
gattcggaaa tgcggctcga cacttctcta tttcagcgaa aatagggggct aactggctag   180
gattttccgt tatttcggca ttcaaccaac gagcaaacgc ctcgtgatcc atcgaacatt   240
ttgccaccac cccgtgaata ctatgggtaa attgatattc cataccgatt ctcctttgaa   300
ttggtctgtt tggttggcta ttatagccta acaagcggtc ttttttttgga aaattttgca  360
aaacgctaat ttttaaatgt tatcaactcc tcgattaccc agaaatctgc tagaataata   420
caggttattt ttagtattga tacatcaaaa aggaactact atgccaaaca gcacagcaca   480
gcacagcaca gcacagcaca gcacagcaca gcacagcaca gcacagcaca gcacagcaca   540
gcacagcaca gcacagcaca gcacagcaca gcacagcaca gcacagcaca gcacagcaca   600
gcacagcaca gcacagcaca gcacagcaca gcacagcaca gcacagcaca gcacagcaca   660
gcacagcgtg atctcaacgt ctgacacaag tcaagccttt ttaaacgaac tcgaccaaac   720
cctctggact gccgccgaca aactgcgtaa aaacctcgat gccgccaact acaaacacat   780
cgttcttggc tttatcttcc taaaatacat ctccgacagc tttaccgatt ccaagccaa    840
gctaaaaacc cagcttacca cccccgaaag cgaactctat cttgaccctg cactatttga   900
cgaacaagaa tttagccaaa ttcttgccga agagttggaa cagagagatt actacgccgc   960
tgaaaacatc ttttgggtgc cggagcaagc ccgctgggac aacatcaaat cattaagcaa  1020
actcaatctt ggcgatgaat tgccttgggg agacaaattt aaaggtgtca gccgcttgat  1080
tgatgatgcc tttgaagcca tcgaacggga aaaccccaaa ctcaaaggcg tactccaacg  1140
cattgccggc tttggcgtgc ctgatgaaat gctcacaggc ttaattgacc tgttctcacg  1200
caccaatttc acccagccta tgcacaatgg cgaacctgtg catctgcaag ccaaagacat  1260
tttagggcac gtctatgaat actttcttgg gcaatttgcc cttgccgaag caaaaaagg   1320
cggtcaatac ttcacgccaa aatccatcgt taccctgatt gttgaaatgc tcgaacccta  1380
ttcagggcgg atttacgacc cagctatggg cagcggcggc tttttttgtgc aagctgaccg 1440
ctttattcag gctcacgcag gcaaccgcaa cgccatttcc gtttatgggc aagaatccaa  1500
ctccaccact cgcaaactgg cggtgatgaa tatggcgatt cgtggtattc cctttgactt  1560
tggcgacaag cccgaagata ccctactaaa ccctttgcac atcgacaaaa aaatggatgt  1620
tgtgatggca aatccgccct ttaaccaaaa agagtggtgg aatgaaagcc tagcaaacga  1680
tccacgctgg gcatacggca caccgccgca aggcaacgcc aactttgcgt ggttgcaaca  1740
tatgatttac cacctctccc ccaaaggcaa aatggcactc ctgcctcgca acggctcaat  1800
gagcagccaa acttcaggcg aaggcgacat tcgcaaaaac atcgtgcaag ctgaccttgt  1860
cgaagcgatg attgccctgc ccaatcagct attcaccaac acccaaatcc ctgcctgcat  1920
```

-continued

```
ttggattatc aataaagcca aagccagaaa aggtgaagtg ctgtttatca acgccaccca  1980
aataggctac ctgaaggacc gcgtcttgcg tgattttacc gctgatgaca tcgccaaaat  2040
cagcgacacc taccacaact ggcaaaaaca gaacggctac gaaaatatcc ctgcgttttg  2100
ttattgtgcc acgctggacg aaatcgccaa aaacgatttt gtgctgaccg cagggcgata  2160
tgtcggtgcg gtacaagaag aaaatgacgg cgtgcggttt gcagaaaaaa tgcaggaatt  2220
gaccgcttta ttgaatgaac aatttaaaca agggcgggaa ttggaacagc aaatcgcaga  2280
gaatttaaag gggttgggat atggcattta atcagtatgt attttcagat attgttgaat  2340
taatatccga aaaataaaa atcaaagact taaaaaaga aactatatt tcgacagata  2400 atatgctgcc taattttggt ggaataacac ttgctgaaaa ccttc         2445
```

<210> SEQ ID NO 10
<211> LENGTH: 94
<212> TYPE: PRT
<213> ORGANISM: Pasteurella haemolytica

<400> SEQUENCE: 10

```
Met Glu Tyr Gln Phe Thr His Ser Ile His Gly Val Val Ala Lys Cys
  1               5                  10                  15

Ser Met Asp His Glu Ala Phe Ala Arg Trp Leu Asn Ala Glu Ile Thr
             20                  25                  30

Glu Asn Pro Ser Gln Leu Ala Pro Ile Phe Ala Glu Ile Glu Lys Cys
         35                  40                  45

Arg Ala Ala Phe Pro Asn His Tyr Glu Cys Val Phe Glu Gly Arg Glu
     50                  55                  60

Tyr Ser Leu Tyr Phe Asp Tyr Asp Glu Val Met Ala Lys Ala Asn Asn
 65                  70                  75                  80

Leu Asp Ala Ala Phe Asp Asp Glu Glu Met Glu Glu Gly Phe
                 85                  90
```

<210> SEQ ID NO 11
<211> LENGTH: 616
<212> TYPE: PRT
<213> ORGANISM: Pasteurella haemolytica

<400> SEQUENCE: 11

```
Met Pro Asn Ser Thr Ala Gln His Ser Thr Ala Gln His Ser Thr Ala
  1               5                  10                  15

Gln His Ser Thr Ala Gln His Ser Thr Ala Gln His Ser Thr Ala Gln
             20                  25                  30

His Ser Thr Ala Gln His Ser Thr Ala Gln His Ser Thr Ala Gln His
         35                  40                  45

Ser Thr Ala Gln His Ser Thr Ala Gln His Ser Thr Ala Gln His Ser
     50                  55                  60

Thr Ala Gln His Ser Val Ile Ser Thr Ser Asp Thr Ser Gln Ala Phe
 65                  70                  75                  80

Leu Asn Glu Leu Asp Gln Thr Leu Trp Thr Ala Ala Asp Lys Leu Arg
                 85                  90                  95

Lys Asn Leu Asp Ala Ala Asn Tyr Lys His Ile Val Leu Gly Phe Ile
                100                 105                 110

Phe Leu Lys Tyr Ile Ser Asp Ser Phe Thr Asp Phe Gln Ala Lys Leu
            115                 120                 125

Lys Thr Gln Leu Thr Thr Pro Glu Ser Glu Leu Tyr Leu Asp Pro Ala
        130                 135                 140
```

-continued

```
Leu Phe Asp Glu Gln Glu Phe Ser Gln Ile Leu Ala Glu Glu Leu Glu
145                 150                 155                 160

Gln Arg Asp Tyr Tyr Ala Ala Glu Asn Ile Phe Trp Val Pro Glu Gln
                165                 170                 175

Ala Arg Trp Asp Asn Ile Lys Ser Leu Ser Lys Leu Asn Leu Gly Asp
            180                 185                 190

Glu Leu Pro Trp Gly Asp Lys Phe Lys Gly Val Ser Arg Leu Ile Asp
        195                 200                 205

Asp Ala Phe Glu Ala Ile Glu Arg Glu Asn Pro Lys Leu Lys Gly Val
210                 215                 220

Leu Gln Arg Ile Ala Gly Phe Gly Val Pro Asp Glu Met Leu Thr Gly
225                 230                 235                 240

Leu Ile Asp Leu Phe Ser Arg Thr Asn Phe Thr Gln Pro Met His Asn
                245                 250                 255

Gly Glu Pro Val His Leu Gln Ala Lys Asp Ile Leu Gly His Val Tyr
            260                 265                 270

Glu Tyr Phe Leu Gly Gln Phe Ala Leu Ala Glu Gly Lys Lys Gly Gly
        275                 280                 285

Gln Tyr Phe Thr Pro Lys Ser Ile Val Thr Leu Ile Val Glu Met Leu
    290                 295                 300

Glu Pro Tyr Ser Gly Arg Ile Tyr Asp Pro Ala Met Gly Ser Gly Gly
305                 310                 315                 320

Phe Phe Val Gln Ala Asp Arg Phe Ile Gln Ala His Ala Gly Asn Arg
                325                 330                 335

Asn Ala Ile Ser Val Tyr Gly Gln Glu Ser Asn Ser Thr Thr Arg Lys
            340                 345                 350

Leu Ala Val Met Asn Met Ala Ile Arg Gly Ile Pro Phe Asp Phe Gly
        355                 360                 365

Asp Lys Pro Glu Asp Thr Leu Leu Asn Pro Leu His Ile Asp Lys Lys
    370                 375                 380

Met Asp Val Val Met Ala Asn Pro Pro Phe Asn Gln Lys Glu Trp Trp
385                 390                 395                 400

Asn Glu Ser Leu Ala Asn Asp Pro Arg Trp Ala Tyr Gly Thr Pro Pro
                405                 410                 415

Gln Gly Asn Ala Asn Phe Ala Trp Leu Gln His Met Ile Tyr His Leu
            420                 425                 430

Ser Pro Lys Gly Lys Met Ala Leu Leu Pro Arg Asn Gly Ser Met Ser
        435                 440                 445

Ser Gln Thr Ser Gly Glu Gly Asp Ile Arg Lys Asn Ile Val Gln Ala
    450                 455                 460

Asp Leu Val Glu Ala Met Ile Ala Leu Pro Asn Gln Leu Phe Thr Asn
465                 470                 475                 480

Thr Gln Ile Pro Ala Cys Ile Trp Ile Ile Asn Lys Ala Lys Ala Arg
                485                 490                 495

Lys Gly Glu Val Leu Phe Ile Asn Ala Thr Gln Ile Gly Tyr Leu Lys
            500                 505                 510

Asp Arg Val Leu Arg Asp Phe Thr Ala Asp Ile Ala Lys Ile Ser
        515                 520                 525

Asp Thr Tyr His Asn Trp Gln Lys Gln Asn Gly Tyr Glu Asn Ile Pro
    530                 535                 540

Ala Phe Cys Tyr Cys Ala Thr Leu Asp Glu Ile Ala Lys Asn Asp Phe
545                 550                 555                 560
```

-continued

```
Val Leu Thr Ala Gly Arg Tyr Val Gly Ala Val Gln Glu Glu Asn Asp
            565             570                 575

Gly Val Arg Phe Ala Glu Lys Met Gln Glu Leu Thr Ala Leu Leu Asn
            580             585                 590

Glu Gln Phe Lys Gln Gly Arg Glu Leu Glu Gln Gln Ile Ala Glu Asn
            595             600             605

Leu Lys Gly Leu Gly Tyr Gly Ile
    610             615
```